United States Patent
Qian

(10) Patent No.: US 10,487,108 B2
(45) Date of Patent: *Nov. 26, 2019

(54) CERTAIN STEROIDS AND METHODS FOR USING THE SAME IN THE TREATMENT OF CANCER

(71) Applicant: NEUPHARMA, INC., Foster City, CA (US)

(72) Inventor: Xiangping Qian, Foster City, CA (US)

(73) Assignee: NEUPHARMA, INC., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/586,710

(22) Filed: May 4, 2017

(65) Prior Publication Data

US 2017/0362271 A1    Dec. 21, 2017

Related U.S. Application Data

(63) Continuation of application No. 14/397,845, filed as application No. PCT/US2013/038705 on Apr. 29, 2013, now Pat. No. 9,676,813.

(60) Provisional application No. 61/639,930, filed on Apr. 29, 2012.

(51) Int. Cl.
| | | |
|---|---|---|
| C07J 41/00 | (2006.01) | |
| C07J 19/00 | (2006.01) | |
| C07J 43/00 | (2006.01) | |
| C07J 71/00 | (2006.01) | |

(52) U.S. Cl.
CPC ........... C07J 41/0011 (2013.01); C07J 19/00 (2013.01); C07J 41/0005 (2013.01); C07J 43/003 (2013.01); C07J 71/0021 (2013.01)

(58) Field of Classification Search
None
See application file for complete search history.

(56) References Cited

U.S. PATENT DOCUMENTS

| | | | |
|---|---|---|---|
| 3,879,379 A | 4/1975 | Stache et al. | |
| 3,901,882 A | 8/1975 | Meyer | |
| 3,981,982 A | 9/1976 | Oslapas et al. | |
| 4,045,480 A | 8/1977 | Finke et al. | |
| 4,064,227 A | 12/1977 | Brown et al. | |
| 4,082,747 A | 4/1978 | Chen | |
| 4,115,539 A | 9/1978 | Eisenhardt, Jr. et al. | |
| 4,273,866 A | 6/1981 | Voss et al. | |
| 4,822,747 A | 4/1989 | Johnson et al. | |
| 5,045,480 A | 9/1991 | Johnson et al. | |
| 5,604,091 A | 2/1997 | Henderson | |
| 5,846,514 A | 12/1998 | Foster et al. | |
| 5,922,703 A | 7/1999 | Yu et al. | |
| 6,060,598 A | 5/2000 | Devlin et al. | |
| 6,334,997 B1 | 1/2002 | Foster et al. | |
| 6,579,857 B1 | 6/2003 | Lind et al. | |
| 8,114,636 B2 | 2/2012 | Agnew et al. | |
| 8,334,376 B2 | 12/2012 | Qian | |
| 8,575,376 B2 | 11/2013 | Chodounska et al. | |
| 8,993,550 B2 | 3/2015 | Qian | |
| 9,018,197 B2 | 4/2015 | Qian | |
| 9,340,570 B2 | 5/2016 | Qian | |
| 9,399,659 B2 | 7/2016 | Qian et al. | |
| 9,493,503 B2 | 11/2016 | Qian et al. | |
| 9,676,813 B2 | 6/2017 | Qian et al. | |
| 10,065,986 B2 | 9/2018 | Qian et al. | |
| 10,179,141 B2 | 1/2019 | Qian | |
| 2004/0082521 A1 | 4/2004 | Singh | |
| 2006/0009506 A1 | 1/2006 | Westwick et al. | |
| 2007/0060553 A1 | 3/2007 | Raymond et al. | |
| 2008/0027010 A1 | 1/2008 | Khodadoust et al. | |
| 2008/0050731 A1 | 2/2008 | Agnew et al. | |
| 2009/0023666 A1* | 1/2009 | Gardiner | C07J 19/00 514/26 |
| 2009/0075842 A1 | 3/2009 | Langenhan | |
| 2011/0201584 A1 | 8/2011 | Qian | |
| 2012/0053162 A1 | 3/2012 | Qian | |
| 2012/0196842 A1 | 8/2012 | Qian | |
| 2013/0005696 A1* | 1/2013 | Hu | C07J 41/0055 514/171 |
| 2013/0123224 A1 | 5/2013 | Qian | |
| 2015/0246944 A1 | 9/2015 | Qian | |
| 2016/0039865 A1 | 2/2016 | Qian | |
| 2016/0272671 A1 | 9/2016 | Xiangping | |
| 2017/0020897 A1 | 1/2017 | Qian | |
| 2017/0088580 A1 | 3/2017 | Qian | |

FOREIGN PATENT DOCUMENTS

| | | |
|---|---|---|
| CA | 2418458 A1 | 8/2004 |
| CH | 559219 A5 | 2/1975 |
| CN | 101016326 A | 8/2007 |

(Continued)

OTHER PUBLICATIONS

Schoenfeld et al., Origin of differences of inhibitory potency of cardiac glycosides in sodium/potassium-transporting ATPase from juman cardiac muscle, human brain cortex and guinea pig cardiac muscle. Biochemical Pharmacology, vol. 35(19), pp. 3221-3231 (Year: 1986).*

Annunziato, et al. "p-Maleimidophenyl Isocyanate: A Novel Heterobifunctional Linker for Hydroxyl to Thiol Coupling." Bioconjugate Chem. 1993, vol. 4, pp. 212-218.

Bundgaard. Design of Prodrugs. Elsevier, 1985.

Chen, S. "Advances in research on anticancer effects of cardiac glycosides." Pharm Care & Res, 2009, vol. 9, No. 6, pp. 401-404. (English Abstract Only).

European search report and opinion dated Jan. 3, 2014 for EP Application No. 11732631.4.

European search report and opinion dated Feb. 24, 2016 for EP Application No. 13784674.7.

(Continued)

*Primary Examiner* — Barbara P Badio

(74) *Attorney, Agent, or Firm* — Wilson Sonsini Goodrich & Rosati

(57) ABSTRACT

Chemical entities that are novel compounds, pharmaceutical compositions and methods of treatment of cancer are described.

42 Claims, No Drawings

(56) References Cited

FOREIGN PATENT DOCUMENTS

| | | | |
|---|---|---|---|
| CN | 101177445 A | 5/2008 | |
| CN | 101400690 A | 4/2009 | |
| CN | 102203112 A | 9/2011 | |
| CN | 102532235 A | 7/2012 | |
| EP | 0218010 A2 | 4/1987 | |
| EP | 0270937 A2 | 6/1988 | |
| EP | 0297290 A2 | 1/1989 | |
| EP | 0297292 A2 | 1/1989 | |
| JP | S6214064 A | 1/1987 | |
| WO | WO-9325197 A1 | 12/1993 | |
| WO | WO-9508559 A1 | 3/1995 | |
| WO | WO-9722596 A1 | 6/1997 | |
| WO | WO-9728808 A1 | 8/1997 | |
| WO | WO-9730035 A1 | 8/1997 | |
| WO | WO-9732856 A1 | 9/1997 | |
| WO | WO-9813354 A1 | 4/1998 | |
| WO | WO-9902166 A1 | 1/1999 | |
| WO | WO-0040529 A1 | 7/2000 | |
| WO | WO-0041669 A2 | 7/2000 | |
| WO | WO-0047212 A1 | 8/2000 | |
| WO | WO-0192224 A1 | 12/2001 | |
| WO | WO-0194341 A1 | 12/2001 | |
| WO | WO-0204434 A1 | 1/2002 | |
| WO | WO-0208213 A1 | 1/2002 | |
| WO | WO-0214343 A1 | 2/2002 | |
| WO | WO-0236128 A1 | 5/2002 | |
| WO | WO-2006002381 A1 | 1/2006 | |
| WO | WO-2007016656 A2 | 2/2007 | |
| WO | WO-2007081835 A2 | 7/2007 | |
| WO | WO-2010017480 A1 | 2/2010 | |
| WO | WO-2011031870 A1 | 3/2011 | |
| WO | WO 2011085641 A1 | 7/2011 | |
| WO | WO-2012027957 A1 | 3/2012 | |
| WO | WO-2012103810 A1 | 8/2012 | |
| WO | WO-2013000286 A1 | 1/2013 | |
| WO | WO-2013165924 A1 | 11/2013 | |

OTHER PUBLICATIONS

European search report and opinion dated Oct. 10, 2014 for EP Application No. 12741863.0.
Euw, J.V., et al., "197. Sargenosid ("Sarnnentosid B") and einige Derivate des Sarmentogenins." Helvetica Chimica Acta., 1952, vol. 35, No. 5 (No. 197-198), pp. 1560-1577. (with English Summary).
Evans. Synthesis of radiolabeled compounds, J. Radioanal. Chem. 1981; 64(1-2):9-32.
Gao, M., et. al., "Apoptosis of HepG2 Cell Induced by Ouabain and Cinobufogenin through ERK Signaling Pathway," China Pharmacy, 2010, vol. 21, No. 27, pp. 2500-2503.
Griffin, J.F., et al., "The Effect of 16p-Substitution on the Structure and Activity of Digitoxigenin: Is There an Additional Binding Interaction With Na+, K+-ATPase?" Molecular Pharmacology 29:270-274 (1985).
Hashimoto, et al. "Cardiac Glycosides. 6. Gitoxigenin C16 Acetates, Formates, Methoxycarbonates, and Digitoxosides. Synthesis and Na+, K+-ATPase Inhibitory Activities," J. Med. Chem. 1986, vol. 29, No. 6, 997-1003.
Higuchi, et al. Pro-drugs as novel drug delivery systems. American Chemical Society. ACS symposium series 14. 1975.
International search report and written opinion dated Mar. 31, 2011 for PCT/CN2011/000065.
International search report and written opinion dated Apr. 26, 2012 for PCT/CN2012/070817.
International search report and written opinion dated Sep. 17, 2013 for PCT/US2013/038705.
International search report and written opinion dated Dec. 8, 2011 for PCT/CN2011/001426.
Kalbalka, et al. The Synthesis of Radiolabeled Compounds via Organometallic Intermediates, Tetrahedron. 1989; 45(21):6601-21.
Kamano, et al. QSAR evaluation of the Ch'an Su and related bufadienolides against the colchicine-resistant primary liver carcinoma cell line PLC/PRF/5(1). J Med Chem. Dec. 5, 2002;45(25):5440-7.
Kamano, et al. Rhinovirus inhibition by bufadienolides. Chem Pharm Bull (Tokyo). Jan. 1988;36(1):326-32.
Kamano, et al. Structure-cytotoxic activity relationship for the toad poison bufadienolides. Bioorg Med Chem. Jul. 1998;6(7):1103-15.
Kibbe. Handbook of Pharmaceutical Excipients. 3rd Edition, American Pharmaceutical Association and Pharmaceutical Press (2000).
Langenhan, et al. Enhancing the anticancer properties of cardiac glycosides by neoglycorandomization. Proc Natl Acad Sci U S A. Aug. 30, 2005;102(35):12305-10. Epub Aug. 16, 2005.
Langenhan, et al. Synthesis and biological evaluation of RON-neoglycosides as tumor cytotoxins. Carbohydr Res. Dec. 13, 2011;346(17):2663-76. doi: 10.1016/j.carres.2011.09.019. Epub Sep. 29, 2011.
Liu, et al. Antitumor effects of venenum bufonis and its active components. (2009); 115-120.
Lombardo, et al. Discovery of N-(2-chloro-6-methyl-phenyl)-2-(6-(4-(2-hydroxyethyl)-piperazin-1-yl)-2-methylpyrimidin-4-ylamino)thiazole-5-carboxamide (BMS-354825), a dual Src/Abl kinase inhibitor with potent antitumor activity in preclinical assays. J Med Chem. Dec. 30, 2004;47(27):6658-61.
Matsumoto, et al. Cholestanol esters of amino acids. Bull Chem Soc Jpn. Jul. 1967;40(7):1650-5.
Mossman. Rapid colorimetric assay for cellular growth and survival: application to proliferation and cytotoxicity assays. J Immunol Methods. Dec. 16, 1983;65(1-2):55-63.
Newman, et al. Cardiac Glycosides as Novel Cancer Therapeutic Agents, Molecular Interventions, vol. 8, Issue 1, Feb. 2008, 14 pages.
Notice of allowance dated Jan. 7, 2015 for U.S. Appl. No. 13/219,372.
Notice of allowance dated Jan. 29, 2016 for U.S. Appl. No. 13/873,059.
Notice of allowance dated Mar. 22, 2016 for U.S. Appl. No. 14/625,329.
Notice of allowance dated Jul. 10, 2014 for U.S. Appl. No. 13/219,372.
Notice of Allowance dated Aug. 4, 2017 for U.S. Appl. No. 15/187,358.
Notice of allowance dated Aug. 20, 2014 for U.S. Appl. No. 13/673,842.
Notice of allowance dated Sep. 8, 2016 for U.S. Appl. No. 13/364,191.
Notice of allowance dated Sep. 10, 2012 for U.S. Appl. No. 13/007,516.
Notice of allowance dated Nov. 21, 2014 for U.S. Appl. No. 13/673,842.
Notice of Allowance dated Feb. 8, 2017 for U.S. Appl. No. 14/397,845.
Office Action dated Feb. 2, 2017 for U.S. Appl. No. 15/187,358.
Office action dated Mar. 18, 2014 for U.S. Appl. No. 13/219,372.
Office action dated Apr. 7, 2014 for U.S. Appl. No. 13/673,842.
Office action dated Apr. 13, 2015 for U.S. Appl. No. 13/873,059.
Office action dated Apr. 29, 2016 for U.S. Appl. No. 14/397,845.
Office Action dated May 19, 2017 for U.S. Appl. No. 15/048,703.
Office action dated Jun. 20, 2016 for U.S. Appl. No. 13/364,191.
Office action dated Jul. 16, 2012 for U.S. Appl. No. 13/007,516.
Office action dated Jul. 22, 2014 for U.S. Appl. No. 13/873,059.
Office action dated Jul. 26, 2013 for U.S. Appl. No. 13/219,372.
"Office action dated Sep. 10, 2015 for U.S. Appl. No. 13/364,191."
Office action dated Sep. 26, 2014 for U.S. Appl. No. 13/364,191.
Office action dated Sep. 27, 2016 for U.S. Appl. No. 14/397,845.
Office action dated Nov. 29, 2013 for U.S. Appl. No. 13/364,191.
Park-Chung, et al. Distinct sites for inverse modulation of N-methyl-D-aspartate receptors by sulfated steroids. Mol Pharmacol. Dec. 1997;52(6):1113-23.
Prassas, et al. Novel Therapeutic Applications of Cardiac Glycosides, Nature Reviews, Drug Discovery, vol. 7, Nov. 2008, 926-935.
Remington's Pharamceutical Sciences. 18th Edition, Mack Publishing Company (1990).
Remington: The Science and Practice of Pharmacy. 21st Edition, Lippincott Williams & Wilkins (2005).
Repke, et al. Potential suitability of Na+/K(+)-transporting ATPase in pre-screens for anti-cancer agents. Anticancer Drug Des. Mar. 1995;10(2):177-87.

(56) References Cited

OTHER PUBLICATIONS

Roche. Bioreversible Carriers in Drug Design, American Pharmaceutical Association and Pergamon Press, 1987.
Sastna, et al. Synthesis of C3, C5, and C7 pregnane derivatives and their effect on NMDA receptor responses in cultured rat hippocampal neurons. Steroids. Feb. 2009;74(2):256-63. doi: 10.1016/j.steroids.2008.11.011. Epub Nov. 24, 2008.
Shimada, et al. Utility of cyclodextrin in mobile phase for high-performance liquid chromatographic separation of bufadienolides. Journal of Liquid Chromatography. 1990;13(3):493-504.
Takanori, et al. Synthetic study of a cardiac steroid, marinoic acid. Chemical abstracts service. Database accession No. 2005:1298434. J. School Sci. Eng. 2005; 41:17-22.
Templeton, J.F., et al., "Synthesis of 4, 14-Dihydroxy-5p, 14p-pregnan-20-one C-3 Derivatives: Ozonolysis of Digitoxin and Digitoxigenin and their Derivatives followed by Zinc-Acetic Acid Reduction to the C-21 Methyl Ketone," J. Chem. Soc. Perkin Trans., 1991, vol. 1, pp. 823-829.
U.S. Appl. No. 14/397,845, filed Oct. 29, 2014.
U.S. Appl. No. 14/625,329, filed Feb. 18, 2015.
Weaver, et al. Geometry and charge determine pharmacological effects of steroids on N-methyl-D-aspartate receptor-induced Ca(2+) accumulation and cell death. J Pharmacol Exp Ther. Jun. 2000;293(3):747-54.
Co-pending U.S. Appl. No. 15/728,908, filed Oct. 10, 2017.
European search report with written opinion dated Dec. 13, 2017 for EP Application No. 17181707.
Office Action dated Nov. 27, 2017 for U.S. Appl. No. 15/285,287.
Office Action dated Nov. 28, 2017 for U.S. Appl. No. 15/048,703.
Roder et al. Archiv der Pharmazie (Weiheim, Germany) (1985), 318(12), 1115-25 STN Accession No. 1986:64919 CAPLUS.
Rutesh. Overview of pharmaceutical excipients used in tablets and capsules. Drug Topics. Oct. 24, 2008.
Office action dated Mar. 8, 2018 for U.S. Appl. No. 15/728,908.
Notice of allowance dated Jun. 15, 2018 for U.S. Appl. No. 15/048,703.
Notice of allowance dated Aug. 7, 2018 for U.S. Appl. No. 15/728,908.
Office action dated Aug. 14, 2018 for U.S. Appl. No. 15/285,287.

\* cited by examiner

CERTAIN STEROIDS AND METHODS FOR USING THE SAME IN THE TREATMENT OF CANCER

CROSS-REFERENCE

This application is a continuation of U.S. utility application Ser. No. 14/397,845, filed Oct. 29, 2014, now U.S Pat. No. 9,676,813, which is a U.S. national phase application under 35 U.S.C. § 371 of international application No. PTC/US2013/038075, filed Apr. 29, 2013, which claims priority to U.S. provisional application No. 61/639,930, filed Apr. 29, 2012, each of which is incorporated herein by reference for all purposes.

BACKGROUND

Cancer can be viewed as a breakdown in the communication between tumor cells and their environment, including their normal neighboring cells. Signals, both growth-stimulatory and growth-inhibitory, are routinely exchanged between cells within a tissue. Normally, cells do not divide in the absence of stimulatory signals, and likewise, will cease dividing in the presence of inhibitory signals. In a cancerous, or neoplastic state, a cell acquires the ability to "override" these signals and to proliferate under conditions in which normal cells would not grow.

Cardiotonic steroids like digoxin and digitoxin are a class of naturally derived compounds that bind to and inhibit $Na^+/K^+$-ATPase (sodium pump). Members of this family have been used for the treatment of heart failure and arrhythmia for many years. Recent findings have revealed that these compounds may be involved in the regulation of several important cellular processes. Several cardiotonic steroids such as digitoxin and oleandrin have shown inhibitory effect on the growth of human tumor cells.

SUMMARY OF THE INVENTION

In an aspect, the invention provides least one chemical entity chosen from compounds of Formula I

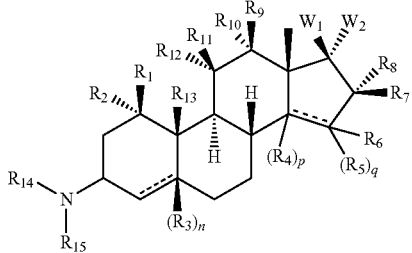

Formula I and pharmaceutically acceptable salts thereof, wherein $R_1$, $R_2$, $R_3$, $R_4$, $R_5$, $R_6$, $R_9$, $R_{10}$, $R_{11}$ and $R_{12}$ are independently chosen from hydrogen, hydroxy, optionally substituted alkyl, optionally substituted cycloalkyl, optionally substituted alkenyl, optionally substituted alkynyl, optionally substituted alkoxy, optionally substituted aryloxy, optionally substituted heteroaryloxy, optionally substituted heterocycloalkyloxy, optionally substituted aminocarbonyloxy, optionally substituted aryloxy, optionally substituted alkoxycarbonyloxy, and optionally substituted amino; or $R_1$ and $R_2$, or $R_5$ and $R_6$, or $R_7$ and $R_8$, or $R_9$ and $R_{10}$, or $R_{11}$ and $R_{12}$ mutually independently, together in each case denote an oxo group (=O); or $R_4$ and $R_5$ may optionally be joined together with any intervening atoms to form an optionally substituted heterocycloalkyl ring;

$R_7$ is chosen from hydrogen, hydroxy, optionally substituted alkoxy, optionally substituted aryloxy, optionally substituted heteroaryloxy, optionally substituted heterocycloalkyloxy, optionally substituted aminocarbonyloxy, optionally substituted acyloxy, optionally substituted alkoxycarbonyloxy, and optionally substituted amino;

$R_8$ is chosen from hydrogen, optionally substituted alkyl, optionally substituted cycloalkyl, optionally substituted alkenyl, and optionally substituted alkynyl;

$R_{13}$ is chosen from hydrogen, optionally substituted alkyl, and formyl;

$R_{14}$ is chosen from hydrogen, optionally substituted alkyl, optionally substituted cycloalkyl, optionally substituted heterocycloalkyl, optionally substituted aryl, and optionally substituted heteroaryl; and $R_{15}$ is chosen from hydrogen, hydroxyl, formyl, optionally substituted alkoxy, optionally substituted alkyl, optionally substituted cycloalkyl, optionally substituted heterocycloalkyl, optionally substituted aryl, and optionally substituted heteroaryl, —$COR_{16}$, —$CO_2R_{16}$, —$CONR_{17}R_{18}$, —$C(NR_{19})NR_{17}R_{18}$, —$C(NCN)NR_{17}R_{18}$, —$SO_2R_{16}$, and —$SO_2NR_{17}R_{18}$, where $R_{16}$ is chosen from optionally substituted alkyl, optionally substituted cycloalkyl, optionally substituted heterocycloalkyl, optionally substituted aryl, and optionally substituted heteroaryl; and $R_{17}$, $R_{18}$ and $R_{19}$ are independently chosen from hydrogen, optionally substituted alkyl, optionally substituted cycloalkyl, optionally substituted heterocycloalkyl, optionally substituted aryl, and optionally substituted heteroaryl; or $R_{17}$ and $R_{18}$ may be joined together with any intervening atoms to form an optionally substituted heterocycloalkyl ring; or $R_{14}$ and $R_{15}$ are joined together with any intervening atoms to form an optionally substituted 4- to 8-membered heterocycloalkyl or optionally substituted 5- to 8-membered heteroaryl ring;

$W_1$ is chosen from the following moieties:

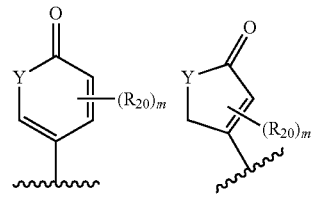

wherein Y is chosen from O and $NR_{21}$;

$R_{20}$ is chosen from cyano, halo, hydroxy, azido, nitro, carboxy, sulfinyl, sulfanyl, optionally substituted alkoxy, optionally substituted aryloxy, optionally substituted heteroaryloxy, optionally substituted heterocycloalkyloxy, optionally substituted alkoxycarbonyl, optionally substituted alkyl, optionally substituted alkenyl, optionally substituted aryloxy, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, optionally substituted carbaminodoyl, and
optionally substituted alkynyl;

$R_{21}$ is chosen from hydrogen, optionally substituted alkyl,
optionally substituted cycloalkyl, optionally substituted
heterocycloalkyl, optionally substituted aryl, and optionally substituted heteroaryl;

$W_2$ is chosen from hydrogen, optionally substituted alkyl,
optionally substituted cycloalkyl, optionally substituted
alkenyl, and optionally substituted alkynyl;

m is selected from 0, 1, 2, and 3;

n, p, and q is independently selected from 0 and 1; and the dotted line represents a single bond or a double bond.

In some embodiments, $R_1$, $R_2$, $R_3$, $R_4$, $R_5$, $R_6$, $R_9$, $R_{10}$, $R_{11}$ and $R_{12}$ are independently chosen from hydrogen, hydroxy, optionally substituted alkyl, optionally substituted alkoxy, optionally substituted aminocarbonyloxy, optionally substituted acyloxy, optionally substituted alkoxycarbonyloxy, and optionally substituted amino. In some cases, $R_1$, $R_2$, $R_3$, $R_4$, $R_5$, $R_6$, $R_9$, $R_{10}$, $R_{11}$ and $R_{12}$ are independently chosen from hydrogen, hydroxy, and optionally substituted alkyl. For example, $R_1$, $R_2$, $R_3$, $R_4$, $R_5$, $R_6$, $R_9$, $R_{10}$, $R_{11}$ and $R_{12}$ are independently chosen from hydrogen, hydroxy, and methyl. In some cases, $R_4$ is hydroxy.

In some embodiments, the invention provides a compound of Formula I, wherein $R_4$ and $R_5$ are joined together with any intervening atoms to form an optionally substituted 3- to 8-membered heterocycloalkyl ring. For example, $R_4$ and $R_5$ are joined together with any intervening atoms to form an oxirane ring.

In some embodiments, $R_7$ is chosen from hydrogen, hydroxy, optionally substituted alkoxy, optionally substituted aminocarbonyloxy, optionally substituted acyloxy, optionally substituted alkoxycarbonyloxy, and optionally substituted amino. In some cases, $R_7$ is chosen from hydrogen and optionally substituted acyloxy. For example, $R_7$ is chosen from hydrogen and —$OCOCH_3$.

In some embodiments, $R_8$ and $W_2$ are independently chosen from hydrogen and optionally substituted alkyl.

In some embodiments, $R_{13}$ is chosen from hydrogen and optionally substituted alkyl. In some cases, $R_{13}$ is chosen from hydrogen and optionally substituted alkyl. For example, $R_{13}$ is chosen from hydrogen, methyl, and hydroxymethyl.

In some embodiments, Y is chosen from O, NH and $NCH_3$. For example Y is O.

In some embodiments, $R_{20}$ is chosen from cyano, halo, hydroxy, carboxy, sufonyl, optionally substituted alkoxy, optionally substituted alkoxycarbonyl, optionally substituted alkyl, optionally substituted amino, optionally substituted acyl, optionally substituted alkoxycarbonyl, optionally substituted aminocarbonyl, and optionally substituted aminosulfonyl.

In some examples, m is 0.

In some cases, the dotted line represents a single bond. In some examples, the dotted line represents a double bond.

In some embodiments, the compound of Formula I has the formula:

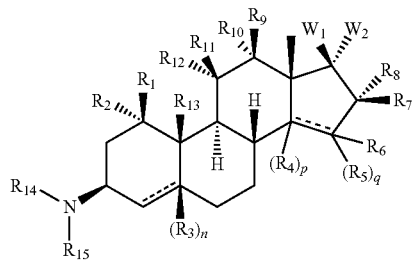

In other embodiments, the compound of Formula I has the formula:

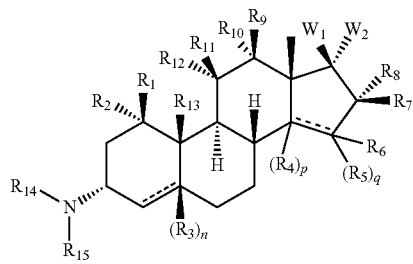

In some embodiments, the compound of Formula I is chosen from compounds of Formula Ia.

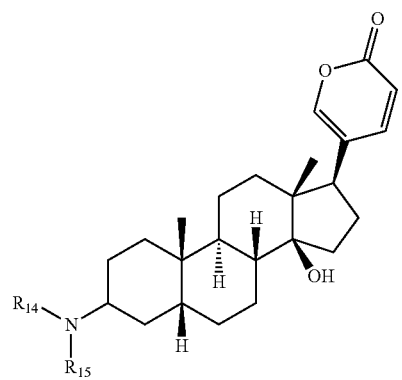

Formula Ia

In some embodiments, the compound of Formula I is chosen from compounds of Formula Ib.

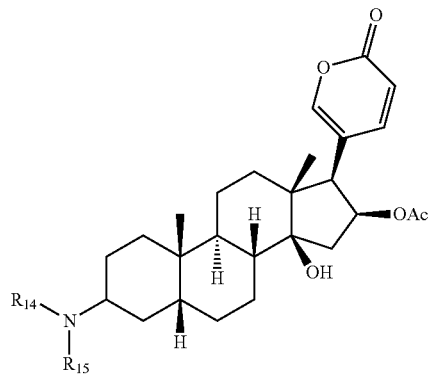

Formula Ib

In some embodiments, the compound of Formula I is chosen from compounds of Formula Ic.

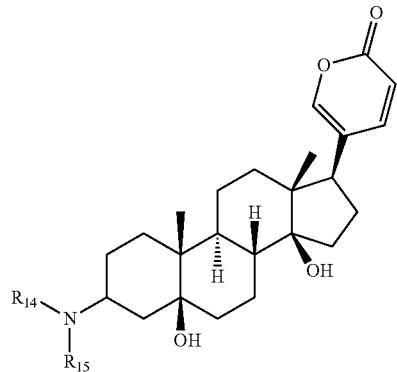

Formula Ic

In some embodiments, the compound of Formula I is chosen from compounds of Formula Id.

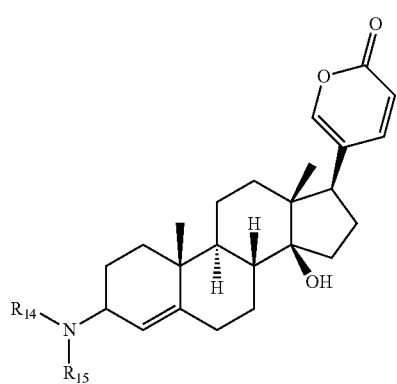

Formula Id

In some embodiments, the compound of Formula I is chosen from compounds of Formula Ie.

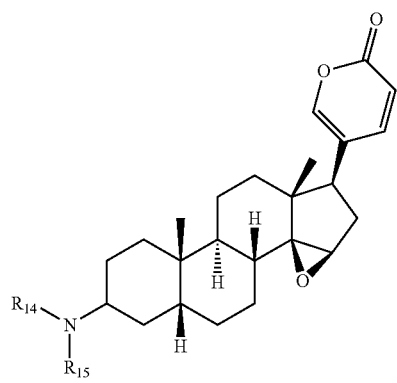

Formula Ie

In some embodiments, the compound of Formula I is chosen from compounds of Formula If.

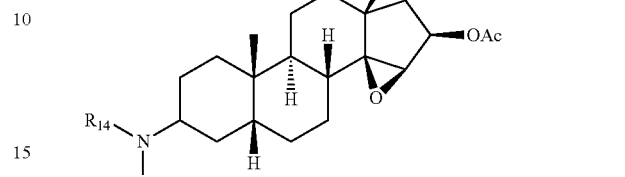

Formula If

In some embodiments, the compound of Formula I is chosen from compounds of Formula Ig.

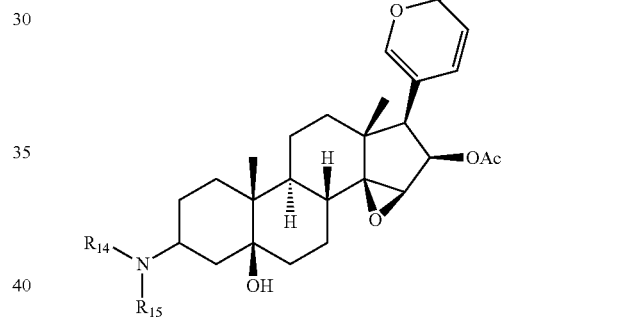

Formula Ig

In some embodiments, the compound of Formula I is chosen from compounds of Formula Ih.

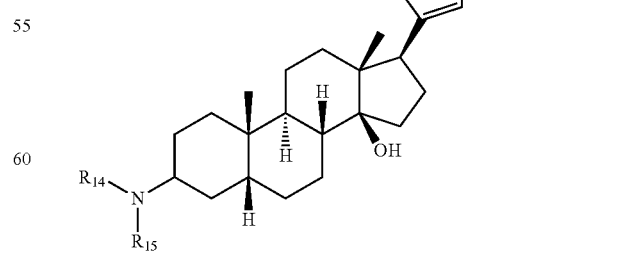

Formula Ih

In some embodiments, the compound of Formula I is chosen from compounds of Formula Ii.

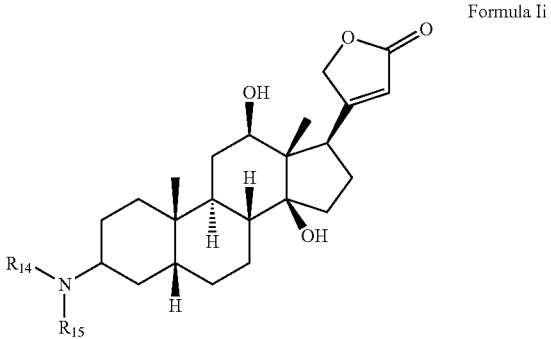

Formula Ii

In some embodiments, the compound of Formula I is chosen from compounds of Formula Ij.

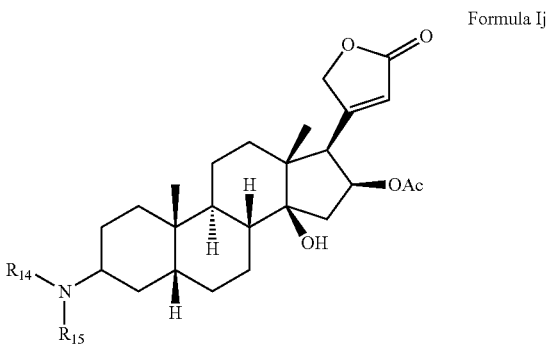

Formula Ij

In some embodiments, the compound of Formula I is chosen from compounds of Formula Ik.

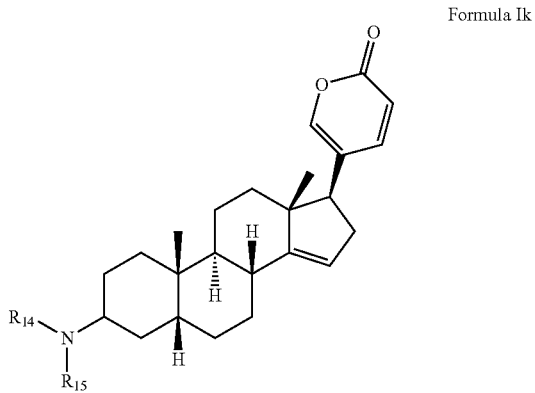

Formula Ik

In some embodiments, the compound of Formula I is chosen from compounds of Formula Il.

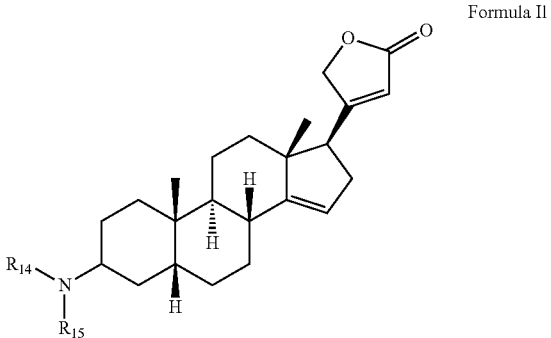

Formula Il

In some embodiments, the $R_{14}$ in Formula I (Ia-Il) is chosen from hydrogen, optionally substituted lower alkyl, optionally substituted cycloalkyl, optionally substituted heterocycloalkyl, optionally substituted aryl, and optionally substituted heteroaryl. In some cases, $R_{14}$ is chosen from hydrogen and optionally substituted lower alkyl. For example, $R_{14}$ is hydrogen. In some cases $R_{14}$ is not hydrogen. For example, $R_{14}$ is optionally substituted alkyl, optionally substituted cycloalkyl, or optionally substituted heterocycloalkyl.

In some embodiments, the $R_{15}$ in Formula I (Ia-Il) is chosen from hydrogen, optionally substituted alkyl, optionally substituted cycloalkyl, optionally substituted heterocycloalkyl, —$COR_{16}$, —$CO_2R_{16}$, —$CONR_{17}R_{18}$, —$C(NR_{19})NR_{17}R_{18}$, —$C(NCN)NR_{17}R_{18}$, —$SO_2R_{16}$, and —$SO_2NR_{17}R_{18}$. In some cases, $R_{15}$ is chosen from —$COR_{16}$, —$CO_2R_{16}$, —$CONR_{17}R_{18}$, and —$SO_2NR_{17}R_{18}$. For example, $R_{15}$ is chosen from —$COR_{16}$, —$CO_2R_{16}$, and —$CONR_{17}R_{18}$.

In some embodiments, $R_{14}$ and $R_{15}$ are not hydrogen. In some embodiments, $R_{14}$ is optionally substituted alkyl, optionally substituted cycloalkyl, or optionally substituted heterocycloalkyl. In other embodiments, $R_{15}$ is —$CO_2R_{16}$, —$CONR_{17}R_{18}$, —$C(NR_{19})NR_{17}R_{18}$, —$C(NCN)NR_{17}R_{18}$, —$SO_2R_{16}$, and —$SO_2NR_{17}R_{18}$. In some embodiments, $R_{15}$ is $SO_2R_{16}$, —$COR_{16}$, or —$CO_2R_{16}$.

In some embodiments, $R_{14}$ and $R_{15}$ are joined together with any intervening atoms to form an optionally substituted 4- to 8-membered heterocycloalkyl or or optionally substituted 5- to 8-membered heteroaryl ring. For example, $R_{14}$ and $R_{15}$ form an optionally substituted 5- or 6-membered heterocycloalkyl ring. The 5- or 6-membered heterocycloalkyl ring may be, for example, a morpholino, piperazino, or pyrrolidino group.

In some embodiments, $R_{16}$ is chosen from optionally substituted alkyl, optionally substituted cycloalkyl, optionally substituted heterocycloalkyl, optionally substituted aryl, and optionally substituted heteroaryl; $R_{17}$ and $R_{18}$ are independently chosen from hydrogen, optionally substituted alkyl, optionally substituted cycloalkyl, optionally substituted heterocycloalkyl, optionally substituted aryl, and optionally substituted heteroaryl; and $R_{19}$ is chosen from hydrogen, optionally substituted alkyl, optionally substituted cycloalkyl, and optionally substituted heterocycloalkyl. For example, $R_{16}$ is chosen from optionally substituted alkyl, optionally substituted cycloalkyl, and optionally substituted heterocycloalkyl; $R_{17}$ and $R_{18}$ are independently chosen from hydrogen, optionally substituted alkyl, optionally substituted cycloalkyl, and optionally substituted heterocycloalkyl; and $R_{19}$ is chosen from hydrogen and optionally substituted alkyl.

In some embodiments $R_{17}$ and $R_{18}$ may be joined together with any intervening atoms to form an optionally substituted 4- to 8-membered heterocycloalkyl ring. In some cases, $R_{17}$ and $R_{18}$ are joined together to form a 4- to 8-membered heterocycloalkyl ring optionally substituted with one or two groups independently chosen from amino, hydroxyl, oxo, and lower alkyl. For example, $R_{17}$ and $R_{18}$ is joined together to form a 5- to 7-membered heterocycloalkyl ring chosen from 3-hydroxypyrrolidine-1-yl, 3-aminopyrrolidine-1-yl, 3-oxopiperazine-1-yl, 4-methyl-1,4-diazepane-1-yl, 1,4-diazepane-1-yl, piperazine-1-yl, 4-methylpiperazine-1-yl, and morpholine-4-yl.

In some embodiments, $R_{14}$ and $R_{15}$ are joined together with any intervening atoms to form an optionally substituted 4- to 8-membered heterocycloalkyl ring.

In another aspect, the invention provides a pharmaceutical composition comprising a pharmaceutically acceptable carrier and at least one chemical entity of Formula I (Ia-Il). The pharmaceutical composition of the invention may be formulated in a form of tablets, capsules, powders, liquids, suspensions, suppositories, or aerosols. The invention also provides packaged pharmaceutical compositions comprising a pharmaceutical composition of the invention and instructions for using the composition to treat a subject suffering from cancer.

In another aspect, the invention provides a method of treating cancer in a subject. The methods of the invention comprise administering to a subject in need thereof a therapeutically effective amount of at least one chemical entity of the invention (Formula I (Ia-Il)).

DETAILED DESCRIPTION OF THE INVENTION

Provided are certain chemical entities and compositions thereof that may be useful in the treatment of cancer.

Provided is at least one chemical entity chosen from compounds of Formula I

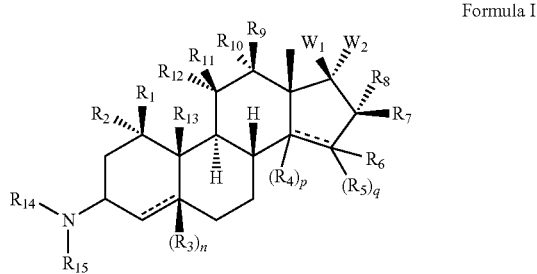

Formula I and pharmaceutically acceptable salts thereof, wherein $R_1$, $R_2$, $R_3$, $R_4$, $R_5$, $R_6$, $R_9$, $R_{10}$, $R_{11}$ and $R_{12}$ are independently chosen from hydrogen, hydroxy, optionally substituted alkyl, optionally substituted cycloalkyl, optionally substituted alkenyl, optionally substituted alkynyl, optionally substituted alkoxy, optionally substituted aryloxy, optionally substituted heteroaryloxy, optionally substituted heterocycloalkyloxy, optionally substituted aminocarbonyloxy, optionally substituted acyloxy, optionally substituted alkoxycarbonyloxy, and optionally substituted amino; or $R_1$ and $R_2$, or $R_5$ and $R_6$, or $R_7$ and $R_8$, or $R_9$ and $R_{10}$, or $R_{11}$ and $R_{12}$ mutually independently, together in each case denote an oxo group (=O); or $R_4$ and $R_5$ may optionally be joined together with any intervening atoms to form an optionally substituted heterocycloalkyl ring;

$R_7$ is chosen from hydrogen, hydroxy, optionally substituted alkoxy, optionally substituted aryloxy, optionally substituted heteroaryloxy, optionally substituted heterocycloalkyloxy, optionally substituted aminocarbonyloxy, optionally substituted acyloxy, optionally substituted alkoxycarbonyloxy, and optionally substituted amino;

$R_8$ is chosen from hydrogen, optionally substituted alkyl, optionally substituted cycloalkyl, optionally substituted alkenyl, and optionally substituted alkynyl;

$R_{13}$ is chosen from hydrogen, optionally substituted alkyl, and formyl;

$R_{14}$ is chosen from hydrogen, optionally substituted alkyl, optionally substituted cycloalkyl, optionally substituted heterocycloalkyl, optionally substituted aryl, and optionally substituted heteroaryl; and $R_{15}$ is chosen from hydrogen, hydroxyl, formyl, optionally substituted alkoxy, optionally substituted alkyl, optionally substituted cycloalkyl, optionally substituted heterocycloalkyl, optionally substituted aryl, and optionally substituted heteroaryl, $-COR_{16}$, $-CO_2R_{16}$, $-CONR_{17}R_{18}$, $-C(NR_{19})NR_{17}R_{18}$, $-C(NCN)NR_{17}R_{18}$, $-SO_2R_{16}$, and $-SO_2NR_{17}R_{18}$, where $R_{16}$ is chosen from optionally substituted alkyl, optionally substituted cycloalkyl, optionally substituted heterocycloalkyl, optionally substituted aryl, and optionally substituted heteroaryl; and $R_{17}$, $R_{18}$ and $R_{19}$ are independently chosen from hydrogen, optionally substituted alkyl, optionally substituted cycloalkyl, optionally substituted heterocycloalkyl, optionally substituted aryl, and optionally substituted heteroaryl; or $R_{17}$ and $R_{18}$ may be joined together with any intervening atoms to form an optionally substituted heterocycloalkyl ring, or $R_{14}$ and $R_{15}$ are joined together with any intervening atoms to form an optionally substituted 4- to 8-membered heterocycloalkyl or or optionally substituted 5- to 8-membered heteroaryl ring;

$W_1$ is chosen from the following moieties:

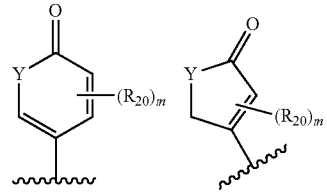

wherein Y is chosen from O and $NR_{21}$;

$R_{20}$ is chosen from cyano, halo, hydroxy, azido, nitro, carboxy, sulfinyl, sulfanyl, optionally substituted alkoxy, optionally substituted aryloxy, optionally substituted heteroaryloxy, optionally substituted heterocycloalkyloxy, optionally substituted alkoxycarbonyl, optionally substituted alkyl, optionally substituted alkenyl, optionally substituted aryloxy, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, optionally substituted carbaminodoyl, and optionally substituted alkynyl;

$R_{21}$ is chosen from hydrogen, optionally substituted alkyl, optionally substituted cycloalkyl, optionally substituted heterocycloalkyl, optionally substituted aryl, and optionally substituted heteroaryl;

$W_2$ is chosen from hydrogen, optionally substituted alkyl, optionally substituted cycloalkyl, optionally substituted alkenyl, and optionally substituted alkynyl;

m is selected from 0, 1, 2, and 3;

n, p, and q is independently selected from 0 and 1; and the dotted line represents a single bond or a double bond.

Also provided is a pharmaceutical composition comprising a pharmaceutically acceptable carrier and at least one chemical entity described herein.

Also provided is a packaged pharmaceutical composition comprising a pharmaceutical composition described herein and instructions for using the composition to treat a subject suffering from cancer.

Also provided is a method of treating cancer in a subject which comprises administering to a subject in need thereof a therapeutically effective amount of at least one chemical entity described herein.

As used herein, the following words and phrases are generally intended to have the meanings as set forth below, except to the extent that the context in which they are used indicates otherwise.

The following abbreviations and terms have the indicated meanings throughout:

AcOH=acetic acid
Boc=tert-butoxycarbonyl
c-=cyclo
DCC=dicyclohexylcarbodiimide
DCM=dichloromethane
DIEA=N,N-diisopropylethylamine
DMAP=4-dimethylaminopyridine
EDC=1-ethyl-3-(3-dimethylaminopropyl) carbodiimide
eq=equivalent(s)
Et=ethyl
EtOAc or EA=ethyl acetate
EtOH=ethanol
g=gram
h or hr=hour
HBTU=O-(benzotriazol-1-yl)-N,N,N',N'-tetramethyluronium hexafluorophosphate
HOBt=hydroxybenzotriazole
HPLC=high pressure liquid chromatography
i-=iso
kg or Kg=kilogram
L or l=liter
LC/MS=LCMS=liquid chromatography-mass spectrometry
LRMS=low resolution mass spectrometry
m/z=mass-to-charge ratio
Me=methyl
MeOH=methanol
mg=milligram
min=minute
mL=milliliter
mmol=millimole
n-=normal
NaOAc=sodium acetate
PE=petroleum ether
Ph=phenyl
Prep=preparative
quant.=quantitative
RP-HPLC=reverse phase-high pressure liquid chromatography
rt or RT=room temperature
s-=sec-=secondary
t-=tert-=tertiary
THF=tetrahydrofuran
TLC=thin layer chromatography
UV=ultraviolet As used herein, when any variable occurs more than one time in a chemical formula, its definition on each occurrence is independent of its definition at every other occurrence.

As used herein, a dash ("-") that is not between two letters or symbols is used to indicate a point of attachment for a substituent. For example, —CONH$_2$ is attached through the carbon atom.

As used herein, "optional" or "optionally" is meant that the subsequently described event or circumstance may or may not occur, and that the description includes instances wherein the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, "alkyl" refers to straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. When an alkyl residue having a specific number of carbons is named, all branched and straight chain versions having that number of carbons are intended to be encompassed; thus, for example, "butyl" is meant to include n-butyl, sec-butyl, isobutyl and t-butyl; "propyl" includes n-propyl and isopropyl. "Lower alkyl" refers to alkyl groups having one to six carbons. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is a subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_0$ alkylene indicates a covalent bond and $C_1$ alkylene is a methylene group.

As used herein, "alkenyl" refers to an unsaturated branched or straight-chain alkyl group having at least one carbon-carbon double bond derived by the removal of one molecule of hydrogen from adjacent carbon atoms of the parent alkyl. The group may be in either the cis or trans configuration about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl; and the like. In certain embodiments, an alkenyl group has from 2 to 20 carbon atoms and in other embodiments, from 2 to 6 carbon atoms. "Lower alkenyl" refers to alkenyl groups having two to six carbons.

As used herein, "alkynyl" refers to an unsaturated branched or straight-chain alkyl group having at least one carbon-carbon triple bond derived by the removal of two molecules of hydrogen from adjacent carbon atoms of the parent alkyl. Typical alkynyl groups include, but are not limited to, ethynyl; propynyls such as prop-1-yn-1-yl, prop-2-yn-1-yl; butynyls such as but-1-yn-1-yl, but-1-yn-3-yl, but-3-yn-1-yl; and the like. In certain embodiments, an alkynyl group has from 2 to 20 carbon atoms and in other embodiments, from 3 to 6 carbon atoms. "Lower alkynyl" refers to alkynyl groups having two to six carbons.

As used herein, "cycloalkyl" refers to a non-aromatic carbocyclic ring, usually having from 3 to 8 ring carbon atoms. The ring may be saturated or have one or more carbon-carbon double bonds. Examples of cycloalkyl groups include cyclopropyl, cyclobutyl, cyclopentyl, cyclopentenyl, cyclohexyl, and cyclohexenyl, as well as bridged and caged ring groups such as norbornane.

As used herein, "alkoxy" refers to an alkyl group of the indicated number of carbon atoms attached through an oxygen bridge such as, for example, methoxy, ethoxy, propoxy, isopropoxy, n-butoxy, sec-butoxy, tert-butoxy, pentyloxy, 2-pentyloxy, isopentyloxy, neopentyloxy, hexyloxy, 2-hexyloxy, 3-hexyloxy, 3-methylpentyloxy, and the like. Alkoxy groups will usually have from 1 to 7 carbon atoms attached through the oxygen bridge. "Lower alkoxy" refers to alkoxy groups having one to six carbons.

As used herein, "acyl" refers to the groups H—C(O)—; (alkyl)-C(O)—; (cycloalkyl)-C(O)—; (aryl)-C(O)—; (heteroaryl)-C(O)—; and (heterocycloalkyl)-C(O)—, wherein the group is attached to the parent structure through the carbonyl functionality and wherein alkyl, cycloalkyl, aryl, heteroaryl, and heterocycloalkyl are as described herein. Acyl groups have the indicated number of carbon atoms, with the carbon of the keto group being included in the numbered carbon atoms. For example a $C_2$ acyl group is an acetyl group having the formula $CH_3(C=O)—$.

As used herein, "formyl" refers to the group —C(O)H.

As used herein, "alkoxycarbonyl" refers to a group of the formula (alkoxy)(C=O)— attached through the carbonyl carbon wherein the alkoxy group has the indicated number of carbon atoms. Thus a $C_1$-$C_6$ alkoxycarbonyl group is an alkoxy group having from 1 to 6 carbon atoms attached through its oxygen to a carbonyl linker.

As used herein, "azido" refers to the group —$N_3$.

As used herein, "amino" refers to the group —$NH_2$.

As used herein, "mono- and di-(alkyl)amino" refers to secondary and tertiary alkyl amino groups, wherein the alkyl groups arc as defined above and have the indicated number of carbon atoms. The point of attachment of the alkylamino group is on the nitrogen. Examples of mono- and di-alkylamino groups include ethylamino, dimethylamino, and methyl-propyl-amino.

As used herein, "aminocarbonyl" refers to the group —$CONR^bR^c$, where $R^b$ is chosen from H, optionally substituted $C_1$-$C_6$ alkyl, optionally substituted cycloalkyl, optionally substituted heterocycloalkyl, optionally substituted aryl, and optionally substituted heteroaryl, optionally substituted alkoxy; and $R^c$ is chosen from hydrogen and optionally substituted $C_1$-$C_4$ alkyl; or $R^b$ and $R^c$ taken together with the nitrogen to which they are bound, form an optionally substituted 5- to 8-membered nitrogen-containing heterocycloalkyl which optionally includes 1 or 2 additional heteroatoms chosen from O, N, and S in the heterocycloalkyl ring;

where each substituted group is independently substituted with one or more substituents independently chosen from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for cycloalkyl, heterocycloalkyl, or heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), and —$NHSO_2$($C_1$-$C_4$ haloalkyl).

As used herein, "aryl" refers to: 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene.

For example, aryl includes 6-membered carbocyclic aromatic rings fused to a 5- to 7-membered heterocycloalkyl ring containing 1 or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g. a naphthyl group with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

As used herein, "aryloxy" refers to the group —O-aryl.

As used herein, "aralkyl" refers to the group -alkyl-aryl.

As used herein, "carbamimidoyl" refers to the group —C(=NH)—NH2.

As used herein, "substituted carbamimidoyl" refers to the group —C(=$NR^e$)—$NR^fR^g$ where $R^e$ is chosen from hydrogen, cyano, optionally substituted alkyl, optionally substituted cycloalkyl, optionally substituted aryl, optionally substituted heteroaryl, and optionally substituted heterocycloalkyl; and $R^f$ and $R^g$ are independently chosen from hydrogen optionally substituted alkyl, optionally substituted cycloalkyl, optionally substituted aryl, optionally substituted heteroaryl, and optionally substituted heterocycloalkyl, provided that at least one of $R^e$, $R^f$, and $R^g$ is not hydrogen and wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently chosen from —$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substituent for cycloalkyl, heterocycloalkyl, and heteroaryl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —OP(O)($OR^b$)$OR^c$, sulfanyl (such as $SR^b$), sulfinyl (such as —$SOR^a$), and sulfonyl (such as —$SO_2R^a$ and —$SO_2NR^bR^c$), where $R^a$ is chosen from optionally substituted C1-C6 alkyl, optionally substituted aryl, and optionally substituted heteroaryl;

$R^b$ is chosen from H, optionally substituted C1-C6 alkyl, optionally substituted aryl, and optionally substituted heteroaryl; and $R^c$ is chosen from hydrogen and optionally substituted C1-C4 alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently chosen from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH(C$_1$-C$_4$ alkylphenyl), cyano, nitro, oxo (as a substituent for cycloalkyl, heterocycloalkyl, or heteroaryl), —CO$_2$H, —C(O)OC$_1$-C$_4$ alkyl, —CON(C$_1$-C$_4$ alkyl)(C$_1$-C$_4$ alkyl), —CONH(C$_1$-C$_4$ alkyl), —CONH$_2$, —NHC(O)(C$_1$-C$_4$ alkyl), —NHC(O)(phenyl), —N(C$_1$-C$_4$ alkyl)C(O)(C$_1$-C$_4$ alkyl), —N(C$_1$-C$_4$ alkyl)C(O)(phenyl), —C(O)C$_1$-C$_4$ alkyl, —C(O)C$_1$-C$_4$ phenyl, —C(O)C$_1$-C$_4$ haloalkyl, —OC(O)C$_1$-C$_4$ alkyl, —SO$_2$(C$_1$-C$_4$ alkyl), —SO$_2$(phenyl), —SO$_2$(C$_1$-C$_4$ haloalkyl), —SO$_2$NH$_2$, —SO$_2$NH(C$_1$-C$_4$ alkyl), —SO$_2$NH(phenyl), —NHSO$_2$(C$_1$-C$_4$ alkyl), —NHSO$_2$(phenyl), and —NHSO$_2$(C$_1$-C$_4$ haloalkyl).

As used herein, "halo" refers to fluoro, chloro, bromo, and iodo, and the term "halogen" includes fluorine, chlorine, bromine, and iodine.

As used herein, "haloalkyl" refers to alkyl as defined above having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl.

As used herein, "heteroaryl" refers to:

5- to 7-membered aromatic, monocyclic rings containing one or more, for example, from 1 to 4, or in certain embodiments, from 1 to 3, heteroatoms chosen from N, O, and S, with the remaining ring atoms being carbon;

bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring; and tricyclic heterocycloalkyl rings containing one or more, for example, from 1 to 5, or in certain embodiments, from 1 to 4, heteroatoms chosen from N, O, and S, with the remaining ring atoms being carbon and wherein at least one heteroatom is present in an aromatic ring.

For example, heteroaryl includes a 5- to 7-membered heterocycloalkyl, aromatic ring fused to a 5- to 7-membered cycloalkyl or heterocycloalkyl ring. For such fused, bicyclic heteroaryl ring systems wherein only one of the rings contains one or more heteroatoms, the point of attachment may be at either ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolyl, isoxazolyl, oxazolyl, thiazolyl, thiadiazolyl, tetrazolyl, thienyl, benzothiophenyl, furanyl, pyrrolyl, benzofuranyl, benzoimidazolyl, indolyl, pyridazinyl, triazolyl, quinolinyl, quinoxalinyl, pyrazolyl, and 5,6,7,8-tetrahydroisoquinolinyl. Bivalent radicals derived from univalent heteroaryl radicals whose names end in "-yl" by removal of one hydrogen atom from the atom with the free valence are named by adding "-idene" to the name of the corresponding univalent radical, e.g. a pyridyl group with two points of attachment is a pyridylidene. Heteroaryl does not encompass or overlap with aryl, cycloalkyl, or heterocycloalkyl, as defined herein Substituted heteroaryl also includes ring systems substituted with one or more oxide (—O$^-$) substituents, such as pyridinyl N-oxides.

As used herein, "heterocycloalkyl" refers to a single, non-aromatic ring, usually with 3 to 8 ring atoms, containing at least 2 carbon atoms in addition to 1-3 heteroatoms independently chosen from oxygen, sulfur, and nitrogen, as well as combinations comprising at least one of the foregoing heteroatoms. The ring may be saturated or have one or more carbon-carbon double bonds. Suitable heterocycloalkyl groups include, for example (as numbered from the linkage position assigned priority 1), 2-pyrrolidinyl, 2,4-imidazolidinyl, 2,3-pyrazolidinyl, 2-piperidyl, 3-piperidyl, 4-piperidyl, 2,5-piperazinyl, pyrrolidinyl, azetidinyl, pyranyl, 2,3-dihydrofuranyl, or 2,5-dihydrofuranyl. Morpholinyl groups are also contemplated, including 2-morpholinyl and 3-morpholinyl (numbered wherein the oxygen is assigned priority 1). Substituted heterocycloalkyl also includes ring systems substituted with one or more oxo (=O) or oxide (—O$^-$) substituents, such as piperidinyl N-oxide, morpholinyl-N-oxide, 1-oxo-1-thiomorpholinyl and 1,1-dioxo-1-thiomorpholinyl.

"Heterocycloalkyl" also includes bicyclic ring systems wherein one non-aromatic ring, usually with 3 to 8 ring atoms, contains at least 2 carbon atoms in addition to 1-3 heteroatoms independently chosen from oxygen, sulfur, and nitrogen, as well as combinations comprising at least one of the foregoing heteroatoms; and the other ring, usually with 3 to 8 ring atoms, optionally contains 1-3 heteratoms independently chosen from oxygen, sulfur, and nitrogen and is not aromatic.

As used herein, "sulfanyl" refers to the groups: —S-(optionally substituted (C$_1$-C$_6$)alkyl), —S-(optionally substituted aryl), —S-(optionally substituted heteroaryl), and —S-(optionally substituted heterocycloalkyl). Hence, sulfanyl includes the group C$_1$-C$_6$ alkylsulfanyl.

As used herein, "sulfinyl" refers to the groups: —S(O)-(optionally substituted (C$_1$-C$_6$)alkyl), —S(O)-optionally substituted aryl), —S(O)-optionally substituted heteroaryl), —S(O)-(optionally substituted heterocycloalkyl); and —S(O)-(optionally substituted amino).

As used herein, "sulfonyl" refers to the groups: —S(O$_2$)-(optionally substituted (C$_1$-C$_6$)alkyl), —S(O$_2$)-optionally substituted aryl), —S(O$_2$)-optionally substituted heteroaryl), —S(O$_2$)-(optionally substituted heterocycloalkyl), and —S(O$_2$)-(optionally substituted amino).

As used herein, "substituted" refers to any one or more hydrogens on the designated atom or group is replaced with a selection from the indicated group, provided that the designated atom's normal valence is not exceeded. When a substituent is oxo (i.e. =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

As used herein, the terms "substituted" alkyl, cycloalkyl, aryl, heterocycloalkyl, and heteroaryl, unless otherwise expressly defined, refer respectively to alkyl, cycloalkyl, aryl, heterocycloalkyl, and heteroaryl wherein one or more (such as up to 5, for example, up to 3) hydrogen atoms are replaced by a substituent independently chosen from R$^a$, —OR$^b$, optionally substituted amino (including —NR$^c$COR$^b$, —NR$^c$CO$_2$R$^a$, —NR$^c$CONR$^b$R$^c$, —NR$^b$C ($NR^c$)$NR^bR^c$, —$NR^bC(NCN)NR^bR^c$, and —$NR^cSO_2R^a$), halo, cyano, azido, nitro, oxo (as a substituent for cycloalkyl or heterocycloalkyl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —$OP(O)(OR)OR^c$, sulfanyl (such as $SR^b$), sulfinyl (such as —$SOR^a$), and sulfonyl (such as —$SO_2R^a$ and —$SO_2NR^bR^c$), where $R^a$ is chosen from optionally substituted $C_1$-$C_6$ alkyl, optionally substituted cycloalkyl, optionally substituted heterocycloalkyl, optionally substituted alkenyl, optionally substituted alkynyl, optionally substituted aryl, and optionally substituted heteroaryl; $R^b$ is chosen from hydrogen, optionally substituted $C_1$-$C_6$ alkyl, optionally substituted cycloalkyl, optionally substituted heterocycloalkyl, optionally substituted aryl, and optionally substituted heteroaryl; and $R^c$ is chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently chosen from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substituent for cycloalkyl or heterocycloalkyl), —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)(C_1$-$C_4$ alkyl), —$NHC(O)$(phenyl), —$N(C_1$-$C_4$ alkyl)$C(O)(C_1$-$C_4$ alkyl), —$N(C_1$-$C_4$ alkyl)$C(O)$(phenyl), —$C(O)C_1$-$C_4$ alkyl, —$C(O)C_1$-$C_4$ alkylphenyl, —$C(O)C_1$-$C_4$ haloalkyl, —$OC(O)C_1$-$C_4$ alkyl, —$SO_2(C_1$-$C_4$ alkyl), —$SO_2$(phenyl), —$SO_2(C_1$-$C_4$ haloalkyl), —$SO_2NH_2$, —$SO_2NH(C_1$-$C_4$ alkyl), —$SO_2NH$(phenyl), —$NHSO_2(C_1$-$C_4$ alkyl), —$NHSO_2$(phenyl), and —$NHSO_2(C_1$-$C_4$ haloalkyl).

As used herein, "substituted acyl" refers to the groups (substituted alkyl)-C(O)—; (substituted cycloalkyl)-C(O)—; (substituted aryl)-C(O)—; (substituted heteroaryl)-C(O)—; and (substituted heterocycloalkyl)-C(O)—, wherein the group is attached to the parent structure through the carbonyl functionality and wherein substituted alkyl, cycloalkyl, aryl, heteroaryl, and heterocycloalkyl, refer respectively to alkyl, cycloalkyl, aryl, heteroaryl, and heterocycloalkyl wherein one or more (such as up to 5, for example, up to 3) hydrogen atoms are replaced by a substituent independently chosen from —$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substituent for cycloalkyl or heterocycloalkyl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —$OP(O)(OR^b)OR^c$, sulfanyl (such as $SR^b$), sulfinyl (such as —$SOR^a$), and sulfonyl (such as —$SO_2R^a$ and —$SO_2NR^bR^c$), where $R^a$ is chosen from optionally substituted $C_1$-$C_6$ alkyl, optionally substituted alkenyl, optionally substituted alkynyl, optionally substituted aryl, and optionally substituted heteroaryl;

$R^b$ is chosen from H, optionally substituted $C_1$-$C_6$ alkyl, optionally substituted cycloalkyl, optionally substituted heterocycloalkyl, optionally substituted aryl, and optionally substituted heteroaryl; and $R^c$ is chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently chosen from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substituent for cycloalkyl or heterocycloalkyl), —$CO_2H$, —$C(O)OC_1$-$C_4$ alkyl, —$CON(C$ alkyl)($C_1$-$C_4$ alkyl), —$CONH(C_1$-$C_4$ alkyl), —$CONH_2$, —$NHC(O)(C_1$-

As used herein, "substituted alkoxy" refers to alkoxy wherein the alkyl constituent is substituted (i.e. —O-(substituted alkyl)) wherein "substituted alkyl" refers to alkyl wherein one or more (such as up to 5, for example, up to 3) hydrogen atoms are replaced by a substituent independently chosen from $R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substituent for cycloalkyl or heterocycloalkyl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —$OP(O)(OR^b)$ $OR^c$, sulfanyl (such as $SR^b$), sulfinyl (such as —$SOR^a$), and sulfonyl (such as —$SO_2R^a$ and —$SO_2NR^bR^c$), where $R^a$ is chosen from optionally substituted $C_1$-$C_6$ alkyl, optionally substituted alkenyl, optionally substituted alkynyl, optionally substituted aryl, and optionally substituted heteroaryl;

$R^b$ is chosen from H, optionally substituted $C_1$-$C_6$ alkyl, optionally substituted cycloalkyl, optionally substituted heterocycloalkyl, optionally substituted aryl, and optionally substituted heteroaryl; and $R^c$ is chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently chosen from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substituent for cycloalkyl or heterocycloalkyl), —$CO_2H$, —$C(O)OC_1$-$C_4$ alkyl, —$CON(C$ alkyl)($C_1$-$C_4$ alkyl), —$CONH(C_1$-$C_4$ alkyl), —$CONH_2$, —$NHC(O)(C_1$-

$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), and —$NHSO_2$($C_1$-$C_4$ haloalkyl).

In some embodiments, a substituted alkoxy group is "polyalkoxy" or —O-(optionally substituted alkylene)-(optionally substituted alkoxy), and includes groups such as —$OCH_2CH_2OCH_3$, and residues of glycol ethers such as polyethyleneglycol, and —$O(CH_2CH_2O)_x$ $CH_3$, where x is an integer of 2-20, such as 2-10, and for example, 2-5. Another substituted alkoxy group is hydroxyalkoxy or —$OCH_2(CH_2)_y$OH, where y is an integer of 1-10, such as 1-4.

As used herein, "substituted alkoxycarbonyl" refers to the group (substituted alkyl)-O—C(O)— wherein the group is attached to the parent structure through the carbonyl functionality and wherein substituted refers to alkyl wherein one or more (such as up to 5, for example, up to 3) hydrogen atoms are replaced by a substituent independently chosen from —$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substituent for cycloalkyl or heterocycloalkyl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —$OP(O)(OR^b)OR^c$, sulfanyl (such as $SR^b$), sulfinyl (such as —$SOR^a$), and sulfonyl (such as —$SO_2R^a$ and —$SO_2NR^bR^c$), where $R^a$ is chosen from optionally substituted $C_1$-$C_6$ alkyl, optionally substituted alkenyl, optionally substituted alkynyl, optionally substituted aryl, and optionally substituted heteroaryl;

$R^b$ is chosen from H, optionally substituted $C_1$-$C_6$ alkyl, optionally substituted cycloalkyl, optionally substituted heterocycloalkyl, optionally substituted aryl, and optionally substituted heteroaryl; and $R^c$ is chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently chosen from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for cycloalkyl or heterocycloalkyl), —$CO_2H$, —$C(O)OC_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), and —$NHSO_2$($C_1$-$C_4$ haloalkyl).

As used herein, "substituted amino" refers to the group —$NHR^d$ or —$NR^dR^e$ wherein $R^d$ is chosen from hydroxyl, formyl, optionally substituted alkoxy, optionally substituted alkyl, optionally substituted cycloalkyl, optionally substituted acyl, optionally substituted carbamimidoyl, aminocarbonyl, optionally substituted aryl, optionally substituted heteroaryl, optionally substituted heterocycloalkyl, optionally substituted alkoxycarbonyl, sulfinyl and sulfonyl, and wherein $R^e$ is chosen from optionally substituted alkyl, optionally substituted cycloalkyl, optionally substituted aryl, optionally substituted heteroaryl, and optionally substituted heterocycloalkyl, and wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently chosen from $R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substituent for cycloalkyl or heterocycloalkyl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —$OP(O)(OR^b)OR^c$, sulfanyl (such as $SR^b$), sulfinyl (such as —$SOR^a$), and sulfonyl (such as —$SO_2R^a$ and —$SO_2NR^bR^c$), where $R^a$ is chosen from optionally substituted $C_1$-$C_6$ alkyl, optionally substituted alkenyl, optionally substituted alkynyl, optionally substituted aryl, and optionally substituted heteroaryl;

$R^b$ is chosen from H, optionally substituted $C_1$-$C_6$ alkyl, optionally substituted cycloalkyl, optionally substituted heterocycloalkyl, optionally substituted aryl, and optionally substituted heteroaryl; and $R^c$ is chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently chosen from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for cycloalkyl or heterocycloalkyl), —$CO_2H$, —$C(O)OC_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), and —$NHSO_2$($C_1$-$C_4$ haloalkyl); and wherein optionally substituted acyl, optionally substituted alkoxycarbonyl, sulfinyl and sulfonyl are as defined herein.

The term "substituted amino" also refers to N-oxides of the groups —$NHR^d$, and $NR^dR^d$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

Compounds described herein include, but are not limited to, their optical isomers, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, compounds include Z- and E-forms (or cis- and trans-forms) of compounds with carbon-carbon double bonds. Where compounds described herein exist in various tautomeric forms, the term "compound" is intended to include all tautomeric forms of the compound.

Compounds of Formula I also include crystalline and amorphous forms of those compounds, including, for example, polymorphs, pseudopolymorphs, solvates (including hydrates), unsolvated polymorphs (including anhydrates), conformational polymorphs, and amorphous forms of the compounds, as well as mixtures thereof. "Crystalline form," "polymorph," and "novel form" may be used interchangeably herein, and are meant to include all crystalline and amorphous forms of the compound, including, for example, polymorphs, pseudopolymorphs, solvates (including hydrates), unsolvated polymorphs (including anhydrates), conformational polymorphs, and amorphous forms, as well as mixtures thereof, unless a particular crystalline or amorphous form is referred to. Similarly, "pharmaceutically acceptable salts of compounds of Formula I also include crystalline and amorphous forms of those compounds, including, for example, polymorphs, pseudopolymorphs, solvates (including hydrates), unsolvated polymorphs (including anhydrates), conformational polymorphs, and amorphous forms of the pharmaceutically acceptable salts, as well as mixtures thereof.

A "solvate" is formed by the interaction of a solvent and a compound. The term "compound" is intended to include solvates of compounds. Similarly, "pharmaceutically acceptable salts" includes solvates of pharmaceutically acceptable salts. Suitable solvates are pharmaceutically acceptable solvates, such as hydrates, including monohydrates and hemi-hydrates.

Compounds of Formula I also include other pharmaceutically acceptable forms of the recited compounds, including chelates, non-covalent complexes, prodrugs, and mixtures thereof.

A "chelate" is formed by the coordination of a compound to a metal ion at two (or more) points. The term "compound" is intended to include chelates of compounds. Similarly, "pharmaceutically acceptable salts" includes chelates of pharmaceutically acceptable salts.

A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding). Such non-covalent complexes are included in the term "compound". Similarly, "pharmaceutically acceptable salts" includes "non-covalent complexes" of pharmaceutically acceptable salts.

The term "hydrogen bond" refers to a form of association between an electronegative atom (also known as a hydrogen bond acceptor) and a hydrogen atom attached to a second, relatively electronegative atom (also known as a hydrogen bond donor). Suitable hydrogen bond donor and acceptors are well understood in medicinal chemistry.

"Hydrogen bond acceptor" refers to a group comprising an oxygen or nitrogen, such as an oxygen or nitrogen that is $sp^2$-hybridized, an ether oxygen, or the oxygen of a sulfoxide or N-oxide.

The term "hydrogen bond donor" refers to an oxygen, nitrogen, or heteroaromatic carbon that bears a hydrogen. group containing a ring nitrogen or a heteroaryl group containing a ring nitrogen.

The compounds disclosed herein can be used in different enriched isotopic forms, e.g., enriched in the content of $^2H$, $^3H$, $^{11}C$, $^{13}C$ and/or $^{14}C$. In one particular embodiment, the compound is deuterated at at least one position. Such deuterated forms can be made by the procedure described in U.S. Pat. Nos. 5,846,514 and 6,334,997. As described in U.S. Pat. Nos. 5,846,514 and 6,334,997, deuteration can improve the efficacy and increase the duration of action of drugs.

Deuterium substituted compounds can be synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, HOOC—$(CH_2)_n$—COOH where n is 0-4, and like salts. Similarly, pharmaceutically acceptable cations include, but are not limited to sodium, potassium, calcium, aluminum, lithium, and ammonium.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

"Prodrugs" described herein include any compound that becomes a compound of Formula I when administered to a subject, e.g., upon metabolic processing of the prodrug. Similarly, "pharmaceutically acceptable salts" includes "prodrugs" of pharmaceutically acceptable salts. Examples of prodrugs include derivatives of functional groups, such as a carboxylic acid group, in the compounds of Formula I. Exemplary prodrugs of a carboxylic acid group include, but are not limited to, carboxylic acid esters such as alkyl esters, hydroxyalkyl esters, arylalkyl esters, and aryloxyalkyl esters. Other exemplary prodrugs include lower alkyl esters such as ethyl ester, acyloxyalkyl esters such as pivaloyloxymethyl (POM), glycosides, and ascorbic acid derivatives.

Other exemplary prodrugs include amides of carboxylic acids. Exemplary amide prodrugs include metabolically labile amides that are formed, for example, with an amine and a carboxylic acid. Exemplary amines include $NH_2$, primary, and secondary amines such as NHR$^x$, and NR$^x$R$^y$, wherein R$^x$ is hydrogen, (C$_1$-C$_{18}$)-alkyl, (C$_3$-C$_7$)-cycloalkyl, (C$_3$-C$_7$)-cycloalkyl-(C$_1$-C$_4$)-alkyl-, (C$_6$-C$_{14}$)-aryl which is unsubstituted or substituted by a residue (C$_1$-C$_2$)-alkyl, (C$_1$-C$_2$)-alkoxy, fluoro, or chloro; heteroaryl-, (C$_6$-C$_{14}$)-aryl-(C$_1$-C$_4$)-alkyl- where aryl is unsubstituted or substituted by a residue (C$_1$-C$_2$)-alkyl, (C$_1$-C$_2$)-alkoxy, fluoro, or chloro; or heteroaryl-(C$_1$-C$_4$)-alkyl- and in which R$^y$ has the meanings indicated for R$^x$ with the exception of hydrogen or wherein R$^x$ and R$^y$, together with the nitrogen to which they are bound, form an optionally substituted 4- to 8-membered heterocycloalkyl ring which optionally includes one or two additional heteroatoms chosen from nitrogen, oxygen, and sulfur. A discussion of prodrugs is provided in T. Higuchi and V. Stella, Pro-drugs as Novel Delivery Systems, Vol. 14 of the A.C.S. Symposium Series, in Edward B. Roche, ed., Bioreversible Carriers in Drug Design, American Pharmaceutical Association and Pergamon Press, 1987, and in Design of Prodrugs, ed. H. Bundgaard, Elsevier, 1985.

As used herein the terms "group", "radical" or "fragment" are synonymous and are intended to indicate functional groups or fragments of molecules attachable to a bond or other fragments of molecules.

As used herein, "modulation" refers to a change in activity as a direct or indirect response to the presence of a chemical entity as described herein, relative to the activity of in the absence of the chemical entity. The change may be an increase in activity or a decrease in activity, and may be due to the direct interaction of the compound with the a target or due to the interaction of the compound with one or more other factors that in turn affect the target's activity. For example, the presence of the chemical entity may, for example, increase or decrease the target activity by directly binding to the target, by causing (directly or indirectly) another factor to increase or decrease the target activity, or by (directly or indirectly) increasing or decreasing the amount of target present in the cell or organism.

As used herein, "active agent" is used to indicate a chemical entity which has biological activity. In certain embodiments, an "active agent" is a compound having pharmaceutical utility. For example an active agent may be an anti-cancer therapeutic.

As used herein, "significant" refers to any detectable change that is statistically significant in a standard parametric test of statistical significance such as Student's T-test, where p <0.05.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, "therapeutically effective amount" of a chemical entity described herein refers to an amount effective, when administered to a human or non-human subject, to provide a therapeutic benefit such as amelioration of symptoms, slowing of disease progression, or prevention of disease.

"Treating" or "treatment" encompasses administration of at least one compound of Formula I, or a pharmaceutically acceptable salt thereof, to a mammalian subject, particularly a human subject, in need of such an administration and includes (i) arresting the development of clinical symptoms of the disease, such as cancer, (ii) bringing about a regression in the clinical symptoms of the disease, such as cancer, and/or (iii) prophylactic treatment for preventing the onset of the disease, such as cancer.

As used herein, "cancer" refers to all types of cancer or neoplasm or malignant tumors found in mammals, including carcinomas and sarcomas. Examples of cancer are cancer of the brain, breast, cervix, colon, head & neck, kidney, lung, non-small cell lung, melanoma, mesothelioma, ovary, sarcoma, stomach, uterus and Medulloblastoma.

As used herein, "subject" refers to a mammal that has been or will be the object of treatment, observation or experiment. The methods described herein can be useful in both human therapy and veterinary applications. In some embodiments, the subject is a human.

The term "mammal" is intended to have its standard meaning, and encompasses humans, dogs, cats, sheep, and cows, for example.

Provided is at least one chemical entity chosen from compounds of Formula I

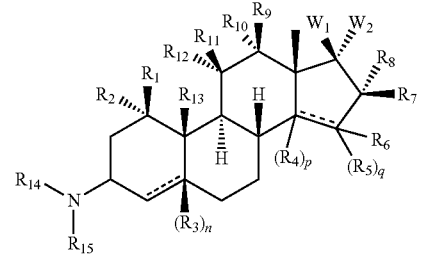

Formula I and pharmaceutically acceptable salts thereof, wherein

R$_1$, R$_2$, R$_3$, R$_4$, R$_5$, R$_6$, R$_9$, R$_{10}$, R$_{11}$ and R$_{12}$ are independently chosen from hydrogen, hydroxy, optionally substituted alkyl, optionally substituted cycloalkyl, optionally substituted alkenyl, optionally substituted alkynyl, optionally substituted alkoxy, optionally substituted aryloxy, optionally substituted heteroaryloxy, optionally substituted heterocycloalkyloxy, optionally substituted aminocarbonyloxy, optionally substituted acyloxy, optionally substituted alkoxycarbonyloxy, and optionally substituted amino; or R$_1$ and R$_2$, or R$_5$ and R$_6$, or R$_7$ and R$_8$, or R$_9$ and R$_{10}$, or R$_{11}$ and R$_{12}$ mutually independently, together in each case denote an oxo group (=O); or R$_4$ and R$_5$ may optionally be joined together with any intervening atoms to form an optionally substituted heterocycloalkyl ring;

R$_7$ is chosen from hydrogen, hydroxy, optionally substituted alkoxy, optionally substituted aryloxy, optionally substituted heteroaryloxy, optionally substituted heterocycloalkyloxy, optionally substituted aminocarbonyloxy, optionally substituted acyloxy, optionally substituted alkoxycarbonyloxy, and optionally substituted amino;

R$_8$ is chosen from hydrogen, optionally substituted alkyl, optionally substituted cycloalkyl, optionally substituted alkenyl, and optionally substituted alkynyl;

R$_{13}$ is chosen from hydrogen, optionally substituted alkyl, and formyl;

R$_{14}$ is chosen from hydrogen, optionally substituted alkyl, optionally substituted cycloalkyl, optionally substituted heterocycloalkyl, optionally substituted aryl, and optionally substituted heteroaryl; and R$_{15}$ is chosen from hydrogen, hydroxyl, formyl, optionally substituted alkoxy, optionally substituted alkyl, optionally substituted cycloalkyl, optionally substituted heterocycloalkyl, optionally substituted aryl, and optionally substituted heteroaryl, —COR$_{16}$, —CO$_2$R$_{16}$, —CONR$_{17}$R$_{18}$, —C(NR$_{19}$)NR$_{17}$R$_{18}$, —C(NCN)NR$_{17}$R$_{18}$, —SO$_2$R$_{16}$, and —SO$_2$NR$_{17}$R$_{18}$, where R$_{16}$ is chosen from optionally substituted alkyl, optionally substituted cycloalkyl, optionally substituted heterocycloalkyl, optionally substituted aryl, and optionally substituted heteroaryl; and R$_{17}$, R$_{18}$ and R$_{19}$ are independently chosen from hydrogen, optionally substituted alkyl, optionally substituted cycloalkyl, optionally substituted heterocycloalkyl, optionally substituted aryl, and optionally substituted heteroaryl; or R$_{17}$ and R$_{18}$ may be joined together with any intervening atoms to form an optionally substituted heterocycloalkyl ring, or R$_{14}$ and R$_{15}$ are joined together with any intervening atoms to form an optionally substituted 4- to 8-membered heterocycloalkyl or or optionally substituted 5- to 8-membered heteroaryl ring;

W$_1$ is chosen from the following moieties:

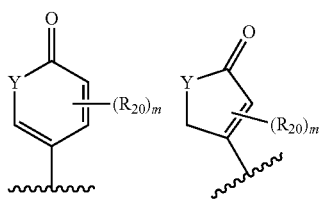

wherein Y is chosen from O and NR$_{21}$;

R$_{20}$ is chosen from cyano, halo, hydroxy, azido, nitro, carboxy, sulfinyl, sulfanyl, optionally substituted alkoxy, optionally substituted aryloxy, optionally substituted heteroaryloxy, optionally substituted heterocycloalkyloxy, optionally substituted alkoxycarbonyl, optionally substituted alkyl, optionally substituted alkenyl, optionally substituted aryloxy, optionally substituted aryl, optionally substituted heteroaryl, optionally substituted heterocycloalkyl, optionally substituted amino, optionally substituted acyl, optionally substituted alkoxycarbonyl, optionally substituted aminocarbonyl, optionally substituted aminosulfonyl, optionally substituted carbaminodoyl, and optionally substituted alkynyl;

R$_{21}$ is chosen from hydrogen, optionally substituted alkyl, optionally substituted cycloalkyl, optionally substituted heterocycloalkyl, optionally substituted aryl, and optionally substituted heteroaryl;

W$_2$ is chosen from hydrogen, optionally substituted alkyl, optionally substituted cycloalkyl, optionally substituted alkenyl, and optionally substituted alkynyl;

m is selected from 0, 1, 2, and 3;

n, p, and q is independently selected from 0 and 1; and the dotted line represents a single bond or a double bond.

In some embodiments, R$_{15}$ is —COR$_{16}$ and R$_{16}$ is not methyl, ethyl, cyclopentyl, or phenyl.

In other embodiments, R$_{14}$ is hydrogen, R$_{15}$ is —CONR$_{17}$R$_{18}$, and R$_{17}$ and R$_{18}$ taken together form a ring which is not a piperidine, piperazine, morpholine, or diazepane ring.

In other embodiments, R$_{14}$ is hydrogen, R$_{15}$ is —CONR$_{17}$R$_{18}$, and R$_{17}$ or R$_{15}$ are not ethyl, aminoethyl, piperidinyl, or piperidinylmethyl.

In some embodiments, the compound of Formula I is not

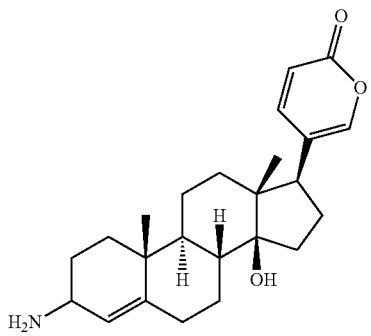

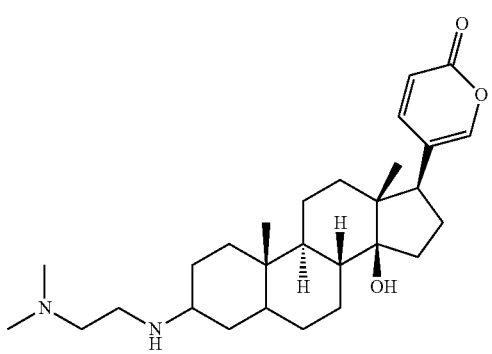

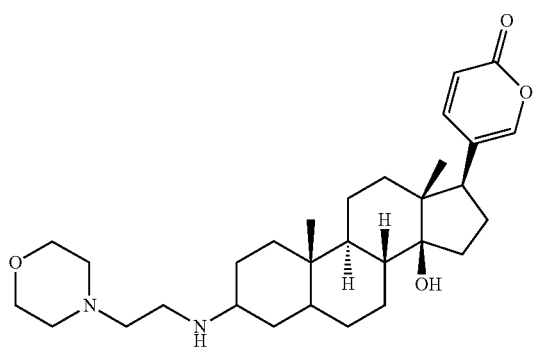

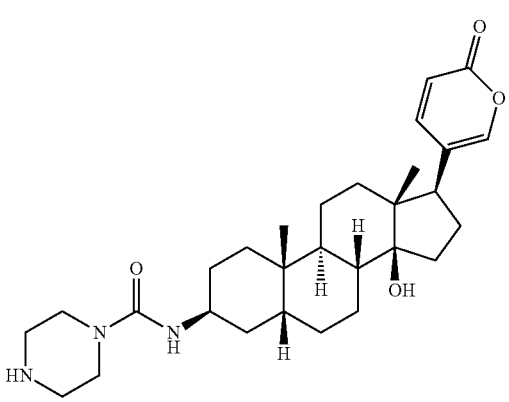

-continued

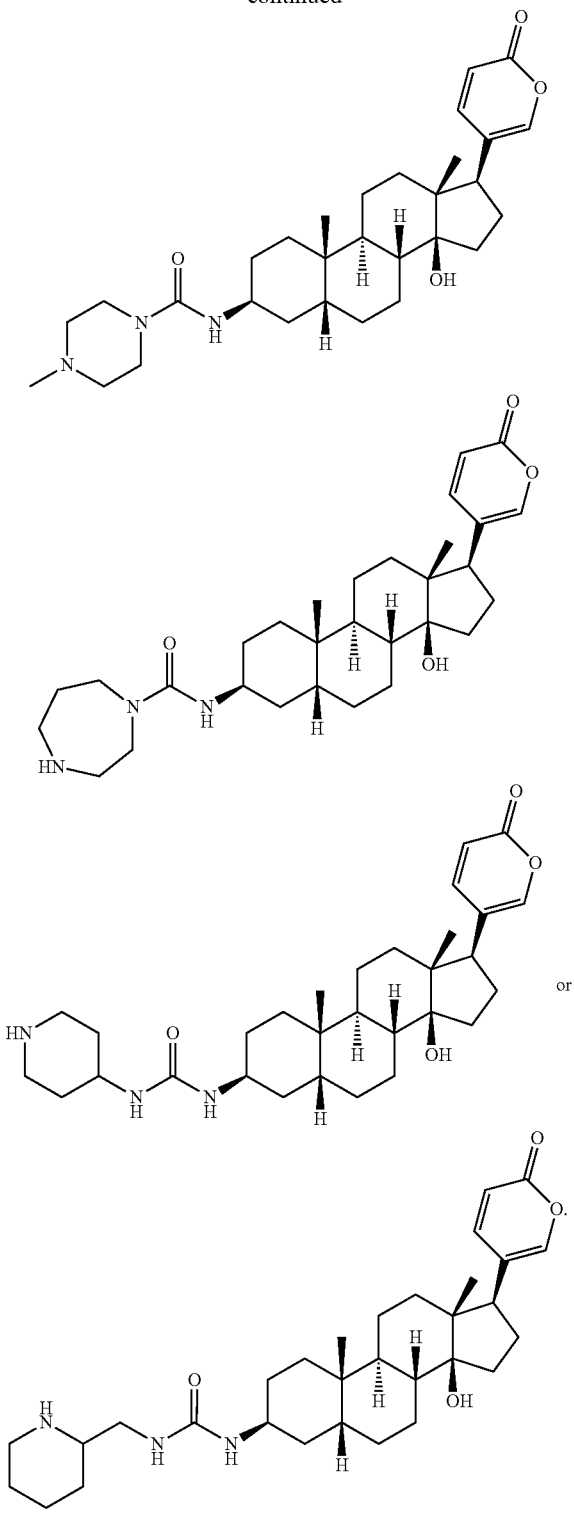

In some embodiments, $R_1$, $R_2$, $R_3$, $R_5$, $R_6$, $R_9$, $R_{10}$, $R_{11}$ and $R_{12}$ are independently chosen from hydrogen, hydroxy, optionally substituted alkyl, optionally substituted alkoxy, optionally substituted aminocarbonyloxy, optionally substituted acyloxy, optionally substituted alkoxycarbonyloxy, and optionally substituted amino. In some embodiments, $R_1$, $R_2$, $R_3$, $R_5$, $R_6$, $R_9$, $R_{10}$, $R_{11}$ and $R_{12}$ are independently chosen from hydrogen, hydroxy, and optionally substituted alkyl. In some embodiments, $R_1$, $R_2$, $R_3$, $R_5$, $R_6$, $R_9$, $R_{10}$, $R_{11}$ and $R_{12}$ are independently chosen from hydrogen, hydroxy, and lower alkyl. In some embodiments, $R_1$, $R_2$, $R_3$, $R_5$, $R_6$, $R_9$, $R_{10}$, $R_{11}$ and $R_{12}$ are independently chosen from hydrogen, hydroxy, and methyl. In some embodiments, $R_1$, $R_2$, $R_5$, $R_6$, $R_9$, $R_{10}$, $R_{11}$ and $R_{12}$ are independently chosen from hydrogen, hydroxy, and methyl; $R_3$ is chosen from hydroxyl and hydrogen. In some embodiments, at least one of $R_1$ and $R_2$, or $R_5$ and $R_6$, or $R_7$ and $R_5$, or $R_9$ and $R_{10}$, or $R_{11}$ and $R_{12}$ mutually independently, together in each case denotes an oxo group (=O).

In some embodiments, $R_4$ is hydroxy.

In some embodiments, $R_4$ and $R_5$ are joined together with any intervening atoms to form an optionally substituted 3- to 8-membered heterocycloalkyl ring. In some embodiments, $R_4$ and $R_5$ are joined together with any intervening atoms to form an oxirane ring.

In some embodiments, $R_7$ is chosen from hydrogen, hydroxy, optionally substituted alkoxy, optionally substituted aminocarbonyloxy, optionally substituted acyloxy, optionally substituted alkoxycarbonyloxy, and optionally substituted amino. In some embodiments, $R_7$ is chosen from hydrogen and optionally substituted acyloxy. In some embodiments, $R_7$ is chosen from hydrogen and acyloxy. In some embodiments, $R_7$ is chosen from hydrogen and —OCOCH$_3$.

In some embodiments, $R_8$ and and $W_2$ are independently chosen from hydrogen and optionally substituted alkyl. In some embodiments, $R_8$ and and $W_2$ are independently chosen from hydrogen and lower alkyl. In some embodiments, $R_8$ is hydrogen. In some embodiments, $W_2$ is hydrogen.

In some embodiments, $R_{13}$ is chosen from hydrogen and optionally substituted alkyl. In some embodiments, $R_{13}$ is chosen from hydrogen and loweralkyl. In some embodiments, $R_{13}$ is chosen from hydrogen, methyl, and hydroxymethyl.

In some embodiments, $R_{14}$ is chosen from hydrogen, optionally substituted lower alkyl, optionally substituted cycloalkyl, optionally substituted heterocycloalkyl, optionally substituted aryl, and optionally substituted heteroaryl. In some embodiments, $R_{14}$ is chosen from hydrogen and optionally substituted lower alkyl. In some embodiments, $R_{14}$ is hydrogen.

In some embodiments, $R_{15}$ is chosen from hydrogen, optionally substituted alkyl, optionally substituted cycloalkyl, optionally substituted heterocycloalkyl, —COR$_{16}$, —CO$_2$R$_{16}$, —CONR$_{17}$R$_{18}$, —C(NR$_{19}$)NR$_{17}$R$_{18}$, —C(NCN)NR$_{17}$R$_{18}$, —SO$_2$R$_{16}$, and —SO$_2$NR$_{17}$R$_{18}$.

In some embodiments, $R_{15}$ is lower alkyl optionally substituted with hydroxyl, optionally substituted amino, or optionally substituted heterocycloalkyl. In some embodiments, $R_{15}$ is lower alkyl optionally substituted with hydroxyl, optionally substituted amino, or pyrrolidine optionally substituted with oxo.

In some embodiments, $R_{15}$ is chosen from —COR$_{16}$, —CO$_2$R$_{16}$, —CONR$_{17}$R$_{18}$, and —SO$_2$NR$_{17}$R$_{18}$. In some embodiments, $R_{15}$ is chosen from —COR$_{16}$, —CO$_2$R$_{16}$, and —CONR$_{17}$R$_{18}$.

In some embodiments, $R_{15}$ is —CONR$_{17}$R$_{18}$ and $R_{14}$ taken together with $R_{17}$ form a 5- or 6-membered, optionally substituted, heterocyclic ring.

In some embodiments, $R_{16}$ is chosen from optionally substituted alkyl, optionally substituted cycloalkyl, optionally substituted heterocycloalkyl, optionally substituted aryl, and optionally substituted heteroaryl. In some embodiments, $R_{16}$ is chosen from optionally substituted alkyl, optionally substituted cycloalkyl, and optionally substituted heterocycloalkyl. In some embodiments, R$_{16}$ is chosen from alkyl optionally substituted with one or two groups independently hydroxyl, optionally substituted amino, lower alkoxy, and heterocycloalkyl, wherein heterocycloalkyl is optionally substituted with oxo. In some embodiments, R$_{16}$ is methyl, lower alkyl substituted with heterocycloalkyl, lower alkyl substituted with optionally substituted amino, or heterocycloalkyl. In some embodiments, R$_{16}$ is methyl, lower alkyl substituted with heterocycloalkyl, lower alkyl substituted with amino, or heterocycloalkyl.

In some embodiments, R$_{17}$ and R$_{18}$ are independently chosen from hydrogen, optionally substituted alkyl, optionally substituted cycloalkyl, optionally substituted heterocycloalkyl, optionally substituted aryl, and optionally substituted heteroaryl. In some embodiments, R$_{17}$ and R$_{18}$ are independently chosen from hydrogen, optionally substituted alkyl, optionally substituted cycloalkyl, and optionally substituted heterocycloalkyl. In some embodiments, R$_{17}$ is hydrogen. In some embodiments, R$_{18}$ is lower alkyl optionally substituted with optionally substituted amino or hydroxyl.

In some embodiments, R$_{17}$ and R$_{18}$ are joined together with any intervening atoms to form an optionally substituted 4- to 8-membered heterocycloalkyl ring.

In some embodiments, R$_{17}$ and R$_{18}$ are joined together to form a 4- to 8-membered heterocycloalkyl ring optionally substituted with one or two groups independently chosen from amino, hydroxyl, oxo, and lower alkyl.

In some embodiments, R$_{17}$ and R$_{18}$ are joined together to form a 5- to 7-membered heterocycloalkyl ring chosen from morpholinyl, piperazinyl, diazepanyl, piperidinyl, or pyrrolidinyl.

In some embodiments, R$_{17}$ and R$_{18}$ are joined together to form a 5- to 7-membered heterocycloalkyl ring chosen from 3-hydroxypyrrolidine-1-yl, 3-aminopyrrolidine-1-yl, 3-oxopiperazine-1-yl, 4-methyl-1,4-diazepane-1-yl, 1,4-diazepane-1-yl, piperazine-1-yl, 4-methylpiperazine-1-yl, and morpholine-4-yl.

In some embodiments, R$_{19}$ is chosen from hydrogen, optionally substituted alkyl, optionally substituted cycloalkyl, and optionally substituted heterocycloalkyl. In some embodiments, R$_{19}$ is chosen from hydrogen and optionally substituted alkyl.

In some embodiments, R$_{14}$ and R$_{15}$ are joined together with any intervening atoms to form an optionally substituted 4- to 8-membered heterocycloalkyl or or optionally substituted 5- to 8-membered heteroaryl ring.

In some embodiments, R$_{14}$ and R$_{15}$ are joined together with any intervening atoms to form an optionally substituted 4- to 8-membered heterocycloalkyl ring. In some embodiments, R$_{14}$ and R$_{15}$ are joined together with any intervening atoms to form an morpholin-4-yl, piperidin-1-yl, piperidin-4-yl, piperazin-1-yl, pyrrolidin-1-yl, pyrrolidin-2-yl, each of which is optionally substituted.

In some embodiments, R$_{14}$ and R$_{15}$ are joined together with any intervening atoms to form an optionally substituted 5- to 8-membered heteroaryl ring. In some embodiments, R$_{14}$ and R$_{15}$ are joined together with any intervening atoms to form imidazolyl, or pyrazolyl, each of which is optionally substituted.

In some embodiments, Y is chosen from O, NH and NCH$_3$. In some embodiments, Y is O.

In some embodiments, R$_{20}$ is chosen from cyano, halo, hydroxy, carboxy, sufonyl, optionally substituted alkoxy, optionally substituted alkoxycarbonyl, optionally substituted alkyl, optionally substituted amino, optionally substituted acyl, optionally substituted alkoxycarbonyl, optionally substituted aminocarbonyl, and optionally substituted aminosulfonyl.

In some embodiments, m is 0.

In some embodiments, the dotted line represents a single bond.

In some embodiments, the dotted line represents a double bond.

Also provided is at least one chemical entity of claim 1 wherein the compound of Formula I is chosen from compounds of Formula Ia.

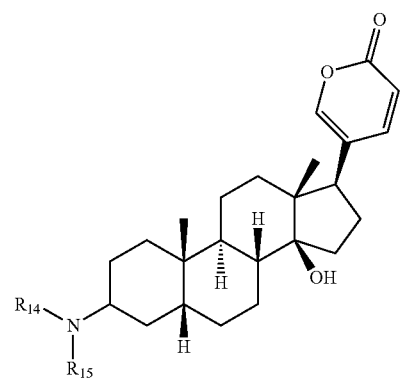

Formula Ia

Also provided is at least one chemical entity of claim 1 wherein the compound of Formula I is chosen from compounds of Formula Ib.

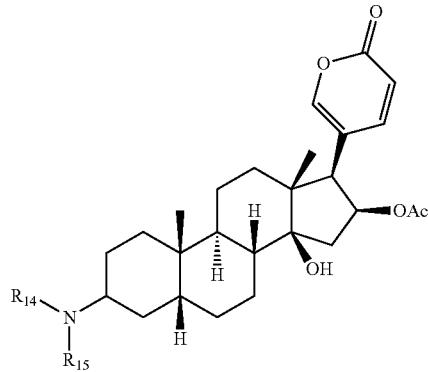

Formula Ib

Also provided is at least one chemical entity of claim 1 wherein the compound of Formula I is chosen from compounds of Formula Ic.

Formula Ic

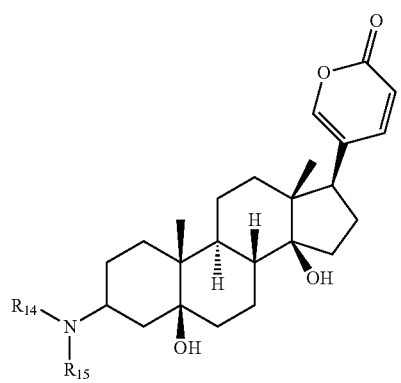

Also provided is at least one chemical entity of claim 1 wherein the compound of Formula I is chosen from compounds of Formula Id.

Formula Id

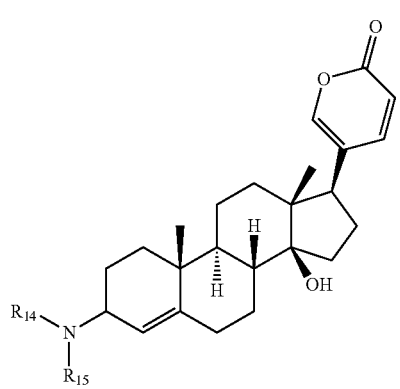

Also provided is at least one chemical entity of claim 1 wherein the compound of Formula I is chosen from compounds of Formula Ie.

Formula Ie

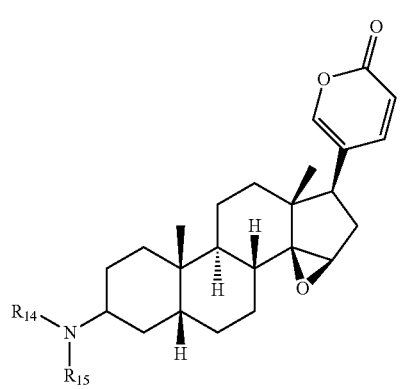

Also provided is at least one chemical entity of claim 1 wherein the compound of Formula I is chosen from compounds of Formula If.

Formula If

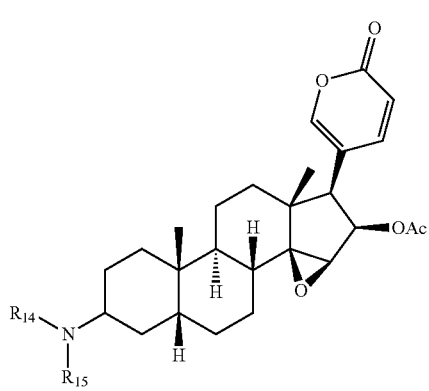

Also provided is at least one chemical entity of claim 1 wherein the compound of Formula I is chosen from compounds of Formula Ig.

Formula Ig

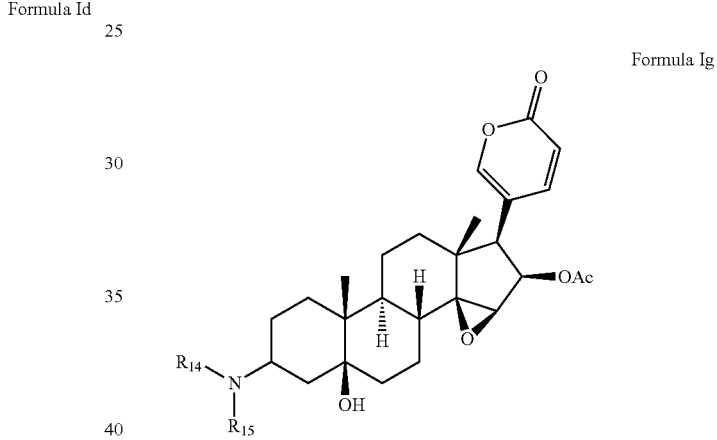

Also provided is at least one chemical entity of claim 1 wherein the compound of Formula I is chosen from compounds of Formula Ih.

Formula Ih

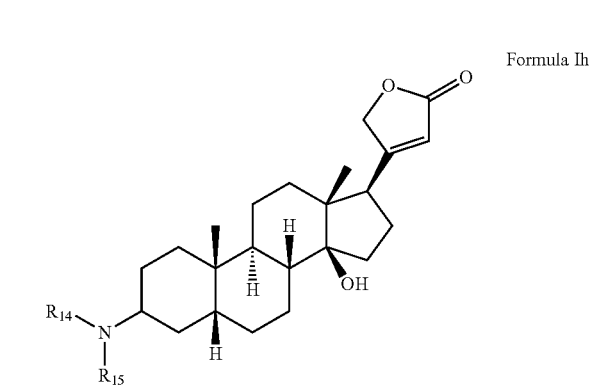

Also provided is at least one chemical entity of claim 1 wherein the compound of Formula I is chosen from compounds of Formula Ii.

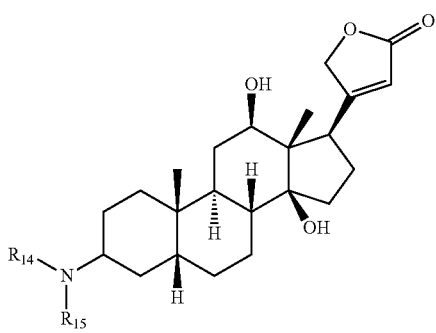

Formula Ii

Also provided is at least one chemical entity of claim 1 wherein the compound of Formula I is chosen from compounds of Formula Ij.

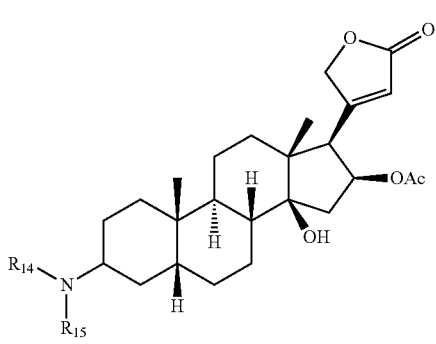

Formula Ij

Also provided is at least one chemical entity of claim 1 wherein the compound of Formula I is chosen from compounds of Formula Ik.

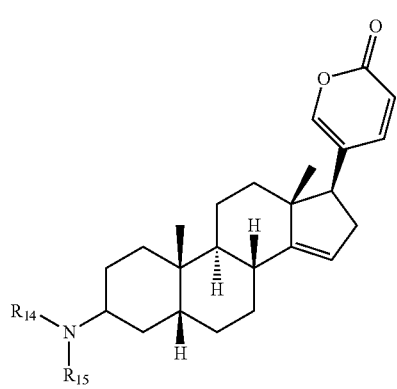

Formula Ik

Also provided is at least one chemical entity of claim 1 wherein the compound of Formula I is chosen from compounds of Formula Il.

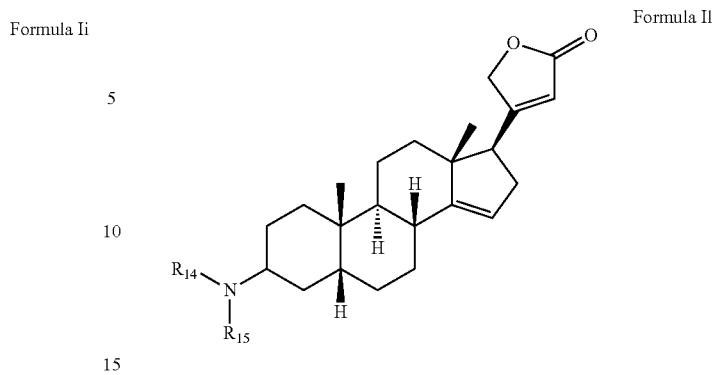

Formula Il

Also provided is at least one chemical entity chosen from
2-aminoethyl ((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)carbamate, 2-hydroxyethyl ((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)carbamate, 2-(pyrrolidin-1-yl)ethyl ((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)carbamate, 2-((R)-3-hydroxypyrrolidin-1-yl)ethyl ((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)carbamate, 2-morpholinoethyl ((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)carbamate, 2-(3-oxopiperazin-1-yl)ethyl ((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)carbamate, 1-(2-aminoethyl)-3-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)urea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-(2-hydroxyethyl)urea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-(2-(pyrrolidin-1-yl)ethyl)urea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-(2-morpholinoethyl)urea, N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-4-methylpiperazine-1-carboxamide, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-(2-(4-methylpiperazin-1-yl)ethyl)urea, N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)morpholine-4-carboxamide, 4-(3-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)ureido)butanoic acid, N-((5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)piperazine-1-carboxamide, N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)piperazine-1-carboxamide, (R)—N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-(hydroxymethyl)piperazine-1-carboxamide, (S)—N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-(hydroxymethyl)piperazine-1-carboxamide, (S)—N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-2-(hydroxymethyl)piperazine-1-carboxamide, (R)—N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-2-(hydroxymethyl)piperazine-1-carboxamide, N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-1,4-diazepane-1-carboxamide, N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-4-methyl-1,4-diazepane-1-carboxamide, N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-oxopiperazine-1-carboxamide, (S)-3-hydroxy-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)pyrrolidine-1-carboxamide, (R)-3-hydroxy-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)pyrrolidine-1-carboxamide, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-(2-(2-oxopiperazin-1-yl)ethyl)urea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-(2-(4-methyl-2-oxopiperazin-1-yl)ethyl)urea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-(2-(3-oxopiperazin-1-yl)ethyl)urea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-(2-((S)-3-hydroxypyrrolidin-1-yl)ethyl)urea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-(2-((R)-3-hydroxypyrrolidin-1-yl)ethyl)urea, 2-amino-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)acetamide, N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-2-(pyrrolidin-1-yl)acetamide, N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-2-morpholinoacetamide, (R)-2-amino-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)propanamide, (S)-2-amino-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)propanamide, (R)-2-amino-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-methylbutanamide, (S)-2-amino-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-methylbutanamide, (R)-2-amino-N1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)succinamide, (S)-2-amino-N1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)succinamide, (3S,5R,8R,9S,10S,13R,14S,16S,17R)-14-hydroxy-10,13-dimethyl-17-(2-oxo-2H-pyran-5-yl)-3-(((2-(pyrrolidin-1-yl)ethoxy)carbonyl)amino)hexadecahydro-1H-cyclopenta[a]phenanthren-16-yl acetate, (3S,5R,8R,9S,10S,13R,14S,16S,17R)-14-hydroxy-10,13-dimethyl-3-(((2-morpholinoethoxy)carbonyl)amino)-17-(2-oxo-2H-pyran-5-yl)hexadecahydro-1H-cyclopenta[a]phenanthren-16-yl acetate, (3S,5R,8R,9S,10S,13R,14S,16S,17R)-14-hydroxy-10,13-dimethyl-17-(2-oxo-2H-pyran-5-yl)-3-(((2-(3-oxopiperazin-1-yl)ethoxy)carbonyl)amino)hexadecahydro-1H-cyclopenta[a]phenanthren-16-yl acetate, (3S,5R,8R,9S,10S,13R,14S,16S,17R)-14-hydroxy-10,13-dimethyl-17-(2-oxo-2H-pyran-5-yl)-3-(3-(2-(pyrrolidin-1-yl)ethyl)ureido)hexadecahydro-1H-cyclopenta[a]phenanthren-16-yl acetate, (3S,5R,8R,9S,10S,13R,14S,16S,17R)-14-hydroxy-10,13-dimethyl-3-(3-(2-morpholinoethyl)ureido)-17-(2-oxo-2H-pyran-5-yl)hexadecahydro-1H-cyclopenta[a]phenanthren-16-yl acetate, (3S,5R,8R,9S,10S,13R,14S,16S,17R)-14-hydroxy-10,13-dimethyl-3-(4-methylpiperazine-1-carboxamido)-17-(2-oxo-2H-pyran-5-yl)hexadecahydro-1H-cyclopenta[a]phenanthren-16-yl acetate, (3S,5R,8R,9S,10S,13R,14S,16S,17R)-14-hydroxy-10,13-dimethyl-3-(3-(2-(4-methylpiperazin-1-yl)ethyl)ureido)-17-(2-oxo-2H-pyran-5-yl)hexadecahydro-1H-cyclopenta[a]phenanthren-16-yl acetate, (3S,5R,8R,9S,10S,13R,14S,16S,17R)-14-hydroxy-10,13-dimethyl-3-(morpholine-4-carboxamido)-17-(2-oxo-2H-pyran-5-yl)hexadecahydro-1H-cyclopenta[a]phenanthren-16-yl acetate, 4-(3-((3S,5R,8R,9S,10S,13R,14S,16S,17R)-16-acetoxy-14-hydroxy-10,13-dimethyl-17-(2-oxo-2H-pyran-5-yl)hexadecahydro-1H-cyclopenta[a]phenanthren-3-yl)ureido)butanoic acid, (3S,5R,8R,9S,10S,13R,14S,16S,17R)-14-hydroxy-10,13-dimethyl-17-(2-oxo-2H-pyran-5-yl)-3-(piperazine-1-carboxamido)hexadecahydro-1H-cyclopenta[a]phenanthren-16-yl acetate, (3S,5R,8R,9S,10S,13R,14S,16S,17R)-3-(1,4-diazepane-1-carboxamido)-14-hydroxy-10,13-dimethyl-17-(2-oxo-2H-pyran-5-yl)hexadecahydro-1H-cyclopenta[a]phenanthren-16-yl acetate, (3S,5R,8R,9S,10S,13R,14S,16S,17R)-14-hydroxy-10,13-dimethyl-3-(4-methyl-1,4-diazepane-1-carboxamido)-17-(2-oxo-2H-pyran-5-yl)hexadecahydro-1H-cyclopenta[a]phenanthren-16-yl acetate, (3S,5R,8R,9S,10S,13R,14S,16S,17R)-14-hydroxy-10,13-dimethyl-17-(2-oxo-2H-pyran-5-yl)-3-(3-oxopiperazine-1-carboxamido)hexadecahydro-1H-cyclopenta[a]phenanthren-16-yl acetate, (3S,5R,8R,9S,10S,13R,14S,16S,17R)-14-hydroxy-10,13-dimethyl-17-(2-oxo-2H-pyran-5-yl)-3-(3-(2-(2-oxopiperazin-1-yl)ethyl)ureido)hexadecahydro-114-cyclopenta[a]phenanthren-16-yl acetate, (3S,5R,8R,9S,10S,13R,14S,16S,17R)-14-hydroxy-10,13-dimethyl-3-(3-(2-(4-methyl-2-oxopiperazin-1-yl)ethyl)ureido)-17-(2-oxo-2H-pyran-5-yl)hexadecahydro-1H-cyclopenta[a]phenanthren-16-yl acetate, (3S,5R,8R,9S,10S,13R,14S,16S,17R)-14-hydroxy-10,13-dimethyl-17-(2-oxo-2H-pyran-5-yl)-3-(3-(2-(3-oxopiperazin-1-yl)ethyl)ureido)hexadecahydro-1H-cyclopenta[a]phenanthren-16-yl acetate, 2-aminoethyl ((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)carbamate, 2-(pyrrolidin-1-yl)ethyl ((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)carbamate, 2-morpholinoethyl ((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)carbamate, 2-(3-oxopiperazin-1-yl)ethyl ((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)carbamate, 1-(2-aminoethyl)-3-((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)urea, 1-((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)-3-(2-(pyrrolidin-1-yl)ethyl)urea, 1-((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)-3-(2-morpholinoethyl)urea, N-((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)piperazine-1-carboxamide, 1-((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)-3-(2-(piperazin-1-yl)ethyl)urea, N-((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)morpholine-4-carboxamide, 4-(3-((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)ureido)butanoic acid, N-((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)-4-methylpiperazine-1-carboxamide, N-((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)-1,4-diazepane-1-carboxamide, N-((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)-4-methyl-1,4-diazepane-1-carboxamide, N-((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)-3-oxopiperazine-1-carboxamide, (S)—N-((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)-3-hydroxypyrrolidine-1-carboxamide, (R)—N-((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)-3-hydroxypyrrolidine-1-carboxamide, (S)-3-amino-N-((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)pyrrolidine-1-carboxamide, (R)-3-amino-N-((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)pyrrolidine-1-carboxamide, 1-((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)-3-(2-(2-oxopiperazin-1-yl)ethyl)urea, 1-((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)-3-(2-(4-methyl-2-oxopiperazin-1-yl)ethyl)urea, 1-((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)-3-(2-(3-oxopiperazin-1-yl)ethyl)urea, 1-((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)-3-(2-((S)-3-hydroxypyrrolidin-1-yl)ethyl)urea, 1-((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)-3-(2-((R)-3-hydroxypyrrolidin-1-yl)ethyl)urea, 2-(pyrrolidin-1-yl)ethyl ((3S,8R,9S,10R,13R,14S,17R)-14-hydroxy-10,13-dimethyl-17-(2-oxo-2H-pyran-5-yl)-2,3,6,7,8,9,10,11,12,13,14,15,16,17-tetradecahydro-1H-cyclopenta[a]phenanthren-3-yl)carbamate, 2-morpholinoethyl ((3S,8R,9S,10R,13R,14S,17R)-14-hydroxy-10,13-dimethyl-17-(2-oxo-2H-pyran-5-yl)-2,3,6,7,8,9,10,11,12,13,14,15,16,17-tetradecahydro-1H-cyclopenta[a]phenanthren-3-yl)carbamate, 2-(3-oxopiperazin-1-yl)ethyl ((3S,8R,9S,10R,13R,14S,17R)-14-hydroxy-10,13-dimethyl-17-(2-oxo-2H-pyran-5-yl)-2,3,6,7,8,9,10,11,12,13,14,15,16,17-tetradecahydro-1H-cyclopenta[a]phenanthren-3-yl)carbamate, 1-((3S,8R,9S,10R,13R,14S,17R)-14-hydroxy-10,13-dimethyl-17-(2-oxo-2H-pyran-5-yl)-2,3,6,7,8,9,10,11,12,13,14,15,16,17-tetradecahydro-1H-cyclopenta[a]phenanthren-3-yl)-3-(2-(pyrrolidin-1-yl)ethyl)urea, 1-((3S,8R,9S,10R,13R,14S,17R)-14-hydroxy-10,13-dimethyl-17-(2-oxo-2H-pyran-5-yl)-2,3,6,7,8,9,10,11,12,13,14,15,16,17-tetradecahydro-1H-cyclopenta[a]phenanthren-3-yl)-3-(2-morpholinoethyl)urea, N-((3S,8R,9S,10R,13R,14S,17R)-14-hydroxy-10,13-dimethyl-17-(2-oxo-2H-pyran-5-yl)-2,3,6,7,8,9,10,11,12,13,14,15,16,17-tetradecahydro-1H-cyclopenta[a]phenanthren-3-yl)piperazine-1-carboxamide, 1-((3S,8R,9S,10R,13R,14S,17R)-14-hydroxy-10,13-dimethyl-17-(2-oxo-2H-pyran-5-yl)-2,3,6,7,8,9,10,11,12,13,14,15,16,17-tetradecahydro-1H-cyclopenta[a]phenanthren-3-yl)-3-(2-(piperazin-1-yl)ethyl)urea, N-((3S,8R,9S,10R,13R,14S,17R)-14-hydroxy-10,13-dimethyl-17-(2-oxo-2H-pyran-5-yl)-2,3,6,7,8,9,10,11,12,13,14,15,16,17-tetradecahydro-1H-cyclopenta[a]phenanthren-3-yl)morpholine-4-carboxamide, 4-(3-((3S,8R,9S,10R,13R,14S,17R)-14-hydroxy-10,13-dimethyl-17-(2-oxo-2H-pyran-5-yl)-2,3,6,7,8,9,10,11,12,13,14,15,16,17-tetradecahydro-1H-cyclopenta[a]phenanthren-3-yl)ureido)butanoic acid N-((3S,8R,9S,10R,13R,14S,17R)-14-hydroxy-10,13-dimethyl-17-(2-oxo-2H-pyran-5-yl)-2,3,6,7,8,9,10,11,12,13,14,15,16,17-tetra decahydro-1H-cyclopenta[a]phenanthren-3-yl)-4-methylpiperazine-1-carboxamide, N-((3S,8R,9S,10R,13R,14S,17R)-14-hydroxy-10,13-dimethyl-17-(2-oxo-2H-pyran-5-yl)-2,3,6,7,8,9,10,11,12,13,14,15,16,17-tetra decahydro-1H-cyclopenta[a]phenanthren-3-yl)-1,4-diazepane-1-carboxamide, N-((3S,8R,9S,10R,13R,14S,17R)-14-hydroxy-10,13-dimethyl-17-(2-oxo-2H-pyran-5-yl)-2,3,6,7,8,9,10,11,12,13,14,15,16,17-tetradecahydro-1H-cyclopenta[a]phenanthren-3-yl)-4-methyl-1,4-diazepane-1-carboxamide, N-((3S,8R,9S,10R,13R,14S,17R)-14-hydroxy-10,13-dimethyl-17-(2-oxo-2H-pyran-5-yl)-2,3,6,7,8,9,10,11,12,13,14,15,16,17-tetradecahydro-1H-cyclopenta[a]phenanthren-3-yl)-3-oxopiperazine-1-carboxamide, (S)-3-hydroxy-N-((3S,8R,9S,10R,13R,14S,17R)-14-hydroxy-10,13-dimethyl-17-(2-oxo-2H-pyran-5-yl)-2,3,6,7,8,9,10,11,12,13,14,15,16,17-tetradecahydro-1H-cyclopenta[a]phenanthren-3-yl)pyrrolidine-1-carboxamide, (R)-3-hydroxy-N-((3S,8R,9S,10R,13R,14S,17R)-14-hydroxy-10,13-dimethyl-17-(2-oxo-2H-pyran-5-yl)-2,3,6,7,8,9,10,11,12,13,14,15,16,17-tetradecahydro-1H-cyclopenta[a]phenanthr en-3-yl)pyrrolidine-1-carboxamide, 1-((3S,8R,9S,10R,13R,14S,17R)-14-hydroxy-10,13-dimethyl-17-(2-oxo-2H-pyran-5-yl)-2,3,6,7,8,9,10,11,12,13,14,15,16,17-tetradecahydro-1H-cyclopenta[a]phenanthren-3-yl)-3-(2-(2-oxopiperazin-1-yl)ethyl)urea, 1-((3S,8R,9S,10R,13R,14S,17R)-14-hydroxy-10,13-dimethyl-17-(2-oxo-2H-pyran-5-yl)-2,3,6,7,8,9,10,11,12,13,14,15,16,17-tetradecahydro-1H-cyclopenta[a]phenanthren-3-yl)-3-(2-(4-methyl-2-oxopiperazin-1-yl)ethyl)urea, 1-((3S,8R,9S,10R,13R,14S,17R)-14-hydroxy-10,13-dimethyl-17-(2-oxo-2H-pyran-5-yl)-2,3,6,7,8,9,10,11,12,13,14,15,16,17-tetradecahydro-1H-cyclopenta[a]phenanthren-3-yl)-3-(2-(3-oxopiperazin-1-yl)ethyl)urea, 1-((3S,8R,9S,10R,13R,14S,17R)-14-hydroxy-10,13-dimethyl-17-(2-oxo-2H-pyran-5-yl)-2,3,6,7,8,9,10,11,12,13,14,15,16,17-tetradecahydro-1H-cyclopenta[a]phenanthren-3-yl)-3-(2-((S)-3-hydroxypyrrolidin-1-yl)ethyl)urea, 1-((3S,8R,9S,10R,13R,14S,17R)-14-hydroxy-10,13-dimethyl-17-(2-oxo-2H-pyran-5-yl)-2,3,6,7,8,9,10,11,12,13,14,15,16,17-tetradecahydro-1H-cyclopenta[a]phenanthren-3-yl)-3-(2-((R)-3-hydroxypyrrolidin-1-yl)ethyl)urea, 2-(pyrrolidin-1-yl)ethyl ((1R,2aR,3aS,3bR,5aR,7S,9aS,9bS,11aR)-9a,11a-dimethyl-1-(2-oxo-2H-pyran-5-yl)hexadecahydronaphtho[1',2':6,7]indeno[1,7a-b]oxiren-7-yl)carbamate, 2-morpholinoethyl ((1R,2aR,3aS,3bR,5aR,7S,9aS,9bS,11aR)-9a,11a-dimethyl-1-(2-oxo-2H-pyran-5-yl)hexadecahydronaphtho[1',2':6,7]indeno[1,7a-b]oxiren-7-yl)carbamate, 2-(3-oxopiperazin-1-yl)ethyl ((1R,2aR,3aS,3bR,5aR,7S,9aS,9bS,11aR)-9a,11a-dimethyl-1-(2-oxo-2H-pyran-5-yl)hexadecahydronaphtho[1',2':6,7]indeno[1,7a-b]oxiren-7-yl)carbamate, 1-((1R,2aR,3aS,3bR,5aR,7S,9aS,9bS,11aR)-9a,11a-dimethyl-1-(2-oxo-2H-pyran-5-yl)hexadecahydronaphtho[1',2':6,7]indeno[1,7a-b]oxiren-7-yl)-3-methylurea, 1-((1R,2aR,3aS,3bR,5aR,7S,9aS,9bS,11aR)-9a,11a-dimethyl-1-(2-oxo-2H-pyran-5-yl)hexadecahydronaphtho[1',2':6,7]indeno[1,7a-b]oxiren-7-yl)-3-(2-(pyrrolidin-1-yl)ethyl)urea, 1-((1R,2aR,3aS,3bR,5aR,7S,9aS,9bS,11aR)-9a,11a-dimethyl-1-(2-oxo-2H-pyran-5-yl)hexadecahydronaphtho[1',2':6,7]indeno[1,7a-b]oxiren-7-yl)-3-(2-morpholinoethyl)urea, N-((1R,2aR,3aS,3bR,5aR,7S,9aS,9bS,11aR)-9a,11a-dimethyl-1-(2-oxo-2H-pyran-5-yl)hexadecahydronaphtho[1',2':6,7]indeno[1,7a-b]oxiren-7-yl)-4-methylpiperazine-1-carboxamide, 1-((1R,2aR,3aS,3bR,5aR,7S,9aS,9bS,11aR)-9a,11a-dimethyl-1-(2-oxo-2H-pyran-5-yl)hexadecahydronaphtho[1',2':6,7]indeno[1,7a-b]oxiren-7-yl)-3-(2-(4-methylpiperazin-1-yl)ethyl)urea, N-((1R,2aR,3aS,3bR,5aR,7S,9aS,9bS,11aR)-9a,11a-dimethyl-1-(2-oxo-2H-pyran-5-yl)hexadecahydronaphtho[1',2':6,7]indeno[1,7a-b]oxiren-7-yl)-4-methyl-1,4-diazepane-1-carboxamide, N-((1R,3aS,3bR,5aR,7S,9aS,9bS,11aR)-9a,11a-dimethyl-1-(2-oxo-2H-pyran-5-yl)hexadecahydronaphtho[1',2':6,7]indeno[1,7a-b]oxiren-7-yl)morpholine-4-carboxamide, 1-((1R,2aR,3aS,3bR,5aR,7S,9aS,9bS,11aR)-9a,11a-dimethyl-1-(2-oxo-2H-pyran-5-yl)hexadecahydronaphtho[1',2':6,7]indeno[1,7a-b]oxiren-7-yl)-3-(2-(3-oxopiperazin-1-yl)ethyl)urea, (1R,2R,2aR,3aS,3bR,5aR,7S,9aS,9bS,11aR)-9a,11a-dimethyl-1-(2-oxo-2H-pyran-5-yl)-7-(((2-(pyrrolidin-1-yl)ethoxy)carbonyl)amino)hexadecahydronaphtho[1',2':6,7]indeno[1,7a-b]oxiren-2-yl acetate, (1R,2R,2aR,3aS,3bR,5aR,7S,9aS,9bS,11aR)-9a,11a-dimethyl-7-(((2-morpholinoethoxy)carbonyl)amino)-1-(2-oxo-2H-pyran-5-yl)hexadecahydronaphtho[1',2':6,7]indeno[1,7a-b]oxiren-2-yl acetate, (1R,2R,2aR,3aS,3bR,5aR,7S,9aS,9bS,11aR)-9a,11a-dimethyl-1-(2-oxo-2H-pyran-5-yl)-7-(((2-(3-oxopiperazin-1-yl)ethoxy)carbonyl)amino)hexadecahydronaphtho[1',2':6,7]indeno[1,7a-b]oxiren-2-yl acetate, (1R,2R,2aR,3aS,3bR,5aR,7S,9aS,9bS,11aR)-9a,11a-dimethyl-1-(2-oxo-2H-pyran-5-yl)-7-(3-(2-(pyrrolidin-1-yl)ethyl)ureido)hexadecahydronaphtho[1',2':6,7]indeno[1,7a-b]oxiren-2-yl acetate, (1R,2R,2aR,3aS,3bR,5aR,7S,9aS,9bS,11aR)-9a,11a-dimethyl-7-(3-(2-morpholinoethyl)ureido)-1-(2-oxo-2H-pyran-5-yl)hexadecahydronaphtho[1',2':6,7]indeno[1,7a-b]oxiren-2-yl acetate, (1R,2R,2aR,3aS,3bR,5aR,7S,9aS,9bS,11aR)-9a,11a-dimethyl-7-(4-methylpiperazine-1-carboxamido)-1-(2-oxo-2H-pyran-5-yl)hexadecahydronaphtho[1',2':6,7]indeno[1,7a-b]oxiren-2-yl acetate, (1R,2R,2aR,3aS,3bR,5aR,7S,9aS,9bS,11aR)-9a,11a-dimethyl-7-(3-(2-(4-methylpiperazin-1-yl)ethyl)ureido)-1-(2-oxo-2H-pyran-5-yl)hexadecahydronaphtho[1',2':6,7]indeno[1,7a-b]oxiren-2-yl acetate, (1R,2R,2aR,3aS,3bR,5aR,7S,9aS,9bS,11aR)-9a,11a-dimethyl-7-(morpholine-4-carboxamido)-1-(2-oxo-2H-pyran-5-yl)hexadecahydronaphtho[1',2':6,7]indeno[1,7a-b]oxiren-2-yl acetate, (1R,2R,2aR,3aS,3bR,5aR,7S,9aS,9bS,11aR)-9a,11a-dimethyl-7-(4-methyl-1,4-diazepane-1-carboxamido)-1-(2-oxo-2H-pyran-5-yl)hexadecahydronaphtho[1',2':6,7]indeno[1,7a-b]oxiren-2-yl acetate, (1R,2R,2aR,3aS,3bR,5aR,7S,9aS,9bS,11aR)-9a,11a-dimethyl-1-(2-oxo-2H-pyran-5-yl)-7-(3-oxopiperazine-1-carboxamido)hexadecahydronaphtho[1',2':6,7]indeno[1,7a-b]oxiren-2-yl acetate, (1R,2R,2aR,3aS,3bR,5aR,7S,9aS,9bS,11aR)-9a,11a-dimethyl-7-(3-(2-(4-methyl-2-oxopiperazin-1-yl)ethyl)ureido)-1-(2-oxo-2H-pyran-5-yl)hexadecahydronaphtho[1',2':6,7]indeno[1,7a-b]oxiren-2-yl acetate, (1R,2R,2aR,3aS,3bR,5aR,7S,9aS,9bS,11aR)-9a,11a-dimethyl-1-(2-oxo-2H-pyran-5-yl)-7-(3-(2-(3-oxopiperazin-1-yl)ethyl)ureido)hexadecahydronaphtho[1',2':6,7]indeno[1,7a-b]oxiren-2-yl acetate, (1R,2R,2aR,3aS,3bR,5aS,7S,9aR,9bS,11aR)-5a-hydroxy-9a,11a-dimethyl-1-(2-oxo-2H-pyran-5-yl)-7-(((2-(pyrrolidin-1-yl)ethoxy)carbonyl)amino)hexadecahydronaphtho[1',2':6,7]indeno[1,7a-b]oxiren-2-yl acetate, (1R,2R,2aR,3aS,3bR,5aS,7S,9aR,9bS,11aR)-5a-hydroxy-9a,11a-dimethyl-7-(((2-morpholinoethoxy)carbonyl)amino)-1-(2-oxo-2H-pyran-5-yl)hexadecahydronaphtho[1',2':6,7]indeno[1,7a-b]oxiren-2-yl acetate, (1R,2R,2aR,3aS,3bR,5aS,7S,9aR,9bS,11aR)-5a-hydroxy-9a,11a-dimethyl-1-(2-oxo-2H-pyran-5-yl)-7-(((2-(3-oxopiperazin-1-yl)ethoxy)carbonyl)amino)hexadecahydronaphtho[1',2':6,7]indeno[1,7a-b]oxiren-2-yl acetate, (1R,2R,2aR,3aS,3bR,5aS,7S,9aR,9bS,11aR)-5a-hydroxy-9a,11a-dimethyl-1-(2-oxo-2H-pyran-5-yl)-7-(3-(2-(pyrrolidin-1-yl)ethyl)ureido)hexadecahydronaphtho[1',2':6,7]indeno[1,7a-b]oxiren-2-yl acetate, (1R,2R,2aR,3aS,3bR,5aS,7S,9aR,9bS,11aR)-5a-hydroxy-9a,11a-dimethyl-7-(3-(2-morpholinoethyl)ureido)-1-(2-oxo-2H-pyran-5-yl)hexadecahydronaphtho[1',2':6,7]indeno[1,7a-b]oxiren-2-yl acetate, (1R,2R,2aR,3aS,3bR,5aS,7S,9aR,9bS,11aR)-5a-hydroxy-9a,11a-dimethyl-7-(4-methylpiperazine-1-carboxamido)-1-(2-oxo-2H-pyran-5-yl)hexadecahydronaphtho[1',2':6,7]indeno[1,7a-b]oxiren-2-yl acetate, (1R,2R,2aR,3aS,3bR,5aS,7S,9aR,9bS,11aR)-5a-hydroxy-9a,11a-dimethyl-7-(3-(2-(4-methylpiperazin-1-yl)ethyl)ureido)-1-(2-oxo-2H-pyran-5-yl)hexadecahydronaphtho[1',2':6,7]indeno[1,7a-b]oxiren-2-yl acetate, (1R,2R,2aR,3aS,3bR,5aS,7S,9aR,9bS,11aR)-5a-hydroxy-9a,11a-dimethyl-7-(morpholine-4-carboxamido)-1-(2-oxo-2H-pyran-5-yl)hexadecahydronaphtho[1',2':6,7]indeno[1,7a-b]oxiren-2-yl acetate, (1R,2R,2aR,3aS,3bR,5aS,7S,9aR,9bS,11aR)-5a-hydroxy-9a,11a-dimethyl-1-(2-oxo-2H-pyran-5-yl)-7-(3-oxopiperazine-1-carboxamido)hexadecahydronaphtho[1',2':6,7]indeno[1,7a-b]oxiren-2-yl acetate, (1R,2R,2aR,3aS,3bR,5aS,7S,9aR,9bS,11aR)-5a-hydroxy-9a,11a-dimethyl-7-(3-(2-(4-methyl-2-oxopiperazin-1-yl)ethyl)ureido)-1-(2-oxo-2H-pyran-5-yl)hexadecahydronaphtho[1',2':6,7]indeno[1,7a-b]oxiren-2-yl acetate, (1R,2R,2aR,3aS,3bR,5aS,7S,9aR,9bS,11aR)-5a-hydroxy-9a,11a-dimethyl-1-(2-oxo-2H-pyran-5-yl)-7-(3-(2-(3-oxopiperazin-1-yl)ethyl)ureido)hexadecahydronaphtho[1',2':6,7]indeno[1,7a-b]oxiren-2-yl acetate, 2-aminoethyl ((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)carbamate, 2-hydroxyethyl ((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)carbamate, 2-(3-oxopiperazin-1-yl)ethyl ((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)carbamate, 2-(pyrrolidin-1-yl)ethyl ((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)carbamate, 2-morpholinoethyl ((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)carbamate, 1-(2-aminoethyl)-3-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)urea, 1-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-3-(2-hydroxyethyl)urea, 1-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-3-(2-(pyrrolidin-1-yl)ethyl)urea, 1-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-3-(2-morpholinoethyl)urea, N-((5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)piperazine-1-carboxamide, N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)piperazine-1-carboxamide, (R)—N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-3-(hydroxymethyl)piperazine-1-carboxamide, (S)—N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-3-(hydroxymethyl)piperazine-1-carboxamide, (S)—N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-2-(hydroxymethyl)piperazine-1-carboxamide, (R)—N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-2-(hydroxymethyl)piperazine-1-carboxamide, 1-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-3-(2-(piperazin-1-yl)ethyl)urea, N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)morpholine-4-carboxamide, 4-(3-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)ureido)butanoic acid, N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-4-methylpiperazine-1-carboxamide, N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-1,4-diazepane-1-carboxamide, N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-4-methyl-1,4-diazepane-1-carboxamide, N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-3-oxopiperazine-1-carboxamide, (S)-3-hydroxy-N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)pyrrolidine-1-carboxamide, (R)-3-hydroxy-N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)pyrrolidine-1-carboxamide, 1-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-3-(2-(2-oxopiperazin-1-yl)ethyl)urea, 1-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-3-(2-(4-methyl-2-oxopiperazin-1-yl)ethyl)urea, 1-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-3-(2-(3-oxopiperazin-1-yl)ethyl)urea, 1-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-3-(2-((S)-3-hydroxypyrrolidin-1-yl)ethyl)urea, 1-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-3-(2-((R)-3-hydroxypyrrolidin-1-yl)ethyl)urea, 2-amino-N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)acetamide, (R)-2-amino-N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)propanamide, (S)-2-amino-N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)propanamide, (R)-2-amino-N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-3-methylbutanamide, (S)-2-amino-N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-3-methylbutanamide, (R)-2-amino-N1-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)succinamide, (S)-2-amino-N1-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)succinamide, 2-(pyrrolidin-1-yl)ethyl ((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)carbamate, 2-morpholinoethyl ((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)carbamate, 2-(3-oxopiperazin-1-yl)ethyl ((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)carbamate, 1-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)-3-(2-(pyrrolidin-1-yl)ethyl)urea, 1-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)-3-(2-morpholinoethyl)urea, N-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)piperazine-1-carboxamide, 1-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)-3-(2-(piperazin-1-yl)ethyl)urea, N-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)morpholine-4-carboxamide 4-(3-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)ureido)butanoic acid N-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)-4-methylpiperazine-1-carboxamide, N-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)-1,4-diazepane-1-carboxamide, N-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)-4-methyl-1,4-diazepane-1-carboxamide, (S)—N-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)-3-hydroxypyrrolidine-1-carboxamide, (R)—N-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)-3-hydroxypyrrolidine-1-carboxamide, 1-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)-3-(2-(2-oxopiperazin-1-yl)ethyl)urea, 1-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)-3-(2-(3-oxopiperazin-1-yl)ethyl)urea, 1-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)-3-(2-((S)-3-hydroxypyrrolidin-1-yl)ethyl)urea, 1-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)-3-(2-((R)-3-hydroxypyrrolidin-1-yl)ethyl)urea, (3S,5R,8R,9S,10S,13R,14S,16S,17R)-14-hydroxy-10,13-dimethyl-17-(5-oxo-2,5-dihydrofuran-3-yl)-3-(((2-(pyrrolidin-1-yl)ethoxy)carbonyl)amino)hexadecahydro-1H-cyclopenta[a]phenanthren-16-yl acetate, (3S,5R,8R,9S,10S,13R,14S,16S,17R)-14-hydroxy-10,13-dimethyl-3-(((2-morpholinoethoxy)carbonyl)amino)-17-(5-oxo-2,5-dihydrofuran-3-yl)hexadecahydro-1H-cyclopenta[a]phenanthren-16-yl acetate, (3S,5R,8R,9S,10S,13R,14S,16S,17R)-14-hydroxy-10,13-dimethyl-17-(5-oxo-2,5-dihydrofuran-3-yl)-3-(((2-(3-oxopiperazin-1-yl)ethoxy)carbonyl)amino)hexadecahydro-1H-cyclopenta[a]phenanthren-16-yl acetate, (3S,5R,8R,9S,10S,13R,14S,16S,17R)-14-hydroxy-10,13-dimethyl-17-(5-oxo-2,5-dihydrofuran-3-yl)-3-(3-(2-(pyrrolidin-1-yl)ethyl)ureido)hexadecahydro-1H-cyclopenta[a]phenanthren-16-yl acetate, (3S,5R,8R,9S,10S,13R,14S,16S,17R)-14-hydroxy-10,13-dimethyl-3-(3-(2-morpholinoethyl)ureido)-17-(5-oxo-2,5-dihydrofuran-3-yl)hexadecahydro-1H-cyclopenta[a]phenanthren-16-yl acetate, (3S,5R,8R,9S,10S,13R,14S,16S,17R)-14-hydroxy-10,13-dimethyl-17-(5-oxo-2,5-dihydrofuran-3-yl)-3-(piperazine-1-carboxamido)hexadecahydro-1H-cyclopenta[a]phenanthren-16-yl acetate, (3S,5R,8R,9S,10S,13R,14S,16S,17R)-14-hydroxy-10,13-dimethyl-17-(5-oxo-2,5-dihydrofuran-3-yl)-3-(3-(2-(piperazin-1-yl)ethyl)ureido)hexadecahydro-1H-cyclopenta[a]phenanthren-16-yl acetate, (3S,5R,8R,9S,10S,13R,14S,16S,17R)-14-hydroxy-10,13-dimethyl-3-(morpholine-4-carboxamido)-17-(5-oxo-2,5-dihydrofuran-3-yl)hexa decahydro-1H-cyclopenta[a]phenanthren-16-yl acetate, 4-(3-((3S,5R,8R,9S,10S,13R,14S,16S,17R)-16-acetoxy-14-hydroxy-10,13-dimethyl-17-(5-oxo-2,5-dihydrofuran-3-yl)hexadecahydro-1H-cyclopenta[a]phenanthren-3-yl)ureido)butanoic acid (3S,5R,8R,9S,10S,13R,14S,16S,17R)-14-hydroxy-10,13-dimethyl-3-(4-methylpiperazine-1-carboxamido)-17-(5-oxo-2,5-dihydrofuran-3-yl)hexadecahydro-1H-cyclopenta[a]phenanthren-16-yl acetate, (3S,5R,8R,9S,10S,13R,14S,16S,17R)-3-(1,4-diazepane-1-carboxamido)-14-hydroxy-10,13-dimethyl-17-(5-oxo-2,5-dihydrofuran-3-yl)hexadecahydro-1H-cyclopenta[a]phenanthren-16-yl acetate, (3S,5R,8R,9S,10S,13R,14S,16S,17R)-14-hydroxy-10,13-dimethyl-3-(4-methyl-1,4-diazepane-1-carboxamido)-17-(5-oxo-2,5-dihydrofuran-3-yl)hexadecahydro-1H-cyclopenta[a]phenanthren-16-yl acetate, (3S,5R,8R,9S,10S,13R,14S,16S,17R)-14-hydroxy-10,13-dimethyl-17-(5-oxo-2,5-dihydrofuran-3-yl)-3-(3-(2-(2-oxopiperazin-1-yl)ethyl)ureido)hexadecahydro-1H-cyclopenta[a]phenanthren-16-yl acetate, (3S,5R,8R,9S,10S,13R,14S,16S,17R)-14-hydroxy-10,13-dimethyl-17-(5-oxo-2,5-dihydrofuran-3-yl)-3-(3-(2-(3-oxopiperazin-1-yl)ethyl)ureido)hexadecahydro-1H-cyclopenta[a]phenanthren-16-yl acetate, 2-(pyrrolidin-1-yl)ethyl ((3S,5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)carbamate, 2-morpholinoethyl ((3S,5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)carbamate, 2-(3-oxopiperazin-1-yl)ethyl ((3S,5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)carbamate, 1-((3S,5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)-3-(2-(pyrrolidin-1-yl)ethyl)urea, 1-((3S,5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)-3-(2-morpholinoethyl)urea, N-((3S,5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)morpholine-4-carboxamide, 4-(3-((3S,5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)ureido)butanoic acid N-((5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)piperazine-1-carboxamide, N-((3S,5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)piperazine-1-carboxamide, (R)—N-((3S,5R,8R,9S,10S,13R,17S)-10,13-dimethyl-17-(2-oxo-2H-pyran-5-yl)-2,3,4,5,6,7,8,9,10,11,12,13,16,17- tetradecahydro-1H-cyclopenta[a]phenanthren-3-yl)-3-(hydroxymethyl)piperazine-1-carboxamide, (S)—N-((3S,5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)-3-(hydroxymethyl)piperazine-1-carboxamide, (S)—N-((3S,5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)-2-(hydroxymethyl)piperazine-1-carboxamide, (R)—N-((3S,5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)-2-(hydroxymethyl)piperazine-1-carb oxamide, N-((3S,5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)-1,4-diazepane-1-carboxamide, 1-((3S,5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)3 oxopiperazin-1-yl)ethyl)urea, 1-((3S,5R,8R,9S,10S,13R,17S)-10,13-dimethyl-17-(2-oxo-2H-pyran-5-yl)-2,3,4,5,6,7,8,9,10,11,12,13,16,17-tetradH-cyclopenta[a]phenanthren-3-yl)-3-(2-(3-oxopiperazin-piperazin-1-yl)ethyl)urea, 1-((3S,5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)-3-(2-((S)-3-hydroxypyrrolidin-1-yl)ethyl)urea, 1-((3S,5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)-3-(2-((R)-3-hydroxypyrrolidin-1-yl)ethyl)urea, N-((3S,5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)-2-(pyrrolidin-1-yl)acetamide, N-((3S,5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)-2-morpholinoacetamide, (R)-2-amino-N-((3S,5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)propanamide (S)-2-amino-N-((3S,5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)propanamide, (R)-2-amino-N-((3S,5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)-3-methylbutanamide, (S)-2-amino-N-((3S,5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)-3-methylbutanamide, (R)-2-amino-N1-((3S,5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)succinamide, (S)-2-amino-N1-((3S,5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)succinamide, 2-(3-oxopiperazin-1-yl)ethyl ((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)carbamate, 2-(pyrrolidin-1-yl)ethyl ((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)carbamate, 2-morpholinoethyl ((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)carbamate, 1-(2-aminoethyl)-3-((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)urea, 1-((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)-3-(2-hydroxyethyl)urea, 1-((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)-3-(2-(pyrrolidin-1-yl)ethyl)urea, 1-((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)-3-(2-morpholinoethyl)urea, N-((5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)piperazine-1-carboxamide, N-((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)piperazine-1-carboxamide, (R)—N-((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)-3-(hydroxymethyl)piperazine-1-carb oxamide, (S)—N-((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)-3-(hydroxymethyl)piperazine-1-carboxamide, (S)—N-((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)-2-(hydroxymethyl)piperazine-1-carboxamide, (R)—N-((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)-2-(hydroxymethyl)piperazine-1-carboxamide, 1-((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)-3-(2-(piperazin-1-yl)ethyl)urea, N-((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)morpholine-4-carboxamide, 4-(3-((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)ureido)butanoic acid, N-((3S,5R,8R,9S,10S,13R,17S)-10,13-dimethyl-17-(5-oxo-2,5-dihydrofuran-3-yl)-2,3,4,5,6,7,8,9,10,11,12,13,16,17- tetradecahydro-1H-cyclopenta[a]phenanthren-3-yl)-4-methylpiperazine-1-carboxamide, N-((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)-1,4-diazepane-1-carboxamide, (S)—N-((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)-3-hydroxypyrrolidine-1-carboxamide, (R)—N-((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)-3-hydroxypyrrolidine-1-carboxamide, 1-((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)-3-(2-(2-oxopiperazin-1-yl)ethyl)urea, 1-((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)-3-(2-(3-oxopiperazin-1-yl)ethyl)urea, 1-((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)-3-(2-((S)-3-hydroxypyrrolidin-1-yl)ethyl)urea, 1-((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)-3-(2-((R)-3-hydroxypyrrolidin-1-yl)ethyl)urea, 2-amino-N-((3S,5R,8R,9S,10S,13R,17 S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)acetamide, (2R)-2-amino-N-((3S,5R,8R,9S,10S,13R,17S)-10,13-dimethyl-17-(5-oxo-2,5-dihydrofuran-3-yl)hexadecahydro-1H-cyclopenta[a]phenanthren-3-yl)propanamide, (S)-2-amino-N-((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)propanamide, (R)-2-amino-N-((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)-3-methylbutanamide, (S)-2-amino-N-((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)-3-methylbutanamide, (R)-2-amino-N1-((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)succinamide, (5)-2-amino-N1-((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)succinamide, (R)—N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)pyrrolidine-2-carboxamide, (S)—N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)pyrrolidine-2-carboxamide, (S)—N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)pyrrolidine-3-carboxamide, (R)—N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)pyrrolidine-3-carboxamide, 5-((3R,5R,8R,9S,10S,13R,14S,17R)-3-amino-14-hydroxy-10,13-dimethylhexa decahydro-1H-cyclopenta[a]phenanthren-17-yl)-2H-pyran-2-one, 5-((3S,5R,8R,9S,10S,13R,14S,17R)-3-amino-14-hydroxy-10,13-dimethylhexadecahydro-1H-cyclopenta[a]phenanthren-17-yl)-2H-pyran-2-one, 5-((3S,5R,8R,9S,10S,13R,14S,17R)-14-hydroxy-10,13-dimethyl-3-(pyrrolidin-1-yl)hexadecahydro-1H-cyclopenta[a]phenanthren-17-yl)-2H-pyran-2-one, 5-((3S,5R,8R,9S,10S,13R,14S,17R)-14-hydroxy-10,13-dimethyl-3-(piperazin-1-yl)hexadecahydro-1H-cyclopenta[a]phenanthren-17-yl)-2H-pyran-2-one, 5-((3S,5R,8R,9S,10S,13R,14S,17R)-14-hydroxy-10,13-dimethyl-3-((2-(pyrrolidin-1-yl)ethyl)amino)hexadecahydro-1H-cyclopenta[a]phenanthren-17-yl)-2H-pyran-2-one, 5-((3S,5R,8R,9S,10S,13R,14S,17R)-14-hydroxy-10,13-dimethyl-3-morpholinohexadecahydro-1H-cyclopenta[a]phenanthren-17-yl)-2H-pyran-2-one, 5-((3S,5R,8R,9S,10S,13R,14S,17R)-14-hydroxy-10,13-dimethyl-3-((2-morpholinoethyl)amino)hexadecahydro-1H-cyclopenta[a]phenanthren-17-yl)-2H-pyran-2-one, 4-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)piperazin-2-one, 5-((3S,5R,8R,9S,10S,13R,14S,17R)-14-hydroxy-3-((2-hydroxyethyl)(methyl)amino)-10,13-dimethylhexa decahydro-1H-cyclopenta[a]phenanthren-17-yl)-2H-pyran-2-one, N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)piperazine-1-carboxamide, N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)pyrrolidine-1-carboxamide, N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)pyrrolidine-1-carboxamide, 1-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-(2-hydroxyethyl)urea, 1-(2-aminoethyl)-3-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)urea, N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)morpholine-4-carboxamide, N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N-methylmorpholine-4-carboxamide, methyl ((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)carbamate, methyl ((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)(methyl)carbamate, N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)methanesulfonamide, 2-amino-N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)acetamide, (R)-2-amino-N-((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)-3-methylbutanamide, (R)-2-amino-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N,3-dimethylbutanamide, (R)-2-amino-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)propanamide, (S)—N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)pyrrolidine-2-carboxamide, (R)—N-((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)pyrrolidine-2-carboxamide, 5-((5R,8R,9S,10S,13R,14S,17R)-14-hydroxy-10,13-dimethyl-3-(piperazin-1-yl)hexadecahydro-1H-cyclopenta[a]phenanthren-17-yl)-2H-pyran-2-one, 5-((5R,8R,9S,10S,13R,14S,17R)-14-hydroxy-10,13-dimethyl-3-((2-morpholinoethyl)amino)hexadecahydro-1H-cyclopenta[a]phenanthren-17-yl)-2H-pyran-2-one, 4-((5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)piperazin-2-one, 5-((5R,8R,9S,10S,13R,14S,17R)-14-hydroxy-10,13-dimethyl-3-(pyrrolidin-1-yl)hexadecahydro-1H-cyclopenta[a]phenanthren-17-yl)-2H-pyran-2-one, methyl ((5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)(methyl)carbamate, (2R)-2-amino-N-((5R,8R,9S,10S,13R,14S,17R)-14-hydroxy-10,13-dimethyl-17-(2-oxo-2H-pyran-1-yl)hexadecahydro-1H-cyclopenta[a]phenanthren-3-yl)-N,3-dimethylbutanamide, N-((5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N-methylmorpholine-4-carboxamide, 5-((5R,8R,9S,10S,13R,14S,17R)-14-hydroxy-10,13-dimethyl-3-((2-(pyrrolidin-1-yl)ethyl)amino)hexadecahydro-1H-cyclopenta[a]phenanthren-17-yl)-2H-pyran-2-one, 5-((5R,8R,9S,10S,13R,14S,17R)-14-hydroxy-10,13-dimethyl-3-morpholinohexadecahydro-1H-cyclopenta[a]phenanthren-17-yl)-2H-pyran-2-one, (2R)-2-amino-N-((5 S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)-3-methylbutanamide, N-((5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)morpholine-4-carboxamide, (2R)—N-((5 S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)pyrrolidine-2-carboxamide, 5-((5R,8R,9S,10S,13R,14S,17R)-14-hydroxy-3-((2-hydroxyethyl)(methyl)amino)-10,13-dimethylhexadecahydro-1H-cyclopenta[a]phenanthren-17-yl)-2H-pyran-2-one, 5-((3S,5R,8R,9S,10S,13R,14S,17R)-14-hydroxy-10,13-dimethyl-3-((1-methylpiperidin-4-yl)amino)hexadecahydro-1H-cyclopenta[a]phenanthren-17-yl)-2H-pyran-2-one, 5-((3S,5R,8R,9S,10S,13R,14S,17R)-3-(((3R)-3-fluoropiperidin-4-yl)amino)-14-hydroxy-10,13-dimethylhexadecahydro-1H-cyclopenta[a]phenanthren-17-yl)-2H-pyran-2-one, 5-((3S,5R,8R,9S,10S,13R,14S,17R)-3-(((3S)-3-fluoropiperidin-4-yl)amino)-14-hydroxy-10,13-dimethylhexadecahydro-1H-cyclopenta[a]phenanthren-17-yl)-2H-pyran-2-one, 5-((3S,5R,8R,9S,10S,13R,14S,17R)-3-(((3R)-3-fluoropiperidin-4-yl)(methyl)amino)-14-hydroxy-10,13-dimethylhexadecahydro-1H-cyclopenta[a]phenanthren-17-yl)-2H-pyran-2-one, 5-((3S,5R,8R,9S,10S,13R,14S,17R)-3-(((3 S)-3-fluoropiperidin-4-yl)(methyl)amino)-14-hydroxy-10,13-dimethylhexadecahydro-1H-cyclopenta[a]phenanthren-17-yl)-2H-pyran-2-one, 5-((3S,5R,8R,9S,10S,13R,14S,17R)-3-(((3R)-3-fluoro-1-methylpiperidin-4-yl)(methyl)amino)-14-hydroxy-10,13-dimethylhexadecahydro-1H-cyclopenta[a]phenanthren-17-yl)-2H-pyran-2-one, 5-((3S,5R,8R,9S,10S,13R,14S,17R)-3-(((3 S)-3-fluoro-1-methylpiperidin-4-yl)(methyl)amino)-14-hydroxy-10,13-dimethylhexadecahydro-1H-cyclopenta[a]phenanthren-17-yl)-2H-pyran-2-one, 5-((3S,5R,8R,9S,10S,13R,14S,17R)-3-(((3R)-3-fluoro-1-methylpiperidin-4-yl)amino)-14-hydroxy-10,13-dimethylhexadecahydro-1H-cyclopenta[a]phenanthren-17-yl)-2H-pyran-2-one, 5-((3S,5R,8R,9S,10S,13R,14S,17R)-3-(((3 S)-3-fluoro-1-methylpiperidin-4-yl)amino)-14-hydroxy-10,13-dimethylhexadecahydro-1H-cyclopenta[a]phenanthren-17-yl)-2H-pyran-2-one, 5-((3S,5R,8R,9S,10S,13R,14S,17R)-14-hydroxy-10,13-dimethyl-3-(piperidin-4-ylamino)hexadecahydro-1H-cyclopenta[a]phenanthren-17-yl)-2H-pyran-2-one, 5-((3S,5R,8R,9S,10S,13R,14S,17R)-14-hydroxy-10,13-dimethyl-3-(methyl(1-methylpiperidin-4-yl)amino)hexadecahydro-1H-cyclopenta[a]phenanthren-17-yl)-2H-pyran-2-one, 5-((3S,5R,8R,9S,10S,13R,14S,17R)-14-hydroxy-10,13-dimethyl-3-(methyl(piperidin-4-yl)amino)hexadecahydro-1H-cyclopenta[a]phenanthren-17-yl)-2H-pyran-2-one, 5-((3S,5R,8R,9S,10S,13R,14S,17R)-3-(4-aminopiperidin-1-yl)-14-hydroxy-10,13-dimethylhexadecahydro-1H-cyclopenta[a]phenanthren-17-yl)-2H-pyran-2-one, 5-((3S,5R,8R,9S,10S,13R,14S,17R)-14-hydroxy-3-(4-hydroxypiperidin-1-yl)-10,13-dimethylhexadecahydro-1H-cyclopenta[a]phenanthren-17-yl)-2H-pyran-2-one, 5-((3S,5R,8R,9S,10S,13R,14S,17R)-14-hydroxy-3-(3-hydroxypiperidin-1-yl)-10,13-dimethylhexadecahydro-1H-cyclopenta[a]phenanthren-17-yl)-2H-pyran-2-one, 5-((3S,5R,8R,9S,10S,13R,14S,17R)-3-(3-aminopiperidin-1-yl)-14-hydroxy-10,13-dimethylhexadecahydro-1H-cyclopenta[a]phenanthren-17-yl)-2H-pyran-2-one, 5-((3S,5R,8R,9S,10S,13R,14S,17R)-3-((S)-3-(aminomethyl)morpholino)-14-hydroxy-10,13-dimethylhexadecahydro-1H-cyclopenta[a]phenanthren-17-yl)-2H-pyran-2-one, 5-((3S,5R,8R,9S,10S,13R,14S,17R)-3-((R)-3-(aminomethyl)morpholino)-14-hydroxy-10,13-dimethylhexadecahydro-1H-cyclopenta[a]phenanthren-17-yl)-2H-pyran-2-one, 5-((3S,5R,8R,9S,10S,13R,14S,17R)-14-hydroxy-3-((R)-3-(hydroxymethyl)morpholino)-10,13-dimethylhexadecahydro-1H-cyclopenta[a]phenanthren-17-yl)-2H-pyran-2-one, 5-((3S,5R,8R,9S,10S,13R,14S,17R)-14-hydroxy-3-((S)-3-(hydroxymethyl)morpholino)-10,13-dimethylhexadecahydro-1H-cyclopenta[a]phenanthren-17-yl)-2H-pyran-2-one, 5-((3S,5R,8R,9S,10S,13R,14S,17R)-14-hydroxy-3-((R)-2-(hydroxymethyl)morpholino)-10,13-dimethylhexadecahydro-1H-cyclopenta[a]phenanthren-17-yl)-2H-pyran-2-one, 5-((3S,5R,8R,9S,10S,13R,14S,17R)-3-((S)-2-(aminomethyl)morpholino)-14-hydroxy-10,13-dimethylhexadecahydro-1H-cyclopenta[a]phenanthren-17-yl)-2H-pyran-2-one, 5-((3S,5R,8R,9S,10S,13R,14S,17R)-3-((R)-2-(aminomethyl)morpholino)-14-hydroxy-10,13-dimethylhexadecahydro-1H-cyclopenta[a]phenanthren-17-yl)-2H-pyran-2-one, 5-((3S,5R,8R,9S,10S,13R,14S,17R)-14-hydroxy-3-((S)-2-(hydroxymethyl)morpholino)-10,13-dimethylhexadecahydro-1H-cyclopenta[a]phenanthren-17-yl)-2H-pyran-2-one, 5-((3S,5R,8R,9S,10S,13R,14S,17R)-14-hydroxy-3-((S)-2-(hydroxymethyl)pyrrolidin-1-yl)-10,13-dimethylhexadecahydro-1H-cyclopenta[a]phenanthren-17-yl)-2H-pyran-2-one, 5-((3S,5R,8R,9S,10S,13R,14S,17R)-14-hydroxy-3-((R)-2-(hydroxymethyl)pyrrolidin-1-yl)-10,13-dimethylhexadecahydro-1H-cyclopenta[a]phenanthren-17-yl)-2H-pyran-2-one, 5-((3S,5R,8R,9S,10S,13R,14S,17R)-3-((S)-2-(aminomethyl)pyrrolidin-1-yl)-14-hydroxy-10,13-dimethylhexadecahydro-1H-cyclopenta[a]phenanthren-17-yl)-2H-pyran-2-one, 5-((3S,5R,8R,9S,10S,13R,14S,17R)-3-((R)-2-(aminomethyl)pyrrolidin-1-yl)-14-hydroxy-10,13-dimethylhexadecahydro-1H-cyclopenta[a]phenanthren-17-yl)-2H-pyran-2-one, 5-((3S,5R,8R,9S,10S,13R,14S,17R)-14-hydroxy-3-((S)-3-hydroxypyrrolidin-1-yl)-10,13-dimethylhexadecahydro-1H-cyclopenta[a]phenanthren-17-yl)-2H-pyran-2-one, 5-((3S,5R,8R,9S,10S,13R,14S,17R)-3-((S)-3-aminopyrrolidin-1-yl)-14-hydroxy-10,13-dimethylhexadecahydro-1H-cyclopenta[a]phenanthren-17-yl)-2H-pyran-2-one, 5-((3S,5R,8R,9S,10S,13R,14S,17R)-3-((R)-3-aminopyrrolidin-1-yl)-14-hydroxy-10,13-dimethylhexadecahydro-1H-cyclopenta[a]phenanthren-17-yl)-2H-pyran-2-one, 5-((3S,5R,8R,9S,10S,13R,14S,17R)-14-hydroxy-3-((R)-3-hydroxypyrrolidin-1-yl)-10,13-dimethylhexadecahydro-1H-cyclopenta[a]phenanthren-17-yl)-2H-pyran-2-one, 5-((3S,5R,8R,9S,10S,13R,14S,17R)-3-(1,4-diazepan-1-yl)-14-hydroxy-10,13-dimethylhexadecahydro-1H-cyclopenta[a]phenanthren-17-yl)-2H-pyran-2-one, 5-((3S,5R,8R,9S,10S,13R,14S,17R)-14-hydroxy-10,13-dimethyl-3-(4-methyl-1,4-diazepan-1-yl)hexadecahydro-1H-cyclopenta[a]phenanthren-17-yl)-2H-pyran-2-one, 5-((3S,5R,8R,9S,10S,13R,14S,17R)-14-hydroxy-10,13-dimethyl-3-(piperidin-1-yl)hexadecahydro-1H-cyclopenta[a]phenanthren-17-yl)-2H-pyran-2-one, 5-((3S,5R,8R,9S,10S,13R,14S,17R)-14-hydroxy-3-((R)-2-(hydroxymethyl)piperazin-1-yl)-10,13-dimethylhexadecahydro-1H-cyclopenta[a]phenanthren-17-yl)-2H-pyran-2-one, 5-((3S,5R,8R,9S,10S,13R,14S,17R)-14-hydroxy-3-((S)-2-(hydroxymethyl)piperazin-1-yl)-10,13-dimethylhexadecahydro-1H-cyclopenta[a]phenanthren-17-yl)-2H-pyran-2-one, 5-((3S,5R,8R,9S,10S,13R,14S,17R)-14-hydroxy-3-(2-(hydroxymethyl)piperazin-1-yl)-10,13-dimethylhexadecahydro-1H-cyclopenta[a]phenanthren-17-yl)-2H-pyran-2-one, 5-((3S,5R,8R,9S,10S,13R,14S,17R)-14-hydroxy-3-((S)-3-(hydroxymethyl)piperazin-1-yl)-10,13-dimethylhexadecahydro-1H-cyclopenta[a]phenanthren-17-yl)-2H-pyran-2-one, 5-((3S,5R,8R,9S,10S,13R,14S,17R)-14-hydroxy-3-((R)-3-(hydroxymethyl)piperazin-1-yl)-10,13-dimethylhexadecahydro-1H-cyclopenta[a]phenanthren-17-yl)-2H-pyran-2-one, 5-((3S,5R,8R,9S,10S,13R,14S,17R)-14-hydroxy-3-(3-(hydroxymethyl)piperazin-1-yl)-10,13-dimethylhexadecahydro-1H-cyclopenta[a]phenanthren-17-yl)-2H-pyran-2-one, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)piperazin-2-one, 5-((3S,5R,8R,9S,10S,13R,14S,17R)-14-hydroxy-3-(1H-imidazol-1-yl)-10,13-dimethylhexa decahydro-1H-cyclopenta[a]phenanthren-17-yl)-2H-pyran-2-one, 5-((3S,5R,8R,9S,10S,13R,14S,17R)-14-hydroxy-10,13-dimethyl-3-(1H-pyrazol-1-yl)hexadecahydro-1H-cyclopenta[a]phenanthren-17-yl)-2H-pyran-2-one, 5-((3S,5R,8R,9S,10S,13R,14S,17R)-14-hydroxy-3-(4-(2-hydroxypropan-2-yl)-1H-imidazol-1-yl)-10,13-dimethyl-hexadecahydro-1H-cyclopenta[a]phenanthren-17-yl)-2H-pyran-2-one, 5-((3S,5R,8R,9S,10S,13R,14S,17R)-14-hydroxy-10,13-dimethyl-3-(4-methyl-1H-imidazol-1-yl)hexadecahydro-1H-cyclopenta[a]phenanthren-17-yl)-2H-pyran-2-one, 5-((3S,5R,8R,9S,10S,13R,14S,17R)-14-hydroxy-10,13-dimethyl-3-(2-methyl-1H-imidazol-1-yl)hexadecahydro-1H-cyclopenta[a]phenanthren-17-yl)-2H-pyran-2-one, 3-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)pyrimidin-4(3H)-one, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)pyrazin-2(1H)-one, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)pyridin-2(1H)-one, 2-hydroxy-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)ethanesulfonamide, 2-amino-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)ethanesulfonamide, N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)methylaminosulfonamide, 2-aminoethyl ((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)(methyl)carbamate, 2-hydroxyethyl ((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)(methyl)carbamate, 2-(2-oxopyrrolidin-1-yl)ethyl ((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)carbamate, 2-(2-oxopyrrolidin-1-yl)ethyl ((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)(methyl)carbamate, 2-(pyrrolidin-1-yl)ethyl ((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)(methyl)carbamate, 2-((R)-3-hydroxypyrrolidin-1-yl)ethyl ((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)(methyl)carbamate, 2-morpholinoethyl ((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)(methyl)carbamate, 2-(3-oxopiperazin-1-yl)ethyl ((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)(methyl)carbamate, 2-(piperazin-1-yl)ethyl ((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)carbamate, 2-(piperazin-1-yl)ethyl ((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)(methyl)carbamate, 2-(4-methylpiperazin-1-yl)ethyl ((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)carbamate, 2-(4-methylpiperazin-1-yl)ethyl ((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)(methyl)carbamate, 3-(2-aminoethyl)-1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-1-methylurea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-(2-hydroxyethyl)-1-methylurea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-(2-hydroxyethyl)imidazolidin-2-one, 1-(2-aminoethyl)-3-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)imidazolidin-2-one, 1-(2-aminoethyl)-3-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-1H-imidazol-2(3H)-one, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-(2-hydroxyethyl)-1H-imidazol-2(3H)-one, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-1-methyl-3-(2-(pyrrolidin-1-yl)ethyl)urea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-(2-(2-oxopyrrolidin-1-yl)ethyl)urea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-1-methyl-3-(2-(2-oxopyrrolidin-1-yl)ethyl)urea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-1-methyl-3-(2-morpholinoethyl)urea, N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N,4-dimethylpiperazine-1-carboxamide, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-1-methyl-3-(2-(4-methylpiperazin-1-yl)ethyl)urea, N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N-(2-hydroxyethyl)morpholine-4-carboxamide, N-(2-aminoethyl)-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)morpholine-4-carboxamide, 4-(3-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-methylureido)butanoic acid, N-((5R,8R,9S,10S,13R,14S,17R)-14-hydroxy-10,13-dimethyl-17-(2-oxo-214-pyran-5-yl)hexadecahydro-1H-cyclopenta[a]phenanthren-3-yl)-N-methylpiperazine-1-carboxamide, N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N-methylpiperazine-1-carboxamide, N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N-(2-hydroxyethyl)piperazine-1-carboxamide, N-(2-aminoethyl)-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)piperazine-1-carboxamide, 1-((3R)-3-fluoropiperidin-4-yl)-3-((3S,5R,8R,9S,10S,13R,14S,17R)-14-hydroxy-10,13-dimethyl-17-(2-oxo-2H-pyran-5-yl)hexa decahydro-1H-cyclopenta[a]phenanthren-3-yl)urea, 1-((3 S)-3-fluoropiperidin-4-yl)-3-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)urea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-((3R)-3-hydroxypiperidin-4-yl)urea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-((3S)-3-hydroxypiperidin-4-yl)urea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-((3R)-3-(hydroxymethyl)piperidin-4-yl)urea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-((3S)-3-(hydroxymethyl)piperidin-4-yl)urea, 1-((3R)-3-(aminomethyl)piperidin-4-yl)-3-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)urea, 1-((3 S)-3-(aminomethyl)piperidin-4-yl)-3-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)urea, 3-((3R)-3-fluoropiperidin-4-yl)-1-43S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-1-methylurea, 3-((3 S)-3-fluoropiperidin-4-yl)-1-((3S,5R,8R,9S,10S,13R,14S,17R)-14-hydroxy-10,13-dimethyl-17-(2-oxo-2H-pyran-5-yl)hexa decahydro-1H-cyclopenta[a]phenanthren-3-yl)-1-methylurea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-((3R)-3-hydroxypiperidin-4-yl)-1-methylurea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-((3S)-3-hydroxypiperidin-4-yl)-1-methylurea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-((2S)-2-(hydroxymethyl)piperidin-4-yl)urea, 1-((2 S)-2-(aminomethyl)piperidin-4-yl)-3-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)urea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-((2R)-2-(hydroxymethyl)piperidin-4-yl)urea, 1-((2R)-2-(aminomethyl)piperidin-4-yl)-3-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)urea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-1-methyl-3-(piperidin-4-yl)urea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-1-(2-hydroxyethyl)-3-(piperidin-4-yl)urea, 1-(2-aminoethyl)-1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-(piperidin-4-yl)urea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-1-methyl-3-((S)-piperidin-3-yl)urea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-((S)-piperidin-3-yl)urea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-1-(2-hydroxyethyl)-34 S)-piperidin-3-yl)urea, 1-(2-aminoethyl)-1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-((S)-piperidin-3-yl)urea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-1-methyl-3-((R)-piperidin-3-yl)urea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-((R)-piperidin-3-yl)urea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-1-(2-hydroxyethyl)-3-((R)-piperidin-3-yl)urea, 1-(2-aminoethyl)-1-((3S,5R,8R,9S,10S,13R,14S,17R)-14-hydroxy-10,13-dimethyl-17-(2-oxo-2H-pyran-5-yl)hexa decahydro-1H-cyclopenta[a]phenanthren-3-yl)-3-((R)-piperidin-3-yl)urea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-1-methyl-3-(piperidin-4-ylmethyl)urea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-1-methyl-3-((R)-piperidin-2-ylmethyl)urea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-1-methyl-3-((S)-piperidin-2-ylmethyl)urea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-((5-hydroxypiperidin-2-yl)methyl)-1-methylurea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-((5-hydroxypiperidin-2-yl)methyl)urea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-((6-(hydroxymethyl)piperidin-2-yl)methyl)urea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-((6-(hydroxymethyl)piperidin-2-yl)methyl)-1-methylurea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-1-methyl-3-((S)-piperidin-3-ylmethyl)urea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-1-methyl-3-((R)-piperidin-3-ylmethyl)urea, (R)—N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-(hydroxymethyl)-N-methylpiperazine-1-carboxamide, (S)—N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-(hydroxymethyl)-N-methylpiperazine-1-carboxamide, (S)—N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-2-(hydroxymethyl)-N-methylpiperazine-1-carboxamide, (R)—N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-2-(hydroxymethyl)-N-methylpiperazine-1-carboxamide, N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N-methyl-1,4-diazepane-1-carboxamide, N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N-(2-hydroxyethyl)-1,4-diazepane-1-carboxamide, N-(2-aminoethyl)-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-1,4-diazepane-1-carboxamide, N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N,4-dimethyl-1,4-diazepane-1-carboxamide, N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N-(2-hydroxyethyl)-4-methyl-1,4-diazepane-1-carboxamide, N-(2-aminoethyl)-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-4-methyl-1,4-diazepane-1-carboxamide, N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N-methyl-3-oxopiperazine-1-carboxamide, (S)-3-hydroxy-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N-methylpyrrolidine-1-carboxamide, (R)-3-hydroxy-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N-methylpyrrolidine-1-carboxamide, (S)-3-amino-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N-methylpyrrolidine-1-carboxamide, (R)-3-amino-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N-methylpyrrolidine-1-carboxamide, (R)-3-amino-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)pyrrolidine-1-carboxamide, (S)-3-amino-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)pyrrolidine-1-carboxamide, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-1-methyl-3-(2-(2-oxopiperazin-1-yl)ethyl)urea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-1-methyl-3-(2-(4-methyl-2-oxopiperazin-1-yl)ethyl)urea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-1-methyl-3-(2-(3-oxopiperazin-1-yl)ethyl)urea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-(2-((S)-3-hydroxypyrrolidin-1-yl)ethyl)-1-methylurea, 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-(2-((R)-3-hydroxypyrrolidin-1-yl)ethyl)-1-methylurea, 2-amino-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N-methylacetamide, N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N-methyl-2-(pyrrolidin-1-yl)acetamide, N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N-methyl-2-morpholinoacetamide, N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N-(2-hydroxyethyl)-2-morpholinoacetamide, N-(2-aminoethyl)-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-2-morpholinoacetamide, (R)-2-amino-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N-methylpropanamide, (S)-2-amino-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N-methylpropanamide, (S)-2-amino-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N-(2-hydroxyethyl)propanamide, (S)-2-amino-N-(2-aminoethyl)-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)propanamide, (R)-2-amino-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N-(2-hydroxyethyl)-3-methylbutanamide,
(S)-2-amino-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N-(2-hydroxyethyl)-3-methylbutanamide,
(S)-2-amino-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N,3-dimethylbutanamide,
(R)-2-amino-N1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N1-methylsuccinamide,
(S)-2-amino-N1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N1-methylsuccinamide,
(R)—N-((3S,5R,8R,9S,10S,13R,14S,17R)-14-hydroxy-10,13-dimethyl-17-(2-oxo-214-pyran-5-yl)hexadecahydro-1H-cyclopenta[a]phenanthren-3-yl)-N-methylpyrrolidine-2-carboxamide,
(S)—N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N-methylpyrrolidine-2-carboxamide,
(S)—N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N-methylpyrrolidine-3-carboxamide,
(R)—N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N-methylpyrrolidine-3-carboxamide,
(3S,5R,8R,9S,10S,13R,14S,16S,17R)-14-hydroxy-10,13-dimethyl-3-(methylsulfonamido)-17-(2-oxo-2H-pyran-5-yl)hexadecahydro-1H-cyclopenta[a]phenanthren-16-yl acetate,
(3S,5R,8R,9S,10S,13R,14S,16S,17R)-14-hydroxy-10,13-dimethyl-17-(2-oxo-2H-pyran-5-yl)-3-(2-(pyrrolidin-1-yl)acetamido)hexadecahydro-1H-cyclopenta[a]phenanthren-16-yl acetate,
(3S,5R,8R,9S,10S,13R,14S,16S,17R)-14-hydroxy-10,13-dimethyl-3-(1-methylpyrrolidine-2-carboxamido)-17-(2-oxo-2H-pyran-5-yl)hexadecahydro-1H-cyclopenta[a]phenanthren-16-yl acetate,
(3S,5R,8R,9S,10S,13R,14S,16S,17R)-14-hydroxy-3-((methoxycarbonyl)amino)-10,13-dimethyl-17-(2-oxo-2H-pyran-5-yl)hexadecahydro-1H-cyclopenta[a]phenanthren-16-yl acetate,
(3S,5R,8R,9S,10S,13R,14S,16S,17R)-14-hydroxy-3-((methoxycarbonyl)(methyl)amino)-10,13-dimethyl-17-(2-oxo-2H-pyran-5-yl)hexadecahydro-1H-cyclopenta[a]phenanthren-16-yl acetate,
(3S,5R,8R,9S,10S,13R,14S,16S,17R)-14-hydroxy-10,13-dimethyl-3-(methyl((2-(pyrrolidin-1-yl)ethoxy)carbonyl)amino)-17-(2-oxo-2H-pyran-5-yl)hexadecahydro-1H-cyclopenta[a]phenanthren-16-yl acetate,
(3S,5R,8R,9S,10S,13R,14S,16S,17R)-14-hydroxy-10,13-dimethyl-3-(methyl((2-morpholinoethoxy)carbonyl)amino)-17-(2-oxo-2H-pyran-5-yl)hexadecahydro-1H-cyclopenta[a]phenanthren-16-yl acetate,
(3S,5R,8R,9S,10S,13R,14S,16S,17R)-14-hydroxy-10,13-dimethyl-3-(1-methyl-3-(2-(pyrrolidin-1-yl)ethyl)ureido)-17-(2-oxo-2H-pyran-5-yl)hexa decahydro-1H-cyclopenta[a]phenanthren-16-yl acetate,
(3S,5R,8R,9S,10S,13R,14S,16S,17R)-14-hydroxy-10,13-dimethyl-3-(N-methylpiperazine-1-carboxamido)-17-(2-oxo-2H-pyran-5-yl)hexadecahydro-1H-cyclopenta[a]phenanthren-16-yl acetate,
(3S,5R,8R,9S,10S,13R,14S,16S,17R)-3-(N,4-dimethylpiperazine-1-carboxamido)-14-hydroxy-10,13-dimethyl-17-(2-oxo-2H-pyran-5-yl)hexadecahydro-1H-cyclopenta[a]phenanthren-16-yl acetate,
(3S,5R,8R,9S,10S,13R,14S,16S,17R)-14-hydroxy-10,13-dimethyl-17-(2-oxo-2H-pyran-5-yl)-3-(3-(piperidin-4-yl)ureido)hexadecahydro-1H-cyclopenta[a]phenanthren-16-yl acetate,
(3S,5R,8R,9S,10S,13R,14S,16S,17R)-14-hydroxy-10,13-dimethyl-3-(N-methyl-1,4-diazepane-1-carboxamido)-17-(2-oxo-2H-pyran-5-yl)hexadecahydro-1H-cyclopenta[a]phenanthren-16-yl acetate,
(3S,5R,8R,9S,10S,13R,14S,16S,17R)-3-(N,4-dimethyl-1,4-diazepane-1-carboxamido)-14-hydroxy-10,13-dimethyl-17-(2-oxo-2H-pyran-5-yl)hexadecahydro-1H-cyclopenta[a]phenanthren-16-yl acetate,
(3S,5R,8R,9S,10S,13R,14S,16S,17R)-14-hydroxy-10,13-dimethyl-17-(2-oxo-2H-pyran-5-yl)-3-(piperidin-1-yl)hexa decahydro-1H-cyclopenta[a]phenanthren-16-yl acetate,
(3S,5R,8R,9S,10S,13R,14S,16S,17R)-14-hydroxy-10,13-dimethyl-17-(2-oxo-2H-pyran-5-yl)-3-(piperazin-1-yl)hexadecahydro-1H-cyclopenta[a]phenanthren-16-yl acetate,
(3S,5R,8R,9S,10S,13R,14S,16S,17R)-14-hydroxy-10,13-dimethyl-3-(4-methylpiperazin-1-yl)-17-(2-oxo-2H-pyran-5-yl)hexadecahydro-1H-cyclopenta[a]phenanthren-16-yl acetate,
(3S,5R,8R,9S,10S,13R,14S,16S,17R)-14-hydroxy-10,13-dimethyl-3-morpholino-17-(2-oxo-2H-pyran-5-yl)hexadecahydro-1H-cyclopenta[a]phenanthren-16-yl acetate,
(5R,8R,9S,10S,13R,14S,16S,17R)-14-hydroxy-10,13-dimethyl-17-(2-oxo-2H-pyran-5-yl)-3-(piperazin-1-yl)hexadecahydro-1H-cyclopenta[a]phenanthren-16-yl acetate,
(5R,8R,9S,10S,13R,14S,16S,17R)-14-hydroxy-10,13-dimethyl-17-(2-oxo-2H-pyran-5-yl)-3-(pyrrolidin-1-yl)hexadecahydro-1H-cyclopenta[a]phenanthren-16-yl acetate,
5-((3S,5S,8R,9S,10R,13R,14S,17R)-3-amino-5,14-dihydroxy-10,13-dimethylhexadecahydro-1H-cyclopenta[a]phenanthren-17-yl)-2H-pyran-2-one,
5-((3S,5S,8R,9S,10R,13R,14S,17R)-5,14-dihydroxy-10,13-dimethyl-3-(pyrrolidin-1-yl)hexadecahydro-1H-cyclopenta[a]phenanthren-17-yl)-2H-pyran-2-one,
5-((5 S,8R,9S,10R,13R,14S,17R)-5,14-dihydroxy-10,13-dimethyl-3-(piperazin-1-yl)hexadecahydro-1H-cyclopenta[a]phenanthren-17-yl)-2H-pyran-2-one,
5-((3S,5S,8R,9S,10R,13R,14S,17R)-5,14-dihydroxy-10,13-dimethyl-3-(piperazin-1-yl)hexadecahydro-1H-cyclopenta[a]phenanthren-17-yl)-2H-pyran-2-one,
5-((3S,5S,8R,9S,10R,13R,14S,17R)-5,14-dihydroxy-10,13-dimethyl-3-(piperidin-1-yl)hexadecahydro-1H-cyclopenta[a]phenanthren-17-yl)-2H-pyran-2-one,
5-((3S,5S,8R,9S,10R,13R,14S,17R)-5,14-dihydroxy-10,13-dimethyl-3-((2-(pyrrolidin-1-yl)ethyl)amino)hexadecahydro-1H-cyclopenta[a]phenanthren-17-yl)-2H-pyran-2-one,
5-((3S,5S,8R,9S,10R,13R,14S,17R)-5,14-dihydroxy-10,13-dimethyl-3-morpholinohexadecahydro-1H-cyclopenta[a]phenanthren-17-yl)-2H-pyran-2-one,
5-((3S,5S,8R,9S,10R,13R,14S,17R)-5,14-dihydroxy-10,13-dimethyl-3-((2-morpholinoethyl)amino)hexadecahydro-1H-cyclopenta[a]phenanthren-17-yl)-2H-pyran-2-one, 4-((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)piperazin-2-one, 5-((3S,5S,8R,9S,10R,13R,14S,17R)-5,14-dihydroxy-3-(2-hydroxyethyl)(methyl)amino)-10,13-dimethylhexadecahydro-1H-cyclopenta[a]phenanthren-17-yl)-2H-pyran-2-one, 5-((3S,5S,8R,9S,10R,13R,14S,17R)-5,14-dihydroxy-10,13-dimethyl-3-(piperidin-4-ylamino)hexadecahydro-1H-cyclopenta[a]phenanthren-17-yl)-2H-pyran-2-one, methyl ((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)(methyl)carbamate, 2-aminoethyl ((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)(methyl)carbamate, 2-(pyrrolidin-1-yl)ethyl ((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)(methyl)carbamate, N-((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)methanesulfonamide, 2-amino-N-((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)acetamide, N-((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)-2-(pyrrolidin-1-yl)acetamide, N-((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)-2-morpholinoacetamide, (R)-2-amino-N-((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)propanamide, (S)-2-amino-N-((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)propanamide, (S)-2-amino-N-((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)-3-methylbutanamide, (R)-2-amino-N1-((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)succinamide, (S)-2-amino-N1-((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)succinamide, (S)—N-((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)pyrrolidine-2-carboxamide, N-((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)-N-methylpiperazine-1-carboxamide, 5-((3S,5S,8R,9S,10R,13R,14S,17R)-5,14-dihydroxy-10,13-dimethyl-3-((1-methylpiperidin-4-yl)amino)hexadecahydro-1H-cyclopenta[a]phenanthren-17-yl)-2H-pyran-2-one, 5-((3S,5S,8R,9S,10R,13R,14S,17R)-3-(((3R)-3-fluoropiperidin-4-yl)amino)-5,14-dihydroxy-10,13-dimethylhexadecahydro-1H-cyclopenta[a]phenanthren-17-yl)-2H-pyran-2-one, 5-((3S,5S,8R,9S,10R,13R,14S,17R)-3-(((3 S)-3-fluoropiperidin-4-yl)amino)-5,14-dihydroxy-10,13-dimethylhexadecahydro-1H-cyclopenta[a]phenanthren-17-yl)-2H-pyran-2-one, 5-((3S,5S,8R,9S,10R,13R,14S,17R)-3-(((3R)-3-fluoropiperidin-4-yl)(methyl)amino)-5,14-dihydroxy-10,13-dimethylhexadecahydro-1H-cyclopenta[a]phenanthren-17-yl)-2H-pyran-2-one, 5-((3S,5S,8R,9S,10R,13R,14S,17R)-3-((3 S)-3-fluoropiperidin-4-yl)(methyl)amino)-5,14-dihydroxy-10,13-dimethylhexadecahydro-1H-cyclopenta[a]phenanthren-17-yl)-2H-pyran-2-one, 5-((3S,5S,8R,9S,10R,13R,14S,17R)-3-(((3R)-3-fluoro-1-methylpiperidin-4-yl)(methyl)amino)-5,14-dihydroxy-10,13-dimethylhexadecahydro-1H-cyclopenta[a]phenanthren-17-yl)-2H-pyran-2-one, 5-((3S,5S,8R,9S,10R,13R,14S,17R)-3-(((3 S)-3-fluoro-1-methylpiperidin-4-yl)(methyl)amino)-5,14-dihydroxy-10,13-dimethylhexadecahydro-1H-cyclopenta[a]phenanthren-17-yl)-2H-pyran-2-one, 5-((3S,5S,8R,9S,10R,13R,14S,17R)-3-(((3R)-3-fluoro-1-methylpiperidin-4-yl)amino)-5,14-dihydroxy-10,13-dimethylhexadecahydro-1H-cyclopenta[a]phenanthren-17-yl)-2H-pyran-2-one, 5-((3S,5S,8R,9S,10R,13R,14S,17R)-3-(((3 S)-3-fluoro-1-methylpiperidin-4-yl)amino)-5,14-dihydroxy-10,13-dimethylhexadecahydro-1H-cyclopenta[a]phenanthren-17-yl)-2H-pyran-2-one, 5-((3S,5S,8R,9S,10R,13R,14S,17R)-5,14-dihydroxy-10,13-dimethyl-3-(methyl(piperidin-4-yl)amino)hexadecahydro-1H-cyclopenta[a]phenanthren-17-yl)-2H-pyran-2-one, 5-((3S,5S,8R,9S,10R,13R,14S,17R)-3-((S)-3-(aminomethyl)morpholino)-5,14-dihydroxy-10,13-dimethylhexadecahydro-1H-cyclopenta[a]phenanthren-17-yl)-2H-pyran-2-one, 5-((3S,5S,8R,9S,10R,13R,14S,17R)-3-((R)-3-(aminomethyl)morpholino)-5,14-dihydroxy-10,13-dimethylhexadecahydro-1H-cyclopenta[a]phenanthren-17-yl)-2H-pyran-2-one, 5-((3S,5S,8R,9S,10R,13R,14S,17R)-5,14-dihydroxy-3-((R)-3-(hydroxymethyl)morpholino)-10,13-dimethylhexadecahydro-1H-cyclopenta[a]phenanthren-17-yl)-2H-pyran-2-one, 5-((3S,5S,8R,9S,10R,13R,14S,17R)-5,14-dihydroxy-3-((S)-3-(hydroxymethyl)morpholino)-10,13-dimethylhexadecahydro-1H-cyclopenta[a]phenanthren-17-yl)-2H-pyran-2-one, 5-((3S,5S,8R,9S,10R,13R,14S,17R)-5,14-dihydroxy-3-((R)-2-(hydroxymethyl)morpholino)-10,13-dimethylhexadecahydro-1H-cyclopenta[a]phenanthren-17-yl)-2H-pyran-2-one, 5-((3S,5S,8R,9S,10R,13R,14S,17R)-3-((S)-2-(aminomethyl)morpholino)-5,14-dihydroxy-10,13-dimethylhexadecahydro-1H-cyclopenta[a]phenanthren-17-yl)-2H-pyran-2-one, 5-((3S,5S,8R,9S,10R,13R,14S,17R)-3-(R)-2-(aminomethyl)morpholino)-5,14-dihydroxy-10,13-dimethylhexadecahydro-1H-cyclopenta[a]phenanthren-17-yl)-2H-pyran-2-one,
5-((3S,5S,8R,9S,10R,13R,14S,17R)-5,14-dihydroxy-3-((S)-2-(hydroxymethyl)morpholino)-10,13-dimethyl-hexadecahydro-1H-cyclopenta[a]phenanthren-17-yl)-2H-pyran-2-one,
5-((3S,5S,8R,9S,10R,13R,14S,17R)-5,14-dihydroxy-3-((S)-2-(hydroxymethyl)pyrrolidin-1-yl)-10,13-dimethyl-hexadecahydro-1H-cyclopenta[a]phenanthren-17-yl)-2H-pyran-2-one,
5-((3S,5S,8R,9S,10R,13R,14S,17R)-5,14-dihydroxy-3-((R)-2-(hydroxymethyl)pyrrolidin-1-yl)-10,13-dimethyl-hexadecahydro-1H-cyclopenta[a]phenanthren-17-yl)-2H-pyran-2-one,
5-((3S,5S,8R,9S,10R,13R,14S,17R)-3-((S)-2-(aminomethyl)pyrrolidin-1-yl)-5,14-dihydroxy-10,13-dimethyl-hexadecahydro-1H-cyclopenta[a]phenanthren-17-yl)-2H-pyran-2-one,
5-((3S,5S,8R,9S,10R,13R,14S,17R)-3-((R)-2-(aminomethyl)pyrrolidin-1-yl)-5,14-dihydroxy-10,13-dimethyl-hexadecahydro-1H-cyclopenta[a]phenanthren-17-yl)-2H-pyran-2-one,
5-((3S,5S,8R,9S,10R,13R,14S,17R)-5,14-dihydroxy-3-((S)-3-hydroxypyrrolidin-1-yl)-10,13-dimethylhexadecahydro-1H-cyclopenta[a]phenanthren-17-yl)-2H-pyran-2-one,
5-((3S,5S,8R,9S,10R,13R,14S,17R)-3-((S)-3-aminopyrrolidin-1-yl)-5,14-dihydroxy-10,13-dimethylhexadecahydro-1H-cyclopenta[a]phenanthren-17-yl)-2H-pyran-2-one,
5-((3S,5S,8R,9S,10R,13R,14S,17R)-3-((R)-3-aminopyrrolidin-1-yl)-5,14-dihydroxy-10,13-dimethylhexadecahydro-1H-cyclopenta[a]phenanthren-17-yl)-2H-pyran-2-one,
5-((3S,5S,8R,9S,10R,13R,14S,17R)-5,14-dihydroxy-3-((R)-3-hydroxypyrrolidin-1-yl)-10,13-dimethylhexadecahydro-1H-cyclopenta[a]phenanthren-17-yl)-2H-pyran-2-one,
5-((3S,5S,8R,9S,10R,13R,14S,17R)-3-(1,4-diazepan-1-yl)-5,14-dihydroxy-10,13-dimethylhexadecahydro-1H-cyclopenta[a]phenanthren-17-yl)-2H-pyran-2-one,
5-((3S,5S,8R,9S,10R,13R,14S,17R)-5,14-dihydroxy-10,13-dimethyl-3-(4-methyl-1,4-diazepan-1-yl)hexadecahydro-1H-cyclopenta[a]phenanthren-17-yl)-2H-pyran-2-one,
5-((3S,5S,8R,9S,10R,13R,14S,17R)-5,14-dihydroxy-3-((R)-2-(hydroxymethyl)piperazin-1-yl)-10,13-dimethyl-hexadecahydro-1H-cyclopenta[a]phenanthren-17-yl)-2H-pyran-2-one,
5-((3S,5S,8R,9S,10R,13R,14S,17R)-5,14-dihydroxy-3-((S)-2-(hydroxymethyl)piperazin-1-yl)-10,13-dimethyl-hexadecahydro-1H-cyclopenta[a]phenanthren-17-yl)-2H-pyran-2-one,
5-((3S,5S,8R,9S,10R,13R,14S,17R)-5,14-dihydroxy-3-(2-(hydroxymethyl)piperazin-1-yl)-10,13-dimethylhexadecahydro-1H-cyclopenta[a]phenanthren-17-yl)-2H-pyran-2-one,
5-((3S,5S,8R,9S,10R,13R,14S,17R)-5,14-dihydroxy-3-((S)-3-(hydroxymethyl)piperazin-1-yl)-10,13-dimethyl-hexadecahydro-1H-cyclopenta[a]phenanthren-17-yl)-2H-pyran-2-one,
5-((3S,5S,8R,9S,10R,13R,14S,17R)-5,14-dihydroxy-3-((R)-3-(hydroxymethyl)piperazin-1-yl)-10,13-dimethyl-hexadecahydro-1H-cyclopenta[a]phenanthren-17-yl)-2H-pyran-2-one,
5-((3S,5S,8R,9S,10R,13R,14S,17R)-5,14-dihydroxy-3-(3-(hydroxymethyl)piperazin-1-yl)-10,13-dimethylhexadecahydro-1H-cyclopenta[a]phenanthren-17-yl)-2H-pyran-2-one,
1-((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)piperazin-2-one,
5-((3S,5S,8R,9S,10R,13R,14S,17R)-5,14-dihydroxy-3-(1H-imidazol-1-yl)-10,13-dimethylhexadecahydro-1H-cyclopenta[a]phenanthren-17-yl)-2H-pyran-2-one,
5-((3S,5S,8R,9S,10R,13R,14S,17R)-5,14-dihydroxy-3-(4-(2-hydroxypropan-2-yl)-1H-imidazol-1-yl)-10,13-dimethylhexadecahydro-1H-cyclopenta[a]phenanthren-17-yl)-2H-pyran-2-one,
5-((3S,5S,8R,9S,10R,13R,14S,17R)-5,14-dihydroxy-10,13-dimethyl-3-(4-methyl-1H-imidazol-1-yl)hexadecahydro-1H-cyclopenta[a]phenanthren-17-yl)-2H-pyran-2-one,
5-((3S,5S,8R,9S,10R,13R,14S,17R)-5,14-dihydroxy-10,13-dimethyl-3-(2-methyl-1H-imidazol-1-yl)hexadecahydro-1H-cyclopenta[a]phenanthren-17-yl)-2H-pyran-2-one,
3-((3S,5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)pyrimidin-4(3H)-one,
2-(pyrrolidin-1-yl)ethyl ((3S,8R,9S,10R,13R,14S,17R)-14-hydroxy-10,13-dimethyl-17-(2-oxo-2H-pyran-5-yl)-2,3,6,7,8,9,10,11,12,13,14,15,16,17-tetradecahydro-1H-cyclopenta[a]phenanthr en-3-yl)(methyl)carbamate,
2-morpholinoethyl ((3S,8R,9S,10R,13R,14S,17R)-14-hydroxy-10,13-dimethyl-17-(2-oxo-2H-pyran-5-yl)-2,3,6,7,8,9,10,11,12,13,14,15,16,17-tetradecahydro-1H-cyclopenta[a]phenanthr en-3-yl)(methyl)carbamate,
N-((3S,8R,9S,10R,13R,14S,17R)-14-hydroxy-10,13-dimethyl-17-(2-oxo-2H-pyran-5-yl)-2,3,6,7,8,9,10,11,12,13,14,15,16,17-tetradecahydro-1H-cyclopenta[a]phenanthren-3-yl)methanesulfonamide,
N-((3S,8R,9S,10R,13R,14S,17R)-14-hydroxy-10,13-dimethyl-17-(2-oxo-2H-pyran-5-yl)-2,3,6,7,8,9,10,11,12,13,14,15,16,17-tetradecahydro-1H-cyclopenta[a]phenanthren-3-yl)-2-(pyrrolidin-1-yl)acetamide,
N-((3S,8R,9S,10R,13R,14S,17R)-14-hydroxy-10,13-dimethyl-17-(2-oxo-2H-pyran-5-yl)-2,3,6,7,8,9,10,11,12,13,14,15,16,17-tetradecahydro-1H-cyclopenta[a]phenanthren-3-yl)-1-methylpyrrolidine-2-carboxamide,
methyl ((3S,8R,9S,10R,13R,14S,17R)-14-hydroxy-10,13-dimethyl-17-(2-oxo-2H-pyran-5-yl)-2,3,6,7,8,9,10,11,12,13,14,15,16,17-tetradecahydro-1H-cyclopenta[a]phenanthren-3-yl)carbamate,
methyl ((3S,8R,9S,10R,13R,14S,17R)-14-hydroxy-10,13-dimethyl-17-(2-oxo-2H-pyran-5-yl)-2,3,6,7,8,9,10,11,12,13,14,15,16,17-tetradecahydro-1H-cyclopenta[a]phenanthren-3-yl)(methyl)carbamate,
1-((3S,8R,9S,10R,13R,14S,17R)-14-hydroxy-10,13-dimethyl-17-(2-oxo-2H-pyran-5-yl)-2,3,6,7,8,9,10,11,12,13,14,15,16,17-tetradecahydro-1H-cyclopenta[a]phenanthren-3-yl)-1-methyl-3-(2-(pyrrolidin-1-yl)ethyl)urea,
N-((3S,8R,9S,10R,13R,14S,17R)-14-hydroxy-10,13-dimethyl-17-(2-oxo-2H-pyran-5-yl)-2,3,6,7,8,9,10,11,12,13,14,15,16,17-tetradecahydro-1H-cyclopenta[a]phenanthren-3-yl)-N-methylpiperazine-1-carboxamide,
N-((3S,8R,9S,10R,13R,14S,17R)-14-hydroxy-10,13-dimethyl-17-(2-oxo-2H-pyran-5-yl)-2,3,6,7,8,9,10,11,12,13,14,15,16,17-tetradecahydro-1H-cyclopenta[a]phenanthren-3-yl)-N,4-dimethylpiperazine-1-carboxamide,
1-((3S,8R,9S,10R,13R,14S,17R)-14-hydroxy-10,13-dimethyl-17-(2-oxo-2H-pyran-5-yl)-2,3,6,7,8,9,10,11,12,13,14,15,16,17-tetradecahydro-1H-cyclopenta[a]phenanthren-3-yl)-3-(piperidin-4-yl)urea, N-((3S,8R,9S,10R,13R,14S,17R)-14-hydroxy-10,13-dimethyl-17-(2-oxo-2H-pyran-5-yl)-2,3,6,7,8,9,10,11,12,13,14,15,16,17-tetradecahydro-1H-cyclopenta[a]phenanthren-3-yl)-N-methyl-1,4-diazepane-1-carboxamide, N-((3S,8R,9S,10R,13R,14S,17R)-14-hydroxy-10,13-dimethyl-17-(2-oxo-2H-pyran-5-yl)-2,3,6,7,8,9,10,11,12,13,14,15,16,17-tetradecahydro-1H-cyclopenta[a]phenanthren-3-yl)-N,4-dimethyl-1,4-diazepane-1-carboxamide, 5-((3S,8R,9S,10R,13R,14S,17R)-14-hydroxy-10,13-dimethyl-3-(piperidin-1-yl)-2,3,6,7,8,9,10,11,12,13,14,15,16,17-tetradecahydro-1H-cyclopenta[a]phenanthren-17-yl)-2H-pyran-2-one, 5-((3S,8R,9S,10R,13R,14S,17R)-14-hydroxy-10,13-dimethyl-3-(piperazin-1-yl)-2,3,6,7,8,9,10,11,12,13,14,15,16,17-tetradecahydro-1H-cyclopenta[a]phenanthren-17-yl)-2H-pyran-2-one, 5-((3S,8R,9S,10R,13R,14S,17R)-14-hydroxy-10,13-dimethyl-3-(4-methylpiperazin-1-yl)-2,3,6,7,8,9,10,11,12,13,14,15,16,17-tetradecahydro-1H-cyclopenta[a]phenanthren-17-yl)-2H-pyran-2-one, 5-((8R,9S,10R,13R,14S,17R)-14-hydroxy-10,13-dimethyl-3-morpholino-2,3,6,7,8,9,10,11,12,13,14,15,16,17-tetradecahydro-1H-cyclopenta[a]phenanthren-17-yl)-2H-pyran-2-one, 5-((3S,8R,9S,10R,13R,14S,17R)-14-hydroxy-10,13-dimethyl-3-morpholino-2,3,6,7,8,9,10,11,12,13,14,15,16,17-tetradecahydro-1H-cyclopenta[a]phenanthren-17-yl)-2H-pyran-2-one, 5-((8R,9S,10R,13R,14S,17R)-14-hydroxy-10,13-dimethyl-3-(piperazin-1-yl)-2,3,6,7,8,9,10,11,12,13,14,15,16,17-tetradecahydro-1H-cyclopenta[a]phenanthren-17-yl)-2H-pyran-2-one, 5-((8R,9S,10R,13R,14S,17R)-14-hydroxy-10,13-dimethyl-3-(pyrrolidin-1-yl)-2,3,6,7,8,9,10,11,12,13,14,15,16,17-tetradecahydro-1H-cyclopenta[a]phenanthren-17-yl)-2H-pyran-2-one, N-((1R,2aR,3aS,3bR,5aR,7S,9aS,9bS,11aR)-9a,11a-dimethyl-1-(2-oxo-2H-pyran-5-yl)hexadecahydronaphtho[1',2':6,7]indeno[1,7a-b]oxiren-7-yl)methanesulfonamide, N-((1R,2aR,3aS,3bR,5aR,7S,9aS,9bS,11aR)-9a,11a-dimethyl-1-(2-oxo-2H-pyran-5-yl)hexadecahydronaphtho[1',2':6,7]indeno[1,7a-b]oxiren-7-yl)-2-(pyrrolidin-1-yl)acetamide, N-((1R,2aR,3aS,3bR,5aR,7S,9aS,9bS,11aR)-9a,11a-dimethyl-1-(2-oxo-2H-pyran-5-yl)hexadecahydronaphtho[1',2':6,7]indeno[1,7a-b]oxiren-7-yl)-1-methylpyrrolidine-2-carboxamide, methyl ((1R,2aR,3aS,3bR,5aR,7S,9aS,9bS,11aR)-9a,11a-dimethyl-1-(2-oxo-2H-pyran-5-yl)hexadecahydronaphtho[1',2':6,7]indeno[1,7a-b]oxiren-7-yl)carbamate, methyl ((1R,2aR,3aS,3bR,5aR,7S,9aS,9bS,11aR)-9a,11a-dimethyl-1-(2-oxo-2H-pyran-5-yl)hexadecahydronaphtho[1',2':6,7]indeno[1,7a-b]oxiren-7-yl)(methyl)carbamate, 2-(pyrrolidin-1-yl)ethyl ((1R,2aR,3aS,3bR,5aR,7S,9aS,9bS,11aR)-9a,11a-dimethyl-1-(2-oxo-2H-pyran-5-yl)hexadecahydronaphtho[1',2':6,7]indeno[1,7a-b]oxiren-7-yl)(methyl)carbamate, 2-morpholinoethyl ((1R,2aR,3aS,3bR,5aR,7S,9aS,9bS,11aR)-9a,11a-dimethyl-1-(2-oxo-2H-pyran-5-yl)hexadecahydronaphtho[1',2':6,7]indeno[1,7a-b]oxiren-7-yl)(methyl)carbamate, 1-((1R,2aR,3aS,3bR,5aR,7S,9aS,9bS,11aR)-9a,11a-dimethyl-1-(2-oxo-2H-pyran-5-yl)hexadecahydronaphtho[1',2':6,7]indeno[1,7a-b]oxiren-7-yl)-1-methyl-3-(2-(pyrrolidin-1-yl)ethyl)urea, N-((1R,2aR,3aS,3bR,5aR,7S,9aS,9bS,11aR)-9a,11a-dimethyl-1-(2-oxo-2H-pyran-5-yl)hexadecahydronaphtho[1',2':6,7]indeno[1,7a-b]oxiren-7-yl)-N-methylpiperazine-1-carboxamide, (1R,2R,2aR,3aS,3bR,5aR,7S,9aS,9bS,11aR)-7-(N,4-dimethylpiperazine-1-carboxamido)-9a,11a-dimethyl-1-(2-oxo-2H-pyran-5-yl)hexadecahydronaphtho[1',2':6,7]indeno[1,7a-b]oxiren-2-yl acetate, (1R,2R,2aR,3aS,3bR,5aR,7S,9aS,9bS,11aR)-9a,11a-dimethyl-1-(2-oxo-2H-pyran-5-yl)-7-(3-(piperidin-4-yl)ureido)hexadecahydronaphtho[1',2':6,7]indeno[1,7a-b]oxiren-2-yl acetate, (1R,2R,2aR,3aS,3bR,5aR,7S,9aS,9bS,11aR)-9a,11a-dimethyl-7-(N-methyl-1,4-diazepane-1-carboxamido)-1-(2-oxo-2H-pyran-5-yl)hexadecahydronaphtho[1',2':6,7]indeno[1,7a-b]oxiren-2-yl acetate, N-((1R,2aR,3aS,3bR,5aR,7S,9aS,9bS,11aR)-9a,11a-dimethyl-1-(2-oxo-2H-pyran-5-yl)hexadecahydronaphtho[1',2':6,7]indeno[1,7a-b]oxiren-7-yl)-N,4-dimethyl-1,4-diazepane-1-carboxamide, 5-((1R,2aR,3aS,3bR,5aR,7S,9aS,9bS,11aR)-9a,11a-dimethyl-7-(piperidin-1-yl)hexadecahydronaphtho[1',2':6,7]indeno[1,7a-b]oxiren-1-yl)-2H-pyran-2-one, 5-((1R,2aR,3aS,3bR,5aR,7S,9aS,9bS,11aR)-9a,11a-dimethyl-7-(piperazin-1-yl)hexadecahydronaphtho[1',2':6,7]indeno[1,7a-b]oxiren-1-yl)-2H-pyran-2-one, 5-((1R,2aR,3aS,3bR,5aR,7S,9aS,9bS,11aR)-9a,11a-dimethyl-7-(4-methylpiperazin-1-yl)hexadecahydronaphtho[1',2':6,7]indeno[1,7a-b]oxiren-1-yl)-2H-pyran-2-one, 5-((1R,2aR,3aS,3bR,5aR,7S,9aS,9bS,11aR)-9a,11a-dimethyl-7-morpholinohexadecahydronaphtho[1',2':6,7]indeno[1,7a-b]oxiren-1-yl)-2H-pyran-2-one, 5-((1R,2aR,3aS,3bR,5aR,9aS,9bS,11aR)-9a,11a-dimethyl-7-(piperazin-1-yl)hexadecahydronaphtho[1',2':6,7]indeno[1,7a-b]oxiren-1-yl)-2H-pyran-2-one, 5-((1R,2aR,3aS,3bR,5aR,9aS,9bS,11aR)-9a,11a-dimethyl-7-(pyrrolidin-1-yl)hexadecahydronaphtho[1',2':6,7]indeno[1,7a-b]oxiren-1-yl)-2H-pyran-2-one, N-((1R,2aR,3aS,3bR,5aR,7S,9aS,9bS,11aR)-9a,11a-dimethyl-1-(2-oxo-2H-pyran-5-yl)hexadecahydronaphtho[1',2':6,7]indeno[1,7a-b]oxiren-7-yl)-N-methylmorpholine-4-carboxamide, 1-((1R,2aR,3aS,3bR,5aR,7S,9aS,9bS,11aR)-9a,11a-dimethyl-1-(2-oxo-2H-pyran-5-yl)hexadecahydronaphtho[1',2':6,7]indeno[1,7a-b]oxiren-7-yl)-1-methyl-3-(2-(3-oxopiperazin-1-yl)ethyl)urea, (1R,2R,2aR,3aS,3bR,5aR,7S,9aS,9bS,11aR)-9a,11a-dimethyl-7-(methylsulfonamido)-1-(2-oxo-2H-pyran-5-yl)hexadecahydronaphtho[1',2':6,7]indeno[1,7a-b]oxiren-2-yl acetate, (1R,2R,2aR,3aS,3bR,5aR,7S,9aS,9bS,11aR)-9a,11a-dimethyl-1-(2-oxo-2H-pyran-5-yl)-7-(2-(pyrrolidin-1-yl)acetamido)hexadecahydronaphtho[1',2':6,7]indeno[1,7a-b]oxiren-2-yl acetate, (1R,2R,2aR,3aS,3bR,5aR,7S,9aS,9bS,11aR)-9a,11a-dimethyl-7-(1-methylpyrrolidine-2-carboxamido)-1-(2-oxo-2H-pyran-5-yl)hexadecahydronaphtho[1',2':6,7]indeno[1,7a-b]oxiren-2-yl acetate, (1R,2R,2aR,3aS,3bR,5aR,7S,9aS,9bS,11aR)-7-((methoxycarbonyl)amino)-9a,11a-dimethyl-1-(2-oxo-2H-pyran-5-yl)hexadecahydronaphtho[1',2':6,7]indeno[1,7a-b]oxiren-2-yl acetate, (1R,2R,2aR,3aS,3bR,5aR,7S,9aS,9bS,11aR)-7-((methoxycarbonyl)(methyl)amino)-9a,11a-dimethyl-1-(2-oxo-2H-pyran-5-yl)hexadecahydronaphtho[1',2':6,7]indeno[1,7a-b]oxiren-2-yl acetate, (1R,2R,2aR,3aS,3bR,5aR,7S,9aS,9bS,11aR)-9a,11a-dimethyl-7-(methyl((2-(pyrrolidin-1-yl)ethoxy)carbonyl)amino)-1-(2-oxo-2H-pyran-5-yl)hexadecahydronaphtho[1',2':6,7]indeno[1,7a-b]oxiren-2-yl acetate, (1R,2R,2aR,3aS,3bR,5aR,7S,9aS,9bS,11aR)-9a,11a-dimethyl-7-(methyl((2-morpholinoethoxy)carbonyl)amino)-1-(2-oxo-2H-pyran-5-yl)hexadecahydronaphtho[1',2':6,7]indeno[1,7a-b]oxiren-2-yl acetate, (1R,2R,2aR,3aS,3bR,5aR,7S,9aS,9bS,11aR)-9a,11a-dimethyl-7-(1-methyl-3-(2-(pyrrolidin-1-yl)ethyl)ureido)-1-(2-oxo-2H-pyran-5-yl)hexadecahydronaphtho[1',2':6,7]indeno[1,7a-b]oxiren-2-yl acetate, (1R,2R,2aR,3aS,3bR,5aR,7S,9aS,9bS,11aR)-9a,11a-dimethyl-7-(N-methylpiperazine-1-carboxamido)-1-(2-oxo-2H-pyran-5-yl)hexadecahydronaphtho[1',2':6,7]indeno[1,7a-b]oxiren-2-yl acetate, (1R,2R,2aR,3aS,3bR,5aR,7S,9aS,9bS,11aR)-7-(N,4-dimethyl-1,4-diazepane-1-carboxamido)-9a,11a-dimethyl-1-(2-oxo-2H-pyran-5-yl)hexa decahydronaphtho[1',2':6,7]indeno[1,7a-b]oxiren-2-yl acetate, (1R,2R,2aR,3aS,3bR,5aR,7S,9aS,9bS,11aR)-9a,11a-dimethyl-1-(2-oxo-2H-pyran-5-yl)-7-(piperidin-1-yl)hexadecahydronaphtho[1',2':6,7]indeno[1,7a-b]oxiren-2-yl acetate, (1R,2R,2aR,3aS,3bR,5aR,7S,9aS,9bS,11aR)-9a,11a-dimethyl-1-(2-oxo-2H-pyran-5-yl)-7-(piperazin-1-yl)hexadecahydronaphtho[1',2':6,7]indeno[1,7a-b]oxiren-2-yl acetate, (1R,2R,2aR,3aS,3bR,5aR,7S,9aS,9bS,11aR)-9a,11a-dimethyl-7-(4-methylpiperazin-1-yl)-1-(2-oxo-2H-pyran-5-yl)hexadecahydronaphtho[1',2':6,7]indeno[1,7a-b]oxiren-2-yl acetate, (1R,2R,2aR,3aS,3bR,5aR,7S,9aS,9bS,11aR)-9a,11a-dimethyl-7-morpholino-1-(2-oxo-2H-pyran-5-yl)hexadecahydronaphtho[1',2':6,7]indeno[1,7a-b]oxiren-2-yl acetate, (1R,2R,2aR,3aS,3bR,5aR,9aS,9bS,11aR)-9a,11a-dimethyl-1-(2-oxo-2H-pyran-5-yl)-7-(piperazin-1-yl)hexadecahydronaphtho[1',2':6,7]indeno[1,7a-b]oxiren-2-yl acetate, (1R,2R,2aR,3aS,3bR,5aR,9aS,9bS,11aR)-9a,11a-dimethyl-1-(2-oxo-2H-pyran-5-yl)-7-(pyrrolidin-1-yl)hexadecahydronaphtho[1',2':6,7]indeno[1,7a-b]oxiren-2-yl acetate, (1R,2R,2aR,3aS,3bR,5aR,7S,9aS,9bS,11aR)-9a,11a-dimethyl-7-(N-methylmorpholine-4-carboxamido)-1-(2-oxo-2H-pyran-5-yl)hexadecahydronaphtho[1',2':6,7]indeno[1,7a-b]oxiren-2-yl acetate, (1R,2R,2aR,3aS,3bR,5aR,7S,9aS,9bS,11aR)-9a,11a-dimethyl-7-(1-methyl-3-(2-(3-oxopiperazin-1-yl)ethyl)ureido)-1-(2-oxo-2H-pyran-5-yl)hexadecahydronaphtho[1',2':6,7]indeno[1,7a-b]oxiren-2-yl acetate, (1R,2R,2aR,3aS,3bR,5aS,7S,9aR,9bS,11aR)-5a-hydroxy-9a,11a-dimethyl-7-(methylsulfonamido)-1-(2-oxo-2H-pyran-5-yl)hexadecahydronaphtho[1',2':6,7]indeno[1,7a-b]oxiren-2-yl acetate, (1R,2R,2aR,3aS,3bR,5aS,7S,9aR,9bS,11aR)-5a-hydroxy-9a,11a-dimethyl-1-(2-oxo-2H-pyran-5-yl)-7-(2-(pyrrolidin-1-yl)acetamido)hexadecahydronaphtho[1',2':6,7]indeno[1,7a-b]oxiren-2-yl acetate, (1R,2R,2aR,3aS,3bR,5aS,7S,9aR,9bS,11aR)-5a-hydroxy-9a,11a-dimethyl-7-(1-methylpyrrolidine-2-carboxamido)-1-(2-oxo-2H-pyran-5-yl)hexadecahydronaphtho[1',2':6,7]indeno[1,7a-b]oxiren-2-yl acetate, (1R,2R,2aR,3aS,3bR,5aS,7S,9aR,9bS,11aR)-5a-hydroxy-7-((methoxycarbonyl)amino)-9a,11a-dimethyl-1-(2-oxo-2H-pyran-5-yl)hexadecahydronaphtho[1',2':6,7]indeno[1,7a-b]oxiren-2-yl acetate, (1R,2R,2aR,3aS,3bR,5aS,7 S,9aR,9bS,11aR)-5a-hydroxy-7-((methoxycarbonyl)(methyl)amino)-9a,11a-dimethyl-1-(2-oxo-2H-pyran-5-yl)hexadecahydronaphtho[1',2':6,7]indeno[1,7a-b]oxiren-2-yl acetate, (1R,2R,2aR,3aS,3bR,5aS,7S,9aR,9bS,11aR)-5a-hydroxy-9a,11a-dimethyl-7-(methyl((2-(pyrrolidin-1-yl)ethoxy)carbonyl)amino)-1-(2-oxo-2H-pyran-5-yl)hexadecahydronaphtho[1',2':6,7]indeno[1,7a-b]oxiren-2-yl acetate, (1R,2R,2aR,3aS,3bR,5aS,7S,9aR,9bS,11aR)-5a-hydroxy-9a,11a-dimethyl-7-(methyl((2-morpholinoethoxy)carbonyl)amino)-1-(2-oxo-2H-pyran-5-yl)hexadecahydronaphtho[1',2':6,7]indeno[1,7a-b]oxiren-2-yl acetate, (1R,2R,2aR,3aS,3bR,5aS,7S,9aR,9bS,11aR)-5a-hydroxy-9a,11a-dimethyl-7-(1-methyl-3-(2-(pyrrolidin-1-yl)ethyl)ureido)-1-(2-oxo-2H-pyran-5-yl)hexadecahydronaphtho[1',2':6,7]indeno[1,7a-b]oxiren-2-yl acetate, (1R,2R,2aR,3aS,3bR,5aS,7S,9aR,9bS,11aR)-5a-hydroxy-9a,11a-dimethyl-7-(N-methylpiperazine-1-carboxamido)-1-(2-oxo-2H-pyran-5-yl)hexadecahydronaphtho[1',2':6,7]indeno[1,7a-b]oxiren-2-yl acetate, (1R,2R,2aR,3aS,3bR,5aS,7S,9aR,9bS,11aR)-7-(N,4-dimethylpiperazine-1-carboxamido)-5a-hydroxy-9a,11a-dimethyl-1-(2-oxo-2H-pyran-5-yl)hexadecahydronaphtho[1',2':6,7]indeno[1,7a-b]oxiren-2-yl acetate, (1R,2R,2aR,3aS,3bR,5aS,7S,9aR,9bS,11aR)-5a-hydroxy-9a,11a-dimethyl-1-(2-oxo-2H-pyran-5-yl)-7-(3-(piperidin-4-yl)ureido)hexadecahydronaphtho[1',2':6,7]indeno[1,7a-b]oxiren-2-yl acetate, (1R,2R,2aR,3aS,3bR,5aS,7S,9aR,9bS,11aR)-5a-hydroxy-9a,11a-dimethyl-7-(N-methyl-1,4-diazepane-1-carboxamido)-1-(2-oxo-2H-pyran-5-yl)hexadecahydronaphtho[1',2':6,7]indeno[1,7a-b]oxiren-2-yl acetate, (1R,2R,2aR,3aS,3bR,5aS,7S,9aR,9bS,11aR)-7-(N,4-dimethyl-1,4-diazepane-1-carboxamido)-5a-hydroxy-9a,11a-dimethyl-1-(2-oxo-2H-pyran-5-yl)hexadecahydronaphtho[1',2':6,7]indeno[1,7a-b]oxiren-2-yl acetate, (1R,2R,2aR,3aS,3bR,5aS,7 S,9aR,9bS,11aR)-5a-hydroxy-9a,11a-dimethyl-1-(2-oxo-2H-pyran-5-yl)-7-(piperidin-1-yl)hexadecahydronaphtho[1',2':6,7]indeno[1,7a-b]oxiren-2-yl acetate, (1R,2R,2aR,3aS,3bR,5aS,7S,9aR,9bS,11aR)-5a-hydroxy-9a,11a-dimethyl-1-(2-oxo-2H-pyran-5-yl)-7-(piperazin-1-yl)hexadecahydronaphtho[1',2':6,7]indeno[1,7a-b]oxiren-2-yl acetate, (1R,2R,2aR,3aS,3bR,5aS,7S,9aR,9bS,11aR)-5a-hydroxy-9a,11a-dimethyl-7-(4-methylpiperazin-1-yl)-1-(2-oxo-2H-pyran-5-yl)hexadecahydronaphtho[1',2':6,7]indeno[1,7a-b]oxiren-2-yl acetate, (1R,2R,2aR,3aS,3bR,5aS,7S,9aR,9bS,11aR)-5a-hydroxy-9a,11a-dimethyl-7-morpholino-1-(2-oxo-2H-pyran-5-yl)hexadecahydronaphtho[1',2':6,7]indeno[1,7a-b]oxiren-2-yl acetate, (1R,2R,2aR,3aS,3bR,5aS,9aR,9bS,11aR)-5a-hydroxy-9a,11a-dimethyl-1-(2-oxo-2H-pyran-5-yl)-7-(piperazin-1-yl)hexadecahydronaphtho[1',2':6,7]indeno[1,7a-b]oxiren-2-yl acetate, (1R,2R,2aR,3aS,3bR,5aS,9aR,9bS,11aR)-5a-hydroxy-9a,11a-dimethyl-1-(2-oxo-2H-pyran-5-yl)-7-(pyrrolidin-1-yl)hexa decahydronaphtho[1',2':6,7]indeno[1,7a-b]oxiren-2-yl acetate, (1R,2R,2aR,3aS,3bR,5aS,7S,9aR,9bS,11aR)-5a-hydroxy-9a,11a-dimethyl-7-(N-methylmorpholine-4-carboxamido)-1-(2-oxo-2H-pyran-5-yl)hexadecahydronaphtho[1',2':6,7]indeno[1,7a-b]oxiren-2-yl acetate, (1R,2R,2aR,3aS,3bR,5aS,7S,9aR,9bS,11aR)-5a-hydroxy-9a,11a-dimethyl-7-(1-methyl-3-(2-(3-oxopiperazin-1-yl)ethyl)ureido)-1-(2-oxo-2H-pyran-5-yl)hexadecahydronaphtho[1',2':6,7]indeno[1,7a-b]oxiren-2-yl acetate, 4-((3S,5R,8R,9S,10S,13R,14S,17R)-14-hydroxy-10,13-dimethyl-3-(pyrrolidin-1-yl)hexadecahydro-1H-cyclopenta[a]phenanthren-17-yl)furan-2(5H)-one, 4-((3S,5R,8R,9S,10S,13R,14S,17R)-14-hydroxy-3-((R)-3-hydroxypyrrolidin-1-yl)-10,13-dimethylhexadecahydro-1H-cyclopenta[a]phenanthren-17-yl)furan-2(5H)-one, 4-((3S,5R,8R,9S,10S,13R,14S,17R)-14-hydroxy-3-((S)-3-hydroxypyrrolidin-1-yl)-10,13-dimethylhexadecahydro-1H-cyclopenta[a]phenanthren-17-yl)furan-2(5H)-one, 4-((3S,5R,8R,9S,10S,13R,14S,17R)-3-((R)-3-aminopyrrolidin-1-yl)-14-hydroxy-10,13-dimethylhexadecahydro-1H-cyclopenta[a]phenanthren-17-yl)furan-2(5H)-one, 4-((3S,5R,8R,9S,10S,13R,14S,17R)-3-((S)-3-aminopyrrolidin-1-yl)-14-hydroxy-10,13-dimethylhexadecahydro-1H-cyclopenta[a]phenanthren-17-yl)furan-2(5H)-one, 4-((3S,5R,8R,9S,10S,13R,14S,17R)-14-hydroxy-10,13-dimethyl-3-(piperidin-4-ylamino)hexadecahydro-1H-cyclopenta[a]phenanthren-17-yl)furan-2(5H)-one, 4-((3S,5R,8R,9S,10S,13R,14S,17R)-14-hydroxy-10,13-dimethyl-3-(methyl(piperidin-4-yl)amino)hexadecahydro-1H-cyclopenta[a]phenanthren-17-yl)furan-2(5H)-one, 4-((3S,5R,8R,9S,10S,13R,14S,17R)-14-hydroxy-10,13-dimethyl-3-(piperidin-1-yl)hexadecahydro-1H-cyclopenta[a]phenanthren-17-yl)furan-2(5H)-one, 4-((3S,5R,8R,9S,10S,13R,14S,17R)-14-hydroxy-3-(3-hydroxypiperidin-1-yl)-10,13-dimethylhexadecahydro-1H-cyclopenta[a]phenanthren-17-yl)furan-2(5H)-one, 4-((5R,8R,9S,10S,13R,14S,17R)-14-hydroxy-10,13-dimethyl-3-(piperazin-1-yl)hexadecahydro-1H-cyclopenta[a]phenanthren-17-yl)furan-2(5H)-one, 4-((3S,5R,8R,9S,10S,13R,14S,17R)-14-hydroxy-10,13-dimethyl-3-(piperazin-1-yl)hexadecahydro-1H-cyclopenta[a]phenanthren-17-yl)furan-2(5H)-one, 4-((3S,5R,8R,9S,10S,13R,14S,17R)-14-hydroxy-10,13-dimethyl-3-morpholinohexadecahydro-1H-cyclopenta[a]phenanthren-17-yl)furan-2(5H)-one, 4-((3S,5R,8R,9S,10S,13R,14S,17R)-14-hydroxy-3-((R)-3-(hydroxymethyl)morpholino)-10,13-dimethylhexadecahydro-1H-cyclopenta[a]phenanthren-17-yl)furan-2(5H)-one, 4-((3S,5R,8R,9S,10S,13R,14S,17R)-3-((R)-3-(aminomethyl)morpholino)-14-hydroxy-10,13-dimethylhexadecahydro-1H-cyclopenta[a]phenanthren-17-yl)furan-2(5H)-one, 4-((3S,5R,8R,9S,10S,13R,14S,17R)-14-hydroxy-3-((S)-3-(hydroxymethyl)morpholino)-10,13-dimethylhexadecahydro-1H-cyclopenta[a]phenanthren-17-yl)furan-2(5H)-one, 4-((3S,5R,8R,9S,10S,13R,14S,17R)-34S)-3-(aminomethyl)morpholino)-14-hydroxy-10,13-dimethylhexadecahydro-1H-cyclopenta[a]phenanthren-17-yl)furan-2(5H)-one, 4-((3S,5R,8R,9S,10S,13R,14S,17R)-14-hydroxy-3-((S)-2-(hydroxymethyl)piperazin-1-yl)-10,13-dimethylhexadecahydro-1H-cyclopenta[a]phenanthren-17-yl)furan-2(5H)-one, 4-((3S,5R,8R,9S,10S,13R,14S,17R)-14-hydroxy-3-((R)-2-(hydroxymethyl)piperazin-1-yl)-10,13-dimethylhexadecahydro-1H-cyclopenta[a]phenanthren-17-yl)furan-2(5H)-one, 4-((3S,5R,8R,9S,10S,13R,14S,17R)-14-hydroxy-3-((R)-2-(hydroxymethyl)morpholino)-10,13-dimethylhexadecahydro-1H-cyclopenta[a]phenanthren-17-yl)furan-2(5H)-one, 4-((3S,5R,8R,9S,10S,13R,14S,17R)-14-hydroxy-3-((5)-2-(hydroxymethyl)morpholino)-10,13-dimethylhexadecahydro-1H-cyclopenta[a]phenanthren-17-yl)furan-2(5H)-one, 4-((3S,5R,8R,9S,10S,13R,14S,17R)-3-((R)-2-(aminomethyl)morpholino)-14-hydroxy-10,13-dimethylhexadecahydro-1H-cyclopenta[a]phenanthren-17-yl)furan-2(5H)-one, 4-((3S,5R,8R,9S,10S,13R,14S,17R)-3-4S)-2-(aminomethyl)morpholino)-14-hydroxy-10,13-dimethylhexadecahydro-1H-cyclopenta[a]phenanthren-17-yl)furan-2(5H)-one, 4-((3S,5R,8R,9S,10S,13R,14S,17R)-14-hydroxy-3-(R)-3-(hydroxymethyl)piperazin-1-yl)-10,13-dimethylhexadecahydro-1H-cyclopenta[a]phenanthren-17-yl)furan-2(5H)-one, 4-((3S,5R,8R,9S,10S,13R,14S,17R)-14-hydroxy-3-((S)-3-(hydroxymethyl)piperazin-1-yl)-10,13-dimethylhexadecahydro-1H-cyclopenta[a]phenanthren-17-yl)furan-2(5H)-one, 4-((3S,5R,8R,9S,10S,13R,14S,17R)-3-((R)-3-(aminoethyl)piperazin-1-yl)-14-hydroxy-10,13-dimethylhexadecahydro-1H-cyclopenta[a]phenanthren-17-yl)furan-2(5H)-one, 4-((3S,5R,8R,9S,10S,13R,14S,17R)-3-((S)-3-(aminomethyl)piperazin-1-yl)-14-hydroxy-10,13-dimethylhexadecahydro-1H-cyclopenta[a]phenanthren-17-yl)furan-2(5H)-one, N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)methanesulfonamide, methyl ((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)(methyl)carbamate, 2-aminoethyl ((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)(methyl)carbamate, 2-hydroxyethyl ((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)(methyl)carbamate, 2-(3-oxopiperazin-1-yl)ethyl ((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)(methyl)carbamate, 2-(pyrrolidin-1-yl)ethyl ((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)(methyl)carbamate, 2-morpholinoethyl ((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)(methyl)carbamate, 3-(2-aminoethyl)-1-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-1-methylurea, 1-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-3-(2-hydroxyethyl)-1-methylurea, 1-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-1-methyl-3-(2-(pyrrolidin-1-yl)ethyl)urea, 1-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-1-methyl-3-(2-morpholinoethyl)urea, N-((5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-N-methylpiperazine-1-carboxamide, N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-N-methylpiperazine-1-carboxamide, N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-N-(2-hydroxyethyl)piperazine-1-carboxamide, (R)—N-((3S,5R,8R,9S,10S,13R,14S,17R)-14-hydroxy-10,13-dimethyl-17-(5-oxo-2,5-dihydrofuran-3-yl)hexa decahydro-1H-cyclopenta[a]phenanthren-3-yl)-3-(hydroxymethyl)-N-methylpiperazine-1-carboxamide, (S)—N-((3S,5R,8R,9S,10S,13R,14S,17R)-14-hydroxy-10,13-dimethyl-17-(5-oxo-2,5-dihydrofuran-3-yl)hexa decahydro-1H-cyclopenta[a]phenanthren-3-yl)-3-(hydroxymethyl)-N-methylpiperazine-1-carboxamide, (S)—N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-2-(hydroxymethyl)-N-methylpiperazine-1-carboxamide, (R)—N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-2-(hydroxymethyl)-N-methylpiperazine-1-carboxamide, N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-N,4-dimethylpiperazine-1-carboxamide, N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-N-methyl-1,4-diazepane-1-carboxamide, (S)-3-hydroxy-N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-N-methylpyrrolidine-1-carboxamide, (R)-3-hydroxy-N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-N-methylpyrrolidine-1-carboxamide, 1-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-3-(2-((S)-3-hydroxypyrrolidin-1-yl)ethyl)-1-methylurea, 1-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-3-(2-((R)-3-hydroxypyrrolidin-1-yl)ethyl)-1-methylurea, N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-2-(pyrrolidin-1-yl)acetamide, 2-amino-N-((3S,5R,8R,9S,10S,13R,14S,17R)-14-hydroxy-10,13-dim ethyl-17-(5-oxo-2,5-dihydrofuran-3-yl)hexadecahydro-1H-cyclopenta[a]phenanthren-3-yl)-N-methylacetamide, (R)-2-amino-N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-N-methylpropanamide, (S)-2-amino-N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-N-methylpropanamide, (R)-2-amino-N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-N,3-dimethylbutanamide, (S)-2-amino-N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-N,3-dimethylbutanamide, (R)-2-amino-N1-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-N1-methylsuccinamide, (S)-2-amino-N1-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)N1-methylsuccinamide, (R)—N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)pyrrolidine-2-carboxamide, (S)—N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)pyrrolidine-2-carboxamide, (S)—N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-N-methylpyrrolidine-2-carboxamide, (R)—N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-N-methylpyrrolidine-2-carboxamide, 4-((3S,5R,8R,9S,10S,12R,13S,14S,17R)-12,14-dihydroxy-10,13-dimethyl-3-(pyrrolidin-1-yl)hexadecahydro-1H-cyclopenta[a]phenanthren-17-yl)furan-2(5H)-one, 4-((3S,5R,8R,9S,10S,12R,13S,14S,17R)-12,14-dihydroxy-3-((R)-3-hydroxypyrrolidin-1-yl)-10,13-dimethylhexadecahydro-1H-cyclopenta[a]phenanthren-17-yl)furan-2(5H)-one, 4-((3S,5R,8R,9S,10S,12R,13S,14S,17R)-12,14-dihydroxy-3-((S)-3-hydroxypyrrolidin-1-yl)-10,13-dimethylhexadecahydro-1H-cyclopenta[a]phenanthren-17-yl)furan-2(5H)-one, 4-((3S,5R,8R,9S,10S,12R,13S,14S,17R)-12,14-dihydroxy-10,13-dimethyl-3-(piperidin-4-ylamino)hexadecahydro-1H-cyclopenta[a]phenanthren-17-yl)furan-2(5H)-one, 4-((3S,5R,8R,9S,10S,12R,13S,14S,17R)-12,14-dihydroxy-10,13-dimethyl-3-(methyl(piperidin-4-yl)amino)hexadecahydro-1H-cyclopenta[a]phenanthren-17-yl)furan-2(5H)-one, 4-((3S,5R,8R,9S,10S,12R,13S,14S,17R)-12,14-dihydroxy-10,13-dimethyl-3-(piperidin-1-yl)hexadecahydro-1H-cyclopenta[a]phenanthren-17-yl)furan-2(5H)-one, 4-((3S,5R,8R,9S,10S,12R,13S,14S,17R)-12,14-dihydroxy-3-(3-hydroxypiperidin-1-yl)-10,13-dimethylhexadecahydro-1H-cyclopenta[a]phenanthren-17-yl)furan-2(5H)-one, 4-((5R,8R,9S,10S,12R,13S,14S,17R)-12,14-dihydroxy-10,13-dimethyl-3-(piperazin-1-yl)hexadecahydro-1H-cyclopenta[a]phenanthren-17-yl)furan-2(5H)-one, 4-((3S,5R,8R,9S,10S,12R,13S,14S,17R)-12,14-dihydroxy-10,13-dimethyl-3-(piperazin-1-yl)hexadecahydro-1H-cyclopenta[a]phenanthren-17-yl)furan-2(5H)-one, 4-((3S,5R,8R,9S,10S,12R,13S,14S,17R)-12,14-dihydroxy-10,13-dimethyl-3-morpholinohexadecahydro-1H-cyclopenta[a]phenanthren-17-yl)furan-2(5H)-one, N-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)methanesulfonamide, methyl ((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)(methyl)carbamate, 2-aminoethyl ((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)(methyl)carbamate, 2-hydroxyethyl ((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)(methyl)carbamate, 2-(pyrrolidin-1-yl)ethyl ((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)(methyl)carbamate, 2-morpholinoethyl ((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)(methyl)carbamate, 3-(2-aminoethyl)-1((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)-1-methylurea, 1-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)-3-(2-hydroxyethyl)-1-methylurea, 1-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)-1-methyl-3-(2-morpholinoethyl)urea, N-((5R,8R,9S,10S,12R,13S,14S,17R)-12,14-dihydroxy-10,13-dimethyl-17-(5-oxo-2,5-dihydrofuran-3-yl)hexa decahydro-1H-cyclopenta[a]phenanthren-3-yl)piperazine-1-carboxamide, N-((5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)-N-methylpiperazine-1-carboxamide, N-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)-N-methylpiperazine-1-carboxamide, N-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)-N-(2-hydroxyethyl)piperazine-1-carboxamide, N-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)-N,4-dimethylpiperazine-1-carboxamide, N-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)-N-methyl-1,4-diazepane-1-carboxamide, (S)—N-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)-3-hydroxy-N-methylpyrrolidine-1-carb oxamide, (R)—N-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)-3-hydroxy-N-methylpyrrolidine-1-carb oxamide, N-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)-2-(pyrrolidin-1-yl)acetamide, N-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)-2-morpholinoacetamide, 2-amino-N-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)acetamide, 2-amino-N-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)-N-methylacetamide, (R)-2-amino-N-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)-N-methylpropanamide, (S)-2-amino-N-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)-N-methylpropanamide, (R)-2-amino-N-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)-N,3-dimethylbutanamide, (S)-2-amino-N-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)-N,3-dimethylbutanamide, (R)-2-amino-N-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)propanamide, (5)-2-amino-N-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)propanamide, (R)-2-amino-N-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)-3-methylbutanamide, (S)-2-amino-N-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)-3-methylbutanamide, (R)—N-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)pyrrolidine-2-carboxamide, (S)—N-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)pyrrolidine-2-carboxamide, (S)—N-((3S,5R,8R,9S,10S,12R,13S,14S,17R)-12,14-dihydroxy-10,13-dimethyl-17-(5-oxo-2,5-dihydrofuran-3-yl)hexadecahydro-1H-cyclopenta[a]phenanthren-3-yl)-N-methylpyrrolidine-2-carboxamide, (R)—N-((3S,5R,8R,9S,10S,12R,13S,14S,17R)-12,14-dihydroxy-10,13-dimethyl-17-(5-oxo-2,5-dihydrofuran-3-yl)

hexadecahydro-1H-cyclopenta[a]phenanthren-3-yl)-N-methylpyrrolidine-2-carboxamide, (3S,5R,8R,9S,10S,13R,14S,16S,17R)-14-hydroxy-10,13-dimethyl-17-(5-oxo-2,5-dihydrofuran-3-yl)-3-(pyrrolidin-1-yl)hexadecahydro-1H-cyclopenta[a]phenanthren-16-yl acetate, (3S,5R,8R,9S,10S,13R,14S,16S,17R)-14-hydroxy-10,13-dimethyl-17-(5-oxo-2,5-dihydrofuran-3-yl)-3-(piperidin-1-yl)hexadecahydro-1H-cyclopenta[a]phenanthren-16-yl acetate, (5R,8R,9S,10S,13R,14S,16S,17R)-14-hydroxy-10,13-dimethyl-17-(5-oxo-2,5-dihydrofuran-3-yl)-3-(piperazin-1-yl)hexadecahydro-1H-cyclopenta[a]phenanthren-16-yl acetate, (3S,5R,8R,9S,10S,13R,14S,16S,17R)-3-(N,4-dimethylpiperazine-1-carboxamido)-14-hydroxy-10,13-dimethyl-17-(5-oxo-2, 5-dihydrofuran-3-yl)hexadecahydro-1H-cyclopenta[a]phenanthren-16-yl acetate, (5R,8R,9S,10S,13R,14S,16S,17R)-14-hydroxy-10,13-dimethyl-3-(4-methyl-1,4-diazepan-1-yl)-17-(5-oxo-2,5-dihydrofuran-3-yl)hexadecahydro-1H-cyclopenta[a]phenanthren-16-yl acetate, (3S,5R,8R,9S,10S,13R,14S,16S,17R)-14-hydroxy-10,13-dimethyl-17-(5-oxo-2,5-dihydrofuran-3-yl)-3-(piperazin-1-yl)hexadecahydro-1H-cyclopenta[a]phenanthren-16-yl acetate, (3S,5R,8R,9S,10S,13R,14S,16S,17R)-14-hydroxy-10,13-dimethyl-3-(4-methylpiperazin-1-yl)-17-(5-oxo-2,5-dihydrofuran-3-yl)hexadecahydro-1H-cyclopenta[a]phenanthren-16-yl acetate, (3S,5R,8R,9S,10S,13R,14S,16S,17R)-14-hydroxy-10,13-dimethyl-3-morpholino-17-(5-oxo-2,5-dihydrofuran-3-yl)hexadecahydro-1H-cyclopenta[a]phenanthren-16-yl acetate, (3S,5R,8R,9S,10S,13R,14S,16S,17R)-14-hydroxy-10,13-dimethyl-3-(methylsulfonamido)-17-(5-oxo-2,5-dihydrofuran-3-yl)hexadecahydro-1H-cyclopenta[a]phenanthren-16-yl acetate, (3S,5R,8R,9S,10S,13R,14S,16S,17R)-14-hydroxy-3-((methoxycarbonyl)(methyl)amino)-10,13-dimethyl-17-(5-oxo-2,5-dihydrofuran-3-yl)hexadecahydro-1H-cyclopenta[a]phenanthren-16-yl acetate, (3S,5R,8R,9S,10S,13R,14S,16S,17R)-3-(((2-aminoethoxy)carbonyl)(methyl)amino)-14-hydroxy-10,13-dimethyl-17-(5-oxo-2, 5-dihydrofuran-3-yl)hexadecahydro-1H-cyclopenta[a]phenanthren-16-yl acetate, (3S,5R,8R,9S,10S,13R,14S,16S,17R)-14-hydroxy-3-(((2-hydroxyethoxy)carbonyl)(methyl)amino)-10,13-dimethyl-17-(5-oxo-2,5-dihydrofuran-3-yl)hexadecahydro-1H-cyclopenta[a]phenanthren-16-yl acetate, (3S,5R,8R,9S,10S,13R,14S,16S,17R)-14-hydroxy-10,13-dimethyl-3-(methyl((2-(pyrrolidin-1-yl)ethoxy)carbonyl)amino)-17-(5-oxo-2,5-dihydrofuran-3-yl)hexadecahydro-1H-cyclopenta[a]phenanthren-16-yl acetate, (3S,5R,8R,9S,10S,13R,14S,16S,17R)-14-hydroxy-10,13-dimethyl-3-(methyl((2-morpholinoethoxy)carbonyl)amino)-17-(5-oxo-2,5-dihydrofuran-3-yl)hexadecahydro-1H-cyclopenta[a]phenanthren-16-yl acetate, (3S,5R,8R,9S,10S,13R,14S,16S,17R)-14-hydroxy-10,13-dimethyl-3-(1-methyl-3-(2-(pyrrolidin-1-yl)ethyl)ureido)-17-(5-oxo-2,5-dihydrofuran-3-yl)hexadecahydro-1H-cyclopenta[a]phenanthren-16-yl acetate, (3S,5R,8R,9S,10S,13R,14S,16S,17R)-14-hydroxy-10,13-dimethyl-3-(1-methyl-3-(2-morpholinoethyl)ureido)-17-(5-oxo-2,5-dihydrofuran-3-yl)hexadecahydro-1H-cyclopenta[a]phenanthren-16-yl acetate, (5R,8R,9S,10S,13R,14S,16S,17R)-14-hydroxy-10,13-dimethyl-3-(N-methylpiperazine-1-carboxamido)-17-(5-oxo-2,5-dihydrofuran-3-yl)hexadecahydro-1H-cyclopenta[a]phenanthren-16-yl acetate, (3S,5R,8R,9S,10S,13R,14S,16S,17R)-14-hydroxy-10,13-dimethyl-3-(N-methylpiperazine-1-carboxamido)-17-(5-oxo-2,5-dihydrofuran-3-yl)hexadecahydro-1H-cyclopenta[a]phenanthren-16-yl acetate, (3S,5R,8R,9S,10S,13R,14S,16S,17R)-14-hydroxy-10,13-dimethyl-17-(5-oxo-2,5-dihydrofuran-3-yl)-3-(2-(pyrrolidin-1-yl)acetamido)hexadecahydro-1H-cyclopenta[a]phenanthren-16-yl acetate, (3S,5R,8R,9S,10S,13R,14S,16S,17R)-14-hydroxy-10,13-dimethyl-3-(N-methyl-2-(pyrrolidin-1-yl)acetamido)-17-(5-oxo-2,5-dihydrofuran-3-yl)hexadecahydro-1H-cyclopenta[a]phenanthren-16-yl acetate, (3S,5R,8R,9S,10S,13R,14S,16S,17R)-14-hydroxy-10,13-dimethyl-3-(2-morpholinoacetamido)-17-(5-oxo-2,5-dihydrofuran-3-yl)hexadecahydro-1H-cyclopenta[a]phenanthren-16-yl acetate, (3S,5R,8R,9S,10S,13R,14S,16S,17R)-14-hydroxy-10,13-dimethyl-3-(N-methyl-2-morpholinoacetamido)-17-(5-oxo-2,5-dihydrofuran-3-yl)hexadecahydro-1H-cyclopenta[a]phenanthren-16-yl acetate, 2-(pyrrolidin-1-yl)ethyl ((3S,5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)(methyl)carbamate, methyl ((3S,5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)(methyl)carbamate, 2-morpholinoethyl ((3S,5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)(methyl)carbamate, 1-((3S,5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)-1-methyl-3-(2-(pyrrolidin-1-yl)ethyl)urea, 1-((3S,5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)-1-methyl-3-(2-morpholinoethyl)urea, N-((3S,5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)-N-methylmorpholine-4-carboxamide, N-((5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)-N-methylpiperazine-1-carboxamide, N-((3S,5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)-N-methylpiperazine-1-carboxamide, N-((3S,5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)-4-methyl-1,4-diazepane-1-carboxamide, N-((3S,5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)-N-methyl-1,4-diazepane-1-carboxamide, N-((3S,5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)-N-methyl-2-(pyrrolidin-1-yl)acetamide, N-((3S,5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)-N-methyl-2-morpholinoacetamide, (S)—N-((3S,5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)pyrrolidine-2-carboxamide, (R)—N-((3S,5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)pyrrolidine-2-carboxamide, N-((3S,5R,8R,9S,10S,13R,17S)-10,13-dimethyl-17-(2-oxo-2H-pyran-5-yl)-2,3,4,5,6,7,8,9,10,11,12,13,16,17-tetradecahydro-1H-cyclopenta[a]phenanthren-3-yl)methanesulfonamide, 5-((5R,8R,9S,10S,13R,17S)-10,13-dimethyl-3-morpholino-2,3,4,5,6,7,8,9,10,11,12,13,16,17-tetradecahydro-1H-cyclopenta[a]phenanthren-17-yl)-2H-pyran-2-one, 5-((5R,8R,9S,10S,13R,17S)-10,13-dimethyl-3-(piperidin-1-yl)-2,3,4,5,6,7,8,9,10,11,12,13,16,17-tetradecahydro-1H-cyclopenta[a]phenanthren-17-yl)-2H-pyran-2-one, 5-((5R,8R,9S,10S,13R,17S)-10,13-dimethyl-3-(pyrrolidin-1-yl)-2,3,4,5,6,7,8,9,10,11,12,13,16,17-tetradecahydro-1H-cyclopenta[a]phenanthren-17-yl)-2H-pyran-2-one, 5-((3S,5R,8R,9S,10S,13R,17S)-10,13-dimethyl-3-(piperazin-1-yl)-2,3,4,5,6,7,8,9,10,11,12,13,16,17-tetradecahydro-1H-cyclopenta[a]phenanthren-17-yl)-2H-pyran-2-one, 5-((5R,8R,9S,10S,13R,17S)-10,13-dimethyl-3-(4-methyl-1,4-diazepan-1-yl)-2,3,4,5,6,7,8,9,10,11,12,13,16,17-tetradecahydro-1H-cyclopenta[a]phenanthren-17-yl)-2H-pyran-2-one, 5-((5R,8R,9S,10S,13R,17S)-3-(1,4-diazepan-1-yl)-10,13-dimethyl-2,3,4,5,6,7,8,9,10,11,12,13,16,17-tetradecahydro-1H-cyclopenta[a]phenanthren-17-yl)-2H-pyran-2-one, 5-((5R,8R,9S,10S,13R,17S)-10,13-dimethyl-3-(piperazin-1-yl)-2,3,4,5,6,7,8,9,10,11,12,13,16,17-tetradecahydro-1H-cyclopenta[a]phenanthren-17-yl)-2H-pyran-2-one, 5-((3S,5R,8R,9S,10S,13R,17S)-10,13-dimethyl-3-(4-methylpiperazin-1-yl)-2,3,4,5,6,7,8,9,10,11,12,13,16,17-tetradecahydro-1H-cyclopenta[a]phenanthren-17-yl)-2H-pyran-2-one, methyl ((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)(methyl)carbamate, 2-(pyrrolidin-1-yl)ethyl ((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)(methyl)carbamate, 2-morpholinoethyl ((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)(methyl)carbamate, 1-((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)-1-methyl-3-(2-(pyrrolidin-1-yl)ethyl)urea, 1-((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)-1-methyl-3-(2-morpholinoethyl)urea, N-((5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)-N-methylpiperazine-1-carboxamide, N-((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)-N-methylpiperazine-1-carboxamide, N-((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)-N,4-dimethylpiperazine-1-carboxamide, N-((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)-N-methyl-1,4-diazepane-1-carboxamide, (S)—N-((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)-3-hydroxy-N-methylpyrrolidine-1-carboxamide, (R)—N-((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)-3-hydroxy-N-methylpyrrolidine-1-carboxamide, N-((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)-2-(pyrrolidin-1-yl)acetamide, N-((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)-2-morpholinoacetamide, N-((3S,5R,8R,9S,10S,13R,17S)-10,13-dimethyl-17-(5-oxo-2,5-dihydrofuran-3-yl)-2,3,4,5,6,7,8,9,10,11,12,13,16,17-tetradecahydro-1H-cyclopenta[a]phenanthren-3-yl)methanesulfonamide, 4-((3S,5R,8R,9S,10S,13R,17S)-10,13-dimethyl-3-(piperazin-1-yl)-2,3,4,5,6,7,8,9,10,11,12,13,16,17-tetradecahydro-1H-cyclopenta[a]phenanthren-17-yl) furan-2(5H)-one, 4-((5R,8R,9S,10S,13R,17S)-10,13-dimethyl-3-(4-methylpiperazin-1-yl)-2,3,4,5,6,7,8,9,10,11,12,13,16,17-tetradecahydro-1H-cyclopenta[a]phenanthren-17-yl) furan-2(5H)-one, 4-((5R,8R,9S,10S,13R,17S)-10,13-dimethyl-3-(piperazin-1-yl)-2,3,4,5,6,7,8,9,10,11,12,13,16,17-tetradecahydro-1H-cyclopenta[a]phenanthren-17-yl)furan-2(5H)-one, 4-((5R,8R,9S,10S,13R,17S)-10,13-dimethyl-3-morpholino-2,3,4,5,6,7,8,9,10,11,12,13,16,17-tetradecahydro-1H-cyclopenta[a]phenanthren-17-yl)furan-2(5H)-one, 4-((5R,8R,9S,10S,13R,17S)-10,13-dimethyl-3-(piperidin-1-yl)-2,3,4,5,6,7,8,9,10,11,12,13,16,17-tetradecahydro-1H-cyclopenta[a]phenanthren-17-yl)furan-2(5H)-one, 4-((5R,8R,9S,10S,13R,17S)-3-(1,4-diazepan-1-yl)-10,13-dimethyl-2,3,4,5,6,7,8,9,10,11,12,13,16,17-tetradecahydro-1H-cyclopenta[a]phenanthren-17-yl) furan-2(5H)-one, 4-((5R,8R,9S,10S,12R,13S,14S,17R)-3-amino-12,14-dihydroxy-10,13-dimethylhexadecahydro-1H-cyclopenta[a]phenanthren-17-yl)furan-2(5H)-one, (1R,2R,2aR,3aS,3bR,5aR,7S,9aS,9bS,11aR)-9a,11a-dimethyl-7-(N-methylmorpholine-4-carboxamido)-1-(2-oxo-2H-pyran-5-yl)hexadecahydronaphtho[1',2':6,7]indeno[1,7a-b]oxiren-2-yl acetate, and 4-((5R,8R,9S,10S,13R,17S)-10,13-dimethyl-3-(4-methyl-1,4-diazepan-1-yl)-2,3,4,5,6,7,8,9,10,11,12,13,16,17-tetradecahydro-1H-cyclopenta[a]phenanthren-17-yl)furan-2(5H)-one, and pharmaceutically acceptable salts thereof.

Also provided is at least one chemical entity chosen from the compounds set forth in Table 1 below and pharmaceutically acceptable salts thereof.

TABLE 1

Illustrative Compounds of the Present Invention

| Compound No. | Chemical Name |
|---|---|
| C01 | N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)morpholine-4-carboxamide |
| C02 | N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)morpholine-4-carboxamide |
| C03 | N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)piperazine-1-carboxamide |
| C04 | N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)piperazine-1-carboxamide |
| C05 | N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)pyrrolidine-1-carboxamide |
| C06 | N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)pyrrolidine-1-carboxamide |
| C07 | 1-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-(2-hydroxyethyl)urea |
| C08 | 1-(2-aminoethyl)-3-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)urea |
| C09 | 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-(2-hydroxyethyl)urea |
| C10 | 1-(2-aminoethyl)-3-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)urea |
| C11 | 2-amino-N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)acetamide |
| C12 | 2-amino-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)acetamide |
| C13 | (S)-N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)pyrrolidine-2-carboxamide |
| C14 | (S)-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)pyrrolidine-2-carboxamide |
| C15 | 5-((5R,8R,9S,10S,13R,14S,17R)-14-hydroxy-10,13-dimethyl-3-(piperazin-1-yl)hexadecahydro-1H-cyclopenta[a]phenanthren-17-yl)-2H-pyran-2-one |
| C16 | N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)methanesulfonamide<br>Chemical Formula: C25H37NO5S<br>Exact Mass: 463.2<br>Molecular Weight: 463.6 |

TABLE 1-continued

Illustrative Compounds of the Present Invention

| Compound No. | Chemical Name |
|---|---|
| C17 | methyl ((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)carbamate |
| C18 | 5-((5R,8R,9S,10S,13R,14S,17R)-14-hydroxy-10,13-dimethyl-3-((2-morpholinoethyl)amino)hexadecahydro-1H-cyclopenta[a]phenanthren-17-yl)-2H-pyran-2-one |
| C19 | 4-((5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)piperazin-2-one |
| C20 | 5-((5R,8R,9S,10S,13R,14S,17R)-14-hydroxy-10,13-dimethyl-3-(pyrrolidin-1-yl)hexadecahydro-1H-cyclopenta[a]phenanthren-17-yl)-2H-pyran-2-one |
| C21 | methyl ((5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)(methyl)carbamate |
| C22 | (2R)-2-amino-N-((5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N,3-dimethylbutanamide |
| C23 | N-((5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N-methylmorpholine-4-carboxamide |
| C24 | N-((5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)piperazine-1-carboxamide |
| C25 | (R)-2-amino-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-methylbutanamide |
| C26 | (R)-2-amino-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)propanamide |
| C27 | 5-((5R,8R,9S,10S,13R,14S,17R)-14-hydroxy-10,13-dimethyl-3-((2-(pyrrolidin-1-yl)ethyl)amino)hexadecahydro-1H-cyclopenta[a]phenanthren-17-yl)-2H-pyran-2-one |
| C28 | 5-((5R,8R,9S,10S,13R,14S,17R)-14-hydroxy-10,13-dimethyl-3-morpholinohexadecahydro-1H-cyclopenta[a]phenanthren-17-yl)-2H-pyran-2-one |
| C29 | (2R)-2-amino-N-((5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)-3-methylbutanamide |
| C30 | N-((5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)morpholine-4-carboxamide |
| C31 | (2R)-N-((5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)pyrrolidine-2-carboxamide |
| C32 | 5-((5R,8R,9S,10S,13R,14S,17R)-14-hydroxy-3-((2-hydroxyethyl)(methyl)amino)-10,13-dimethylhexadecahydro-1H-cyclopenta[a]phenanthren-17-yl)-2H-pyran-2-one |
| C33 | 2-morpholinoethyl ((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)carbamate |
| C34 | 5-((3R,5R,8R,9S,10S,13R,14S,17R)-3-amino-14-hydroxy-10,13-dimethylhexadecahydro-1H-cyclopenta[a]phenanthren-17-yl)-2H-pyran-2-one |
| C35 | 5-((3S,5R,8R,9S,10S,13R,14S,17R)-3-amino-14-hydroxy-10,13-dimethylhexadecahydro-1H-cyclopenta[a]phenanthren-17-yl)-2H-pyran-2-one |

The chemical entities described herein can be synthesized utilizing techniques well known in the art from commercially available starting materials and reagents. For example, the chemical entities described herein can be prepared as illustrated below with reference to the examples and reaction schemes.

Generally, compounds of Formula I may be prepared by the routes described below. Materials used herein are either commercially available or prepared by synthetic methods generally known in the art. These schemes are not limited to the compounds listed or by any particular substituents, which are employed for illustrative purposes. Although various steps of are described and depicted in Schemes A-C, the steps in some cases may be performed in a different order than the order shown in Schemes A-C. Various modifications to these synthetic reaction schemes may be made and will be suggested to one skilled in the art having referred to the disclosure contained in this application. Numbering does not necessarily correspond to that of claims or other tables.

Scheme A

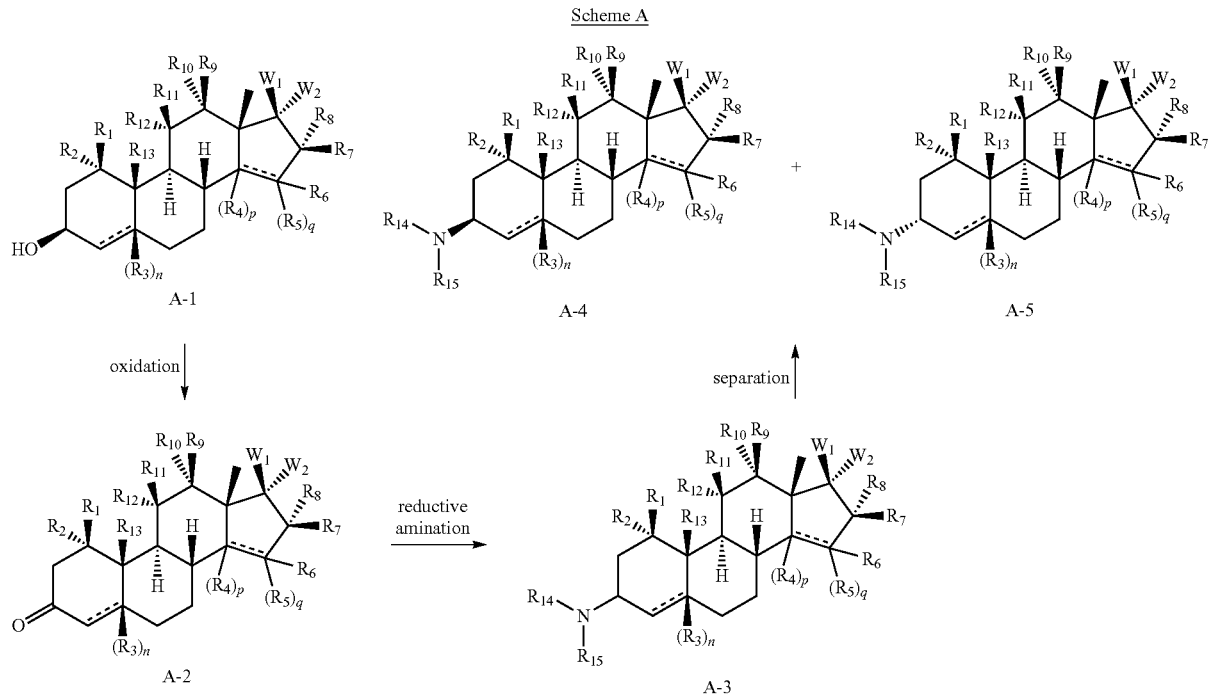

In Scheme A, alcohol A-1 is oxidized to ketone A-2 using an oxidizing agent such as Jone's reagent in acetone. A-2 is then under reductive amination to afford A-3 in the presence of an amine and a reducing agent such as $NaBH_3CN$ in a polar organic solvent such as MeOH. Separation of two diastereoisomers using silica gel chromatography or HPLC afford A-4 and A-5.

In Scheme B, B-1 is synthesized from ketone A-2 is converted to amine B-1 using reductive amination in the presence of an amine and a reducing agent such as $NaBH_3CN$ in a polar organic solvent such as MeOH. B-1 can be first separated to give two diastereoisomers B-2 and B-3, which can be derivatized to afford corresponding B-5 and B-6 respectively. B-1 can also be first derivatized to give B-4, which can be separated to afford B-5 and B-6.

Scheme B

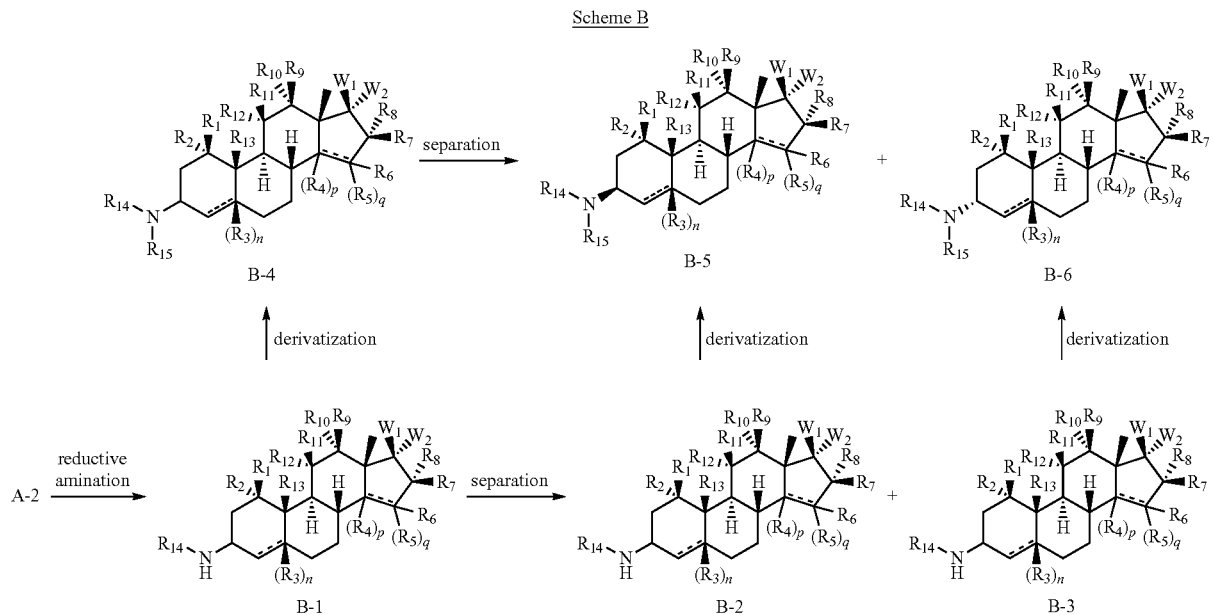

Scheme C

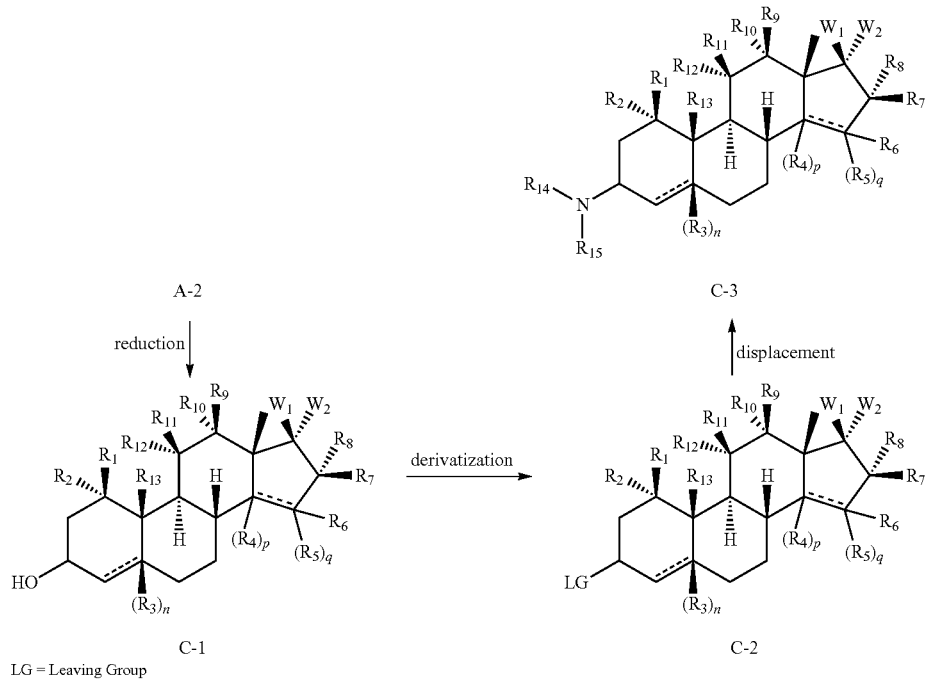

LG = Leaving Group

In Scheme C, ketone A-2 is reduced to give alcohol C-1 as a mixture of two diastereoisomers in the presence of a reducing agent such as $NaBH_4$ in a polar organic solvent such as MeOH or dioxane. The hydroxyl group of C-1 is then converted to a leaving group such as tosyl (OTs), mesyl (OMs) or triflate (OTf). Displacement of the leaving group with amine or heteroaryl such as imidazole, pyrazole, or pyrimidin-4(3H)-one in the presence a base affords C-3. Suitable bases include, but are not limited to, $Et_3N$, pyridine, DMAP, $Na_2CO_3$, $K_2CO_3$, $Cs_2CO_3$, NaOMe, t-BuONa, t-BuOK, NaH, KH, LiH, and $CaH_2$. Suitable solvents include, but are not limited to, DMF, DMSO, DMA, and N-methyl piperidone. The displacement reaction are generally carried out at a temperature ranging from 25-240° C. C-3 can then be separated to afford two corresponding single diastereoisomers. Alternatively, C-1 can be first separated to two single diastereoisomers, which can then be derivatized, displaced to afford the final compound of Formula I.

The desired product can be purified from the reaction mixture by standard methods, e.g. by extraction and/or silica gel chromatography or high-pressure liquid chromatography.

The chemical entities described herein may be prepared in substantially pure form, typically by standard chromatographic methods, prior to formulation in a pharmaceutically acceptable form.

The chemical entities described herein may be used in treating a variety of cancers. Cancers that can be prevented and/or treated by the chemical entities, compositions, and methods described herein include, but are not limited to, human sarcomas and carcinomas, e.g. carcinomas, e.g., colon carcinoma, pancreatic cancer, breast cancer, ovarian cancer, prostate cancer, fibrosarcoma, myxosarcoma, liposarcoma, chondrosarcoma, osteogenic sarcoma, chondroma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wiims' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease.

In some embodiments, the chemical entities described herein arc used for the treatment of cancers of the (i) digestive system including, without limitation, the esophagus, stomach, small intestine, colon (including colorectal), liver & intrahepatic bile duct, gallbladder & other biliary, pancreas, and other digestive organs;

(ii) respiratory system, including without limitation, larynx, lung & bronchus, and other respiratory organs;

(iii) breast;

(iv) genital system, including without limitation, uterine cervix, ovary, and prostate;

(v) urinary system, including without limitation, urinary bladder and kidney and renal pelvis; and (vi) oral cavity & pharynx, including without limitation, tongue, mouth, pharynx, and other oral cavity.

In some embodiments, the chemical entities described herein are used for the treatment of colorectal cancer, liver cancer, lung cancer, breast cancer and oral cancer.

Chemical entities described herein having the desired pharmacological activity may be administered, in some embodiments, as a pharmaceutically acceptable composition comprising an pharmaceutical excipient, to a patient, as described herein. Depending upon the manner of introduction, the chemical entities may be formulated in a variety of ways as discussed below. The concentration of the at least one chemical entity in the formulation may vary from about 0.01-100 wt. %.

The administration of the chemical entities described herein can be done in a variety of ways, including, but not limited to, orally, subcutaneously, intravenously, intranasally, trans dermally, intraperitoneally, intramuscularly, intrapulmonary, vaginally, rectally, or intraocularly.

Pharmaceutical dosage forms include at least one chemical entity described herein and one or more pharmaceutical excipients. As is known in the art, pharmaceutical excipients are secondary ingredients which function to enable or enhance the delivery of a drug or medicine in a variety of dosage forms (e.g.: oral forms such as tablets, capsules, and liquids; topical forms such as dermal, opthalmic, and otic forms; suppositories; injectables; respiratory forms and the like). Pharmaceutical excipients include inert or inactive ingredients, synergists or chemicals that substantively contribute to the medicinal effects of the active ingredient. For example, pharmaceutical excipients may function to improve flow characteristics, product uniformity, stability, taste, or appearance, to case handling and administration of dose, for convenience of use, or to control bioavailability. While pharmaceutical excipients are commonly described as being inert or inactive, it is appreciated in the art that there is a relationship between the properties of the pharmaceutical excipients and the dosage forms containing them.

Pharmaceutical excipients suitable for use as carriers or diluents are well known in the art, and may be used in a variety of formulations. See, e.g., Remington's Pharmaceutical Sciences, 18th Edition, A. R. Gennaro, Editor, Mack Publishing Company (1990); Remington: The Science and Practice of Pharmacy, 21$^{st}$ Edition, Lippincott Williams & Wilkins (2005); Handbook of Pharmaceutical Excipients, 3rd Edition, A. H. Kibbe, Editor, American Pharmaceutical Association, and Pharmaceutical Press (2000); and Handbook of Pharmaceutical Additives, compiled by Michael and Irene Ash, Gower (1995), each of which is incorporated herein by reference for all purposes.

Oral solid dosage forms such as tablets will typically comprise one or more pharmaceutical excipients, which may for example help impart satisfactory processing and compression characteristics, or provide additional desirable physical characteristics to the tablet. Such pharmaceutical excipients may be selected from diluents, binders, glidants, lubricants, disintegrants, colors, flavors, sweetening agents, polymers, waxes or other solubility-retarding materials.

Compositions for intravenous administration will generally comprise intravenous fluids, i.e., sterile solutions of simple chemicals such as sugars, amino acids or electrolytes, which can be easily carried by the circulatory system and assimilated.

Dosage forms for parenteral administration will generally comprise fluids, particularly intravenous fluids, i.e., sterile solutions of simple chemicals such as sugars, amino acids or electrolytes, which can be easily carried by the circulatory system and assimilated. Such fluids are typically prepared with water for injection USP. Fluids used commonly for intravenous (IV) use are disclosed in Remington: The Science and Practice of Pharmacy, Lippincott Williams & Wilkins (2005). The pH of such IV fluids may vary, and will typically be from 3.5 to 8 as known in the art.

The chemical entities described herein may also be used in conjunction with other well known therapeutic agents that are selected for their particular usefulness against the condition that is being treated. For example, the chemical entities described herein may be useful in combination with at least one additional anti-cancer and/or cytotoxic agents. Further, the chemical entities described herein may also be useful in combination with other inhibitors of parts of the signaling pathway that links cell surface growth factor receptors to nuclear signals initiating cellular proliferation.

Such known anti-cancer and/or cytotoxic agents that may be used in combination with the chemical entities described herein include:

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumor antibiotics (for example anthracyclines like adriamycin, bleomycin, doxorubicin, daunomycin, epirubicin, idarubicin, mitomycinC, dactinomycin and mithramycin); antimitotic agents (for example vinca alkaloids like vincristine, vinblastine, vindesine and vinorelbine and taxoids like paclitaxel (Taxol™) and docetaxel (Taxotere™) and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5a-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4ylamino}thiazole-5-carboxamide (dasatinib, BMS-354825; J. Med. Chem., 2004, 47, 66586661) and bosutinib (SK1-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB 1 antibody cetuximab [Erbitux™, C225] and any growth factor or growth factor receptor antibodies disclosed by Stem et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3- ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (RI15777) and lonafarnib (SCH66336)), inhibitors of cell signalling through MEK and/or AKT kinases, c-kit inhibitors, abl kinase inhibitors, P13 kinase inhibitors, Plt3 kinase inhibitors, CSF-IR kinase inhibitors, IGF receptor (insulin like growth factor) kinase inhibitors; aurora kinase inhibitors (for example AZD1152, PH739358, VX-680, MLN8054, R763, MP235, MP529, VX-528 and AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib(ZD6474), vatalanib (PTK787), sunitinib (SU11248), axitinib (AG-013736), pazopanib (GW 786034) and 4·{4-fluoro-2-methylindol-5-yloxy)-6-methoxy-7-(3pyrrolidin-1-ylpropoxy) quinazoline (AZD2171; Example 240 within WO 00/47212), compounds such as those disclosed in International Patent Applications WO 97/22596, WO 97/30035, WO 97/32856 and WO 98/13354 and compounds that work by other mechanisms (for example linomide, inhibitors of integrin av~3 function and angiostatin));

(vi) vascular damaging agents such as Combrctastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotcntan (ZD4054) or atrascntan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase subject tolerance to chemotherapy or radiotherapy such as multi-drug resistance gene therapy; and (x) immunotherapy approaches, including for example ex-vivo and in-vivo approaches to increase the immunogenicity of subject's tumor cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumor cell lines and approaches using anti-idiotypic antibodies.

In certain embodiments, the at least one chemical entity is administered in combination with one or more agents chosen from pacliatxel, bortezomib, dacarbazine, gcmcitabinc, trastuzumab, bevacizumab, capecitabine, docetaxel, crlotinib, aromatase inhibitors, such as AROMASIN™ (exemestane), and estrogen receptor inhibitors, such as FASLODEX™ (fulvestrant).

When a chemical entity described herein is administered into a human subject, the daily dosage will normally be determined by the prescribing physician with the dosage generally varying according to the age, weight, and response of the individual subject, as well as the severity of the subject's symptoms.

In one exemplary application, a suitable amount of at least one chemical entity is administered to a mammal undergoing treatment for cancer, for example, breast cancer. Administration typically occurs in an amount of between about 0.01 mg/kg of body weight to about 100 mg/kg of body weight per day (administered in single or divided doses), such as at least about 0.1 mg/kg of body weight per day. A particular therapeutic dosage can include, e.g., from about 0.01 mg to about 1000 mg of the chemical entity, such as including, e.g., from about 1 mg to about 1000 mg. The quantity of the at least one chemical entity in a unit dose of preparation may be varied or adjusted from about 0.1 mg to 1000 mg, such as from about 1 mg to 300 mg, for example 10 mg to 200 mg, according to the particular application. The amount administered will vary depending on the particular $IC_{50}$ value of the at least one chemical entity used and the judgment of the attending clinician taking into consideration factors such as health, weight, and age. In combinational applications in which the at least one chemical entity described herein is not the sole active ingredient, it may be possible to administer lesser amounts of the at least one chemical entity and still have therapeutic or prophylactic effect.

In some embodiments, the pharmaceutical preparation is in unit dosage form. In such form, the preparation is subdivided into unit doses containing appropriate quantities of the active component, e.g., an effective amount to achieve the desired purpose.

The actual dosage employed may be varied depending upon the requirements of the subject and the severity of the condition being treated. Determination of the proper dosage for a particular situation is within the skill of the art. Generally, treatment is initiated with smaller dosages which are less than the optimum dose of the at least one chemical entity. Thereafter, the dosage is increased by small amounts until the optimum effect under the circumstances is reached. For convenience, the total daily dosage may be divided and administered in portions during the day if desired.

The amount and frequency of administration of the at least one chemical entities described herein, and if applicable other chemotherapeutic agents and/or radiation therapy, will be regulated according to the judgment of the attending clinician (physician) considering such factors as age, condition and size of the subject as well as severity of the disease being treated.

The chemotherapeutic agent and/or radiation therapy can be administered according to therapeutic protocols well known in the art. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent or radiation) on the subject, and in view of the observed responses of the disease to the administered therapeutic agents.

Also, in general, the at least one chemical entities described herein need not be administered in the same pharmaceutical composition as a chemotherapeutic agent, and may, because of different physical and chemical characteristics, be administered by a different route. For example, the chemical entities/compositions may be administered orally to generate and maintain good blood levels thereof, while the chemotherapeutic agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of chemical entity (and where appropriate, chemotherapeutic agent and/or radiation) will depend upon the diagnosis of the attending physicians and their judgment of the condition of the subject and the appropriate treatment protocol.

The chemical entities described herein (and where appropriate chemotherapeutic agent and/or radiation) may be administered concurrently (e.g., simultaneously, essentially simultaneously or within the same treatment protocol) or sequentially, depending upon the nature of the proliferative disease, the condition of the subject, and the actual choice of chemotherapeutic agent and/or radiation to be administered in conjunction (i.e., within a single treatment protocol) with the chemical entity/composition.

In combinational applications and uses, the chemical entity/composition and the chemotherapeutic agent and/or radiation need not be administered simultaneously or essentially simultaneously, and the initial order of administration of the chemical entity/composition, and the chemotherapeutic agent and/or radiation, may not be important. Thus, the at least one chemical entity described herein may be administered first followed by the administration of the chemotherapeutic agent and/or radiation; or the chemotherapeutic agent and/or radiation may be administered first followed by the administration of the at least one chemical entity described herein. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the subject. For example, the chemotherapeutic agent and/or radiation may be administered first, and then the treatment continued with the administration of the at least one chemical entity described herein followed, where determined advantageous, by the administration of the chemotherapeutic agent and/or radiation, and so on until the treatment protocol is complete.

Thus, in accordance with experience and knowledge, the practicing physician can modify each protocol for the administration of a chemical entity/composition for treatment according to the individual subject's needs, as the treatment proceeds.

The attending clinician, in judging whether treatment is effective at the dosage administered, will consider the general well-being of the subject as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

EXAMPLES

The following examples serve to more fully describe the manner of using the invention. These examples are presented for illustrative purposes and should not serve to limit the true scope of the invention.

In carrying out the procedures of the methods described herein, it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

Examples 1 & 2

Preparation of 5-((3R,5R,8R,9S,10S,13R,14S,17R)-3-amino-14-hydroxy-10,13-dimethylhexadecahydro-1H-cyclopenta[a]phenanthren-17-yl)-2H-pyran-2-one (example 1) and 5-((3S,5R,8R,9S,10S,13R,14S,17R)-3-amino-14-hydroxy-10,13-dimethylhexadecahydro-1H-cyclopenta[a]phenanthren-17-yl)-2H-pyran-2-one (example 2)

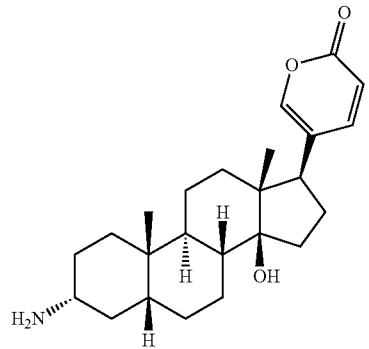

5-((3R,5R,8R,9S,10S,13R,14S,17R)-3-amino-14-hydroxy-10,13-dimethylhexadecahydro-1H-cyclopenta[a]phenanthren-17-yl)-2H-pyran-2-one

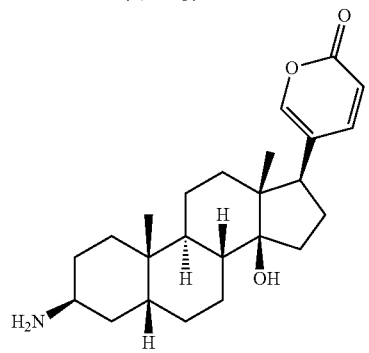

5-((3R,5R,8R,9S,10S,13R,14S,17R)-3-amino-14-hydroxy-10,13-dimethylhexadecahydro-1H-cyclopenta[a]phenanthren-17-yl)-2H-pyran-2-one

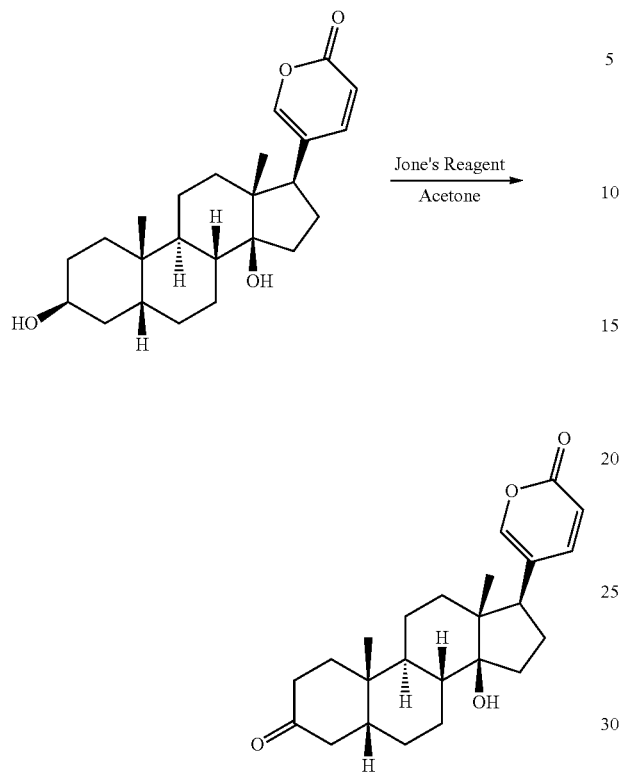

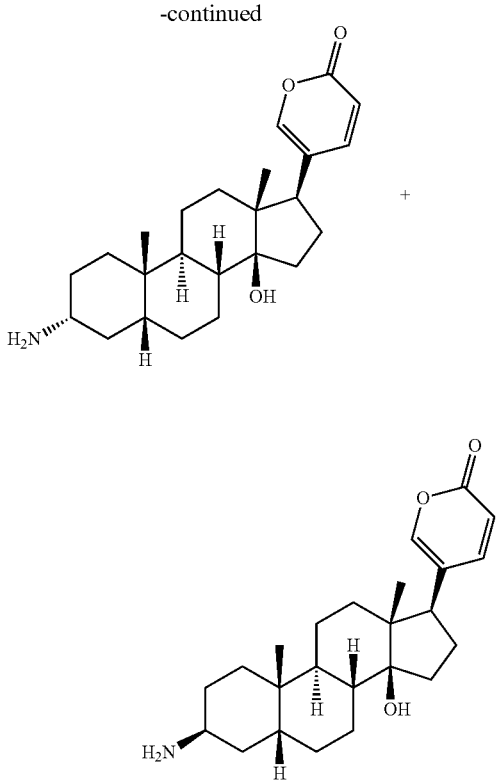

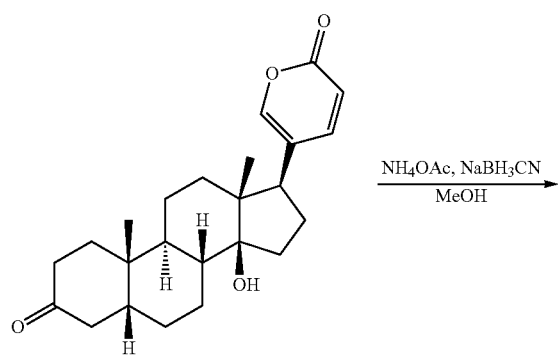

To a suspension of 5-((3S,5R,8R,9S,10S,13R,14S,17R)-3,14-dihydroxy-10,13-dimethylhexadecahydro-1H-cyclopenta[a]phenanthren-17-yl)-2H-pyran-2-one (5.25 g, 13.6 mmol, 1 eq.) in acetone (80 mL) at 0° C. was added Jone's Reagent (2.25 M, 6 mL, 1 eq.) dropwise. The resulting mixture was stirred at 0° C. for 3 h. To the mixture was added NaHSO$_3$ in small portions and the solution was extracted with DCM (3×50 mL). The combined organic phase was dried over anhydrous Na$_2$SO$_4$ and concentrated to afford 5-((5R,8R,9S,10S,13R,14S,17R)-14-hydroxy-10,13-dimethyl-3-oxohexadecahydro-1H-cyclopenta[a]phenanthren-17-yl)-2H-pyran-2-one (5.2 g, 98%).

To a suspension of 5-((5R,8R,9S,10S,13R,14S,17R)-14-hydroxy-10,13-dimethyl-3-oxohexadecahydro-1H-cyclopenta[a]phenanthren-17-yl)-2H-pyran-2-one (5.2 g, 13.6 mmol, 1 eq.) in MeOH (100 mL) was added AcONH$_4$ (11.6 g, 163.2 mmol, 12 eq.) followed by NaBH$_3$CN (1.71 g, 27.2 mmol 2 eq.). After being stirred at RT for 2 h, the mixture was added 1N HCl slowly to pH 2, then basified to pH 9 by the addition of Na$_2$CO$_3$. The mixture was extracted with DCM (3×50 mL). The combined organic layers were dried over anhydrous Na$_2$SO$_4$, concentrated and purified via prep-HPLC (10-40% CH$_3$CN in water with 0.1% TFA) to afford 5-((3R,5R,8R,9S,10S,13R,14S,17R)-3-amino-14-hydroxy-10,13-dimethylhexadecahydro-1H-cyclopenta[a]phenanthren-17-yl)-2H-pyran-2-one (R$_f$=3.9 min, 1.3 g, 50%) and 5-((3S,5R,8R,9S,10S,13R,14S,17R)-3-amino-14-hydroxy-10,13-dimethylhexadecahydro-1H-cyclopenta[a]phenanthren-17-yl)-2H-pyran-2-one (R$_f$=3.6 min, 710 mg, 27.2%). Analytical data for 5-((3R,5R,8R,9S,10S,13R,14S,17R)-3-amino-14-hydroxy-10,13-dimethylhexadecahydro-1H-cyclopenta[a]phenanthren-17-yl)-2H-pyran-2-one: LRMS (M+H$^+$) m/z calculated 386.3, found 386.2. $^1$H NMR (CD$_3$OD, 400 MHz) δ 7.99 (dd, 1 H), 7.43 (d, 1 H), 6.28 (d, 1 H), 3.71 (t, 1 H), 3.12-3.13 (m, 1 H), 2.54-2.58 (m, 1 H), 2.14-2.22 (m, 2 H), 1.12-1.96 (m, 21 H), 0.98 (s, 3 H), 0.71 (s, 3 H); Analytical data for 5-((3S,5R,8R,9S,10S,13R,14S,17R)-3-amino-14-hydroxy-10,13-dimethylhexadecahydro-1H-cyclopenta[a]phenanthren-17-yl)-2H-pyran-2-one: LRMS (M+H$^+$) m/z calculated 386.3, found 386.2. $^1$H NMR (CDCl$_3$, 400 MHz) δ 7.84 (dd, 1 H), 7.24 (d, 1 H), 6.26 (d, 1 H), 3.27 (s, 1 H), 2.46-2.48 (m, 1 H), 1.16-2.22 (m, 21 H), 0.98 (s, 3 H), 0.64 (s, 3 H).

Example 3

Preparation of 5-((5R,8R,9S,10S,13R,14S,17R)-14-hydroxy-10,13-dimethyl-3-(pyrrolidin-1-yl)hexadecahydro-1H-cyclopenta[a]phenanthren-17-yl)-2H-pyran-2-one

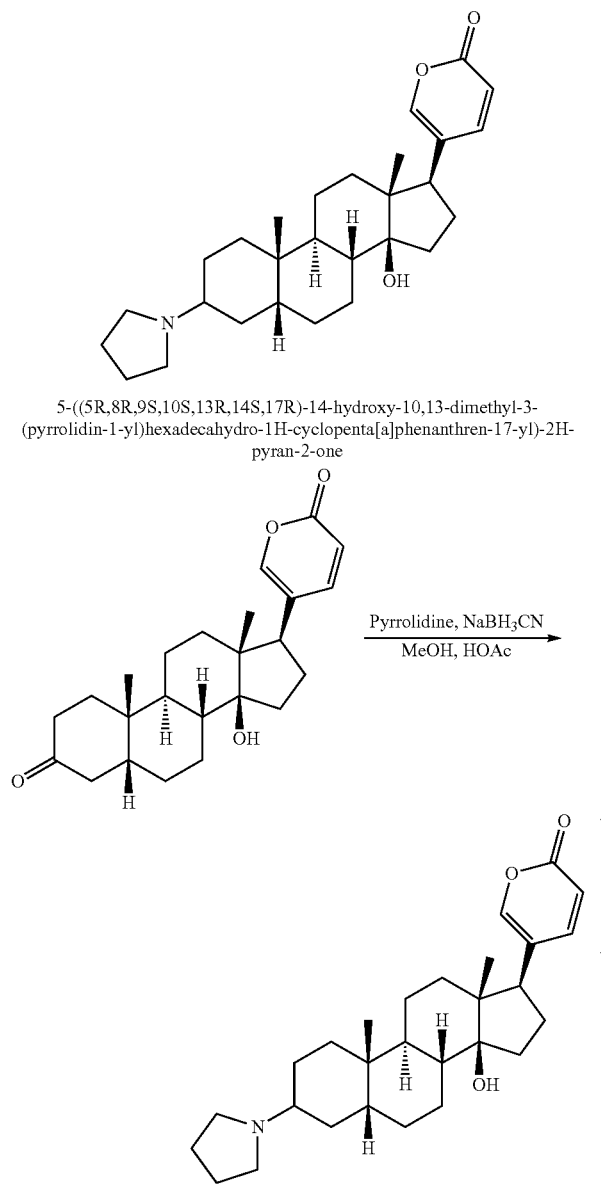

5-((5R,8R,9S,10S,13R,14S,17R)-14-hydroxy-10,13-dimethyl-3-(pyrrolidin-1-yl)hexadecahydro-1H-cyclopenta[a]phenanthren-17-yl)-2H-pyran-2-one To a suspension of 5-((5R,8R,9S,10S,13R,14S,17R)-14-hydroxy-10,13-dimethyl-3-oxohexadecahydro-1H-cyclopenta[a]phenanthren-17-yl)-2H-pyran-2-one (115 mg, 0.3 mmol, 1 eq.) in MeOH (10 mL) was slowly added prrolidine (420 mg, 6 mmol, 20 eq.), followed by NaBH$_3$CN (38 mg, 0.6 mmol, 2 eq.). The reaction mixture was adjusted to pH 6 by the addition of HOAc (2 mL). After being stirred for 1 h at RT, the mixture was concentrated, basified to pH 9 by the addition of sat. Na$_2$CO$_3$ solution. The mixture was extracted with DCM (3×50 mL). The combined organic layers were dried over anhydrous Na$_2$SO$_4$, concentrated and recrystalized from ethyl acetate to afford 5-((5R,8R,9S,10S,13R,14S,17R)-14-hydroxy-10,13-dimethyl-3-(pyrrolidin-1-yl)hexadecahydro-1H-cyclopenta[a]phenanthren-17-yl)-2H-pyran-2-one (69.5 mg, 52.6%). LRMS (M+H$^+$) m/z calculated 440.3, found 440.4. $^1$H NMR (CDCl$_3$, 400 MHz) δ 7.82-7.85 (m, 1 H), 7.22 (d, 1 H), 6.26 (d, 1 H), 2.44-2.70 (m, 5 H), 2.10-2.19 (m, 3 H), 1.55-2.05 (m, 12 H), 1.04-1.52 (m, 12 H), 0.92 (d, 3 H), 0.68 (d, 3 H).

Example 4

Preparation of 5-((5R,8R,9S,10S,13R,14S,17R)-14-hydroxy-10,13-dimethyl-3-(piperazin-1-yl)hexadecahydro-1H-cyclopenta[a]phenanthren-17-yl)-2H-pyran-2-one

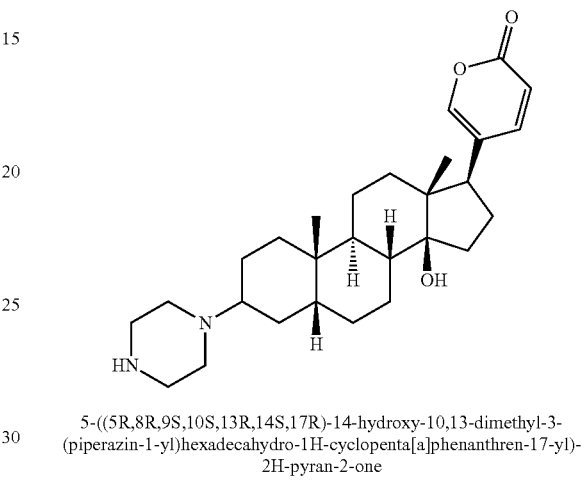

5-((5R,8R,9S,10S,13R,14S,17R)-14-hydroxy-10,13-dimethyl-3-(piperazin-1-yl)hexadecahydro-1H-cyclopenta[a]phenanthren-17-yl)-2H-pyran-2-one 5-((5R,8R,9S,10S,13R,14S,17R)-14-hydroxy-10,13-dimethyl-3-(piperazin-1-yl)hexadecahydro-1H-cyclopenta[a]phenanthren-17-yl)-2H-pyran-2-one (7.9 mg) was prepared as described for 5-((5R,8R,9S,10S,13R,14S,17R)-14-hydroxy-10,13-dimethyl-3-(pyrrolidin-1-yl)hexadecahydro-1H-cyclopenta[a]phenanthren-17-yl)-2H-pyran-2-one. LRMS (M+Fr) m/z calculated 455.3, found 455.4. $^1$H NMR (CDCl$_3$, 400 MHz) δ 7.84-7.87 (m, 1 H), 7.23 (d, 1 H), 6.26 (d, 1.H), 2.85-2.89 (m, 4 H), 2.08-2.47 (m, 8 H), 1.66-1.82 (m, 13 H), 1.04-1.52 (m, 12 H), 0.92 (s, 3 H), 0.70 (s, 3 H).

Example 5

Preparation of 5-((5R,8R,9S,10S,13R,14S,17R)-14-hydroxy-10,13-dimethyl-3-((2-(pyrrolidin-1-yl)ethyl)amino)hexadecahydro-1H-cyclopenta[a]phenanthren-17-yl)-2H-pyran-2-one

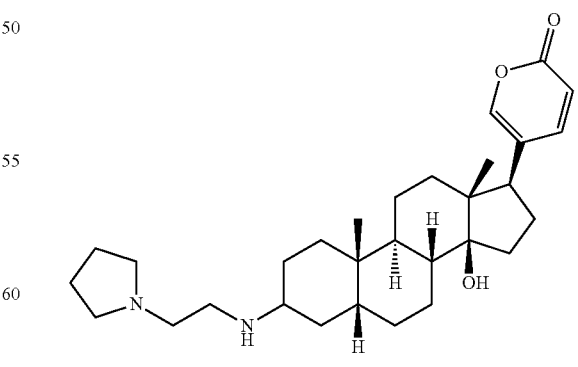

5-((5R,8R,9S,10S,13R,14S,17R)-14-hydroxy-10,13-dimethyl-3-((2-(pyrrolidin-1-yl)ethyl)amino)hexadecahydro-1H-cyclopenta[a]phenanthren-17-yl)-2H-pyran-2-one 5-((5R,8R,9S,10S,13R,14S,17R)-14-hydroxy-10,13-dimethyl-3-((2-(pyrrolidin-1-yl)ethyl)amino)hexadecahydro-1H-cyclopenta[a]phenanthren-17-yl)-2H-pyran-2-one (33 mg) was prepared as described for 5-((5R,8R,9S,10S,13R,14S,17R)-14-hydroxy-10,13-dimethyl-3-(pyrrolidin-1-yl)hexadecahydro-1H-cyclopenta[a]phenanthren-17-yl)-2H-pyran-2-one. LRMS (M+H$^+$) m/z calculated 483.4, found 483.4. $^1$H NMR (CDCl$_3$, 400 MHz) δ 7.82-7.85 (m, 1 H), 7.22 (d, 1 H), 6.26 (d, 1 H), 2.70 (t, 2 H), 2.60 (t, 2 H), 2.50 (m, 6 H), 2.05-2.15 (m, 3 H), 1.77-1.86 (m, 9 H), 1.17-1.54 (m, 15 H), 0.92 (d, 3 H), 0.70 (d, 3 H).

Example 6

Preparation of 5-((5R,8R,9S,10S,13R,14S,17R)-14-hydroxy-10,13-dimethyl-3-morpholinohexadecahydro-1H-cyclopenta[a]phenanthren-17-yl)-2H-pyran-2-one

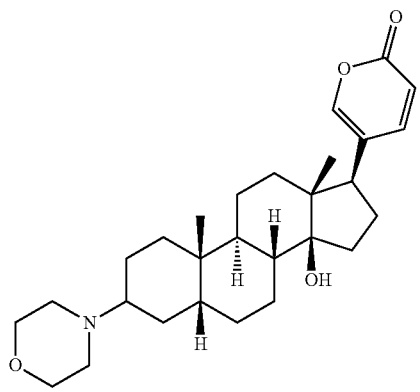

5-((5R,8R,9S,10S,13R,14S,17R)-14-hydroxy-10,13-dimethyl-3-morpholinohexadecahydro-1H-cyclopenta[a]phenanthren-17-yl)-2H-pyran-2-one 5-((5R,8R,9S,10S,13R,14S,17R)-14-hydroxy-10,13-dimethyl-3-morpholinohexadecahydro-1H-cyclopenta[a]phenanthren-17-yl)-2H-pyran-2-one (45.9 mg) was prepared as described for 5-((5R,8R,9S,10S,13R,14S,17R)-14-hydroxy-10,13-dimethyl-3-(pyrrolidin-1-yl)hexadecahydro-1H-cyclopenta[a]phenanthren-17-yl)-2H-pyran-2-one. LRMS (M+H$^+$) m/z calculated 456.3, found 456.4. $^1$H NMR (CDCl$_3$, 400 MHz) δ 7.82-7.85 (m, 1 H), 7.24 (d, 1 H), 6.26 (d, 1 H), 3.98-4.02 (m, 4 H), 3.68 (t, 2 H), 2.82 (d, 6 H), 2.47 (t, 1 H), 1.87-2.14 (m, 6 H), 1.40-1.61 (m, 14 H), 0.92 (d, 3 H), 0.70 (d, 3 H).

Example 7

Preparation of 5-((5R,8R,9S,10S,13R,14S,17R)-14-hydroxy-10,13-dimethyl-3-((2-morpholinoethyl)amino)hexadecahydro-1H-cyclopenta[a]phenanthren-17-yl)-2H-pyran-2-one

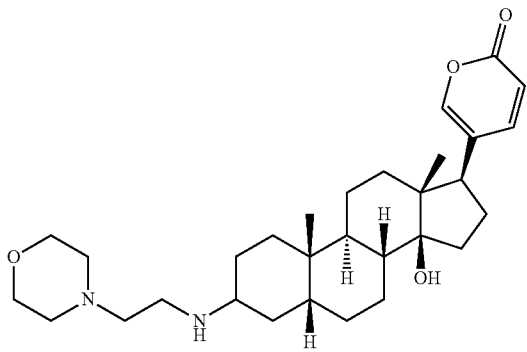

5-((5R,8R,9S,10S,13R,14S,17R)-14-hydroxy-10,13-dimethyl-3-((2-morpholinoethyl)amino)hexadecahydro-1H-cyclopenta[a]phenanthren-17-yl)-2H-pyran-2-one 5-((5R,8R,9S,10S,13R,14S,17R)-14-hydroxy-10,13-dimethyl-3-((2-morpholinoethyl)amino)hexadecahydro-1H-cyclopenta[a]phenanthren-17-yl)-2H-pyran-2-one (96 mg) was prepared as described for 5-((5R,8R,9S,10S,13R,14S,17R)-14-hydroxy-10,13-dimethyl-3-(pyrrolidin-1-yl)hexadecahydro-1H-cyclopenta[a]phenanthren-17-yl)-2H-pyran-2-one. LRMS (M+H$^+$) m/z calculated 499.3, found 499.4. $^1$H NMR (CDCl$_3$, 400 MHz) δ 7.82-7.85 (m, 1 H), 7.22 (d, 1 H), 6.26 (d, 1 H), 3.71 (t, 4 H), 2.73 (t, 2 H), 2.46-2.52 (m, 7 H), 2.05-2.15 (m, 2 H), 1.67-1.86 (m, 6 H), 1.16-1.59 (m, 16 H), 0.92 (d, 3 H), 0.70 (d, 3 H).

Example 8

Preparation of 4-((5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)piperazin-2-one

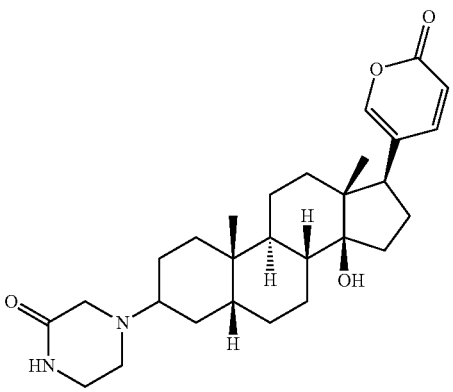

4-((5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)piperazin-2-one 4-((5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)piperazin-2-one (115 mg) was prepared as described for 5-((5R,8R,9S,10S,13R,14S,17R)-14-hydroxy-10,13-dimethyl-3-(pyrrolidin-1-yl)hexadecahydro-1H-cyclopenta[a]phenanthren-17-yl)-2H-pyran-2-one. LRMS (MAI) m/z calculated 469.3, found 469.4. $^1$H NMR (CDCl$_3$, 400 MHz) δ 7.82-7.88 (m, 1 H), 7.23 (d, 1 H), 6.26 (d, 1 H), 5.84-5.89 (m, 1 H), 3.29-3.38 (m, 3 H), 2.77-2.79 (m, 1 H), 2.45-2.47 (m, 1 H), 2.04-2.19 (m, 3 H), 1.66-1.89 (m, 9 H), 1.04-1.60 (m, 14H), 0.92 (d, 3 H), 0.70 (d, 3 H).

Example 9

Preparation of 5-((5R,8R,9S,10S,13R,14S,17R)-14-hydroxy-3-((2-hydroxyethyl)(methyl)amino)-10,13-dimethylhexadecahydro-1H-cyclopenta[a]phenanthren-17-yl)-2H-pyran-2-one

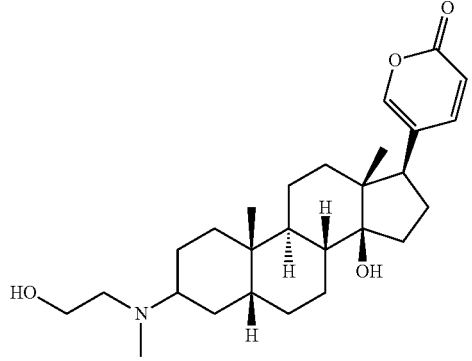

5-((5R,8R,9S,10S,13R,14S,17R)-14-hydroxy-3-((2-hydroxyethyl)(methyl)amino)-10,13-dimethylhexadecahydro-1H-cyclopenta[a]phenanthren-17-yl)-2H-pyran-2-one 5-((5R,8R,9S,10S,13R,14S,17R)-14-hydroxy-3-((2-hydroxyethyl)(methyl) amino)-10,13-dimethylhexadecahydro-1H-cyclopenta[a]phenanthren-17-yl)-2H-pyran-2-one (15.4 mg) was prepared as described for 5-((5R,8R,9S,10S,13R,14S,17R)-14-hydroxy-10,13-dimethyl-3-(pyrrolidin-1-yl)hexadecahydro-1H-cyclopenta[a]phenanthren-17-yl)-2H-pyran-2-one. LRMS (M+1-1) m/z calculated 444.3, found 444.4. $^1$H NMR (CDCl$_3$, 400 MHz) δ 7.83 (dd, 1 H), 7.23 (s, 1 H), 6.26 (d, 1 H), 3.55-3.60 (m, 2 H), 2.60-2.63 (m, 1 H), 2.44-2.48 (m, 3 H), 2.29-2.19 (m, 4 H), 2.06-2.18 (m, 1 H), 1.66-1.86 (m, 5 H), 1.71-1.55 (m, 16 H), 0.91-0.92 (m, 3 H), 0.70 (s, 3 H).

Example 10

Preparation of N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)piperazine-1-carboxamide

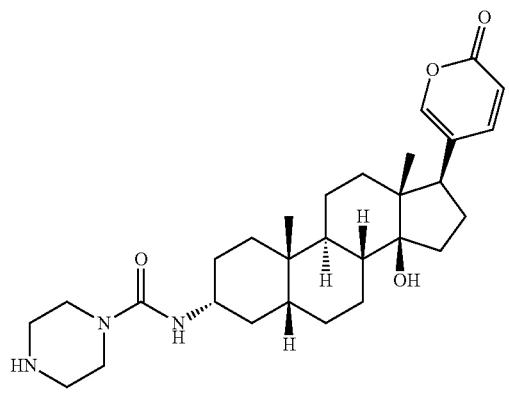

N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)piperazine-1-carboxamide

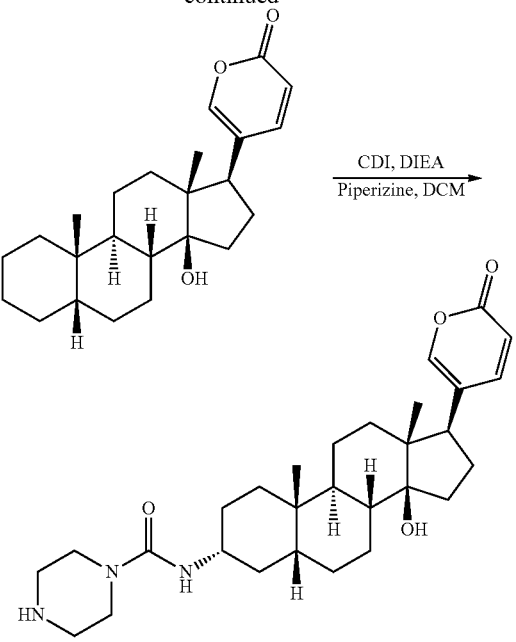

To a solution of CDI (50 mg, 0.31 mmol, 4 eq.) and DIEA (24 mg, 0.19 mmol, 2.4 eq.) in DCM (2 mL) was added 5-((3R,5R,8R,9S,10S,13R,14S,17R)-3-amino-14-hydroxy-10,13-dimethylhexadecahydro-1H-cyclopenta[a]phenanthren-17-yl)-2H-pyran-2-one (30 mg, 0.078 mmol, 1 eq.) and the resulting mixture was stirred at RT for 1 h. Then the mixture was added piperizine (376 mg, 3.9 mmol, 50 eq.) and the resulting mixture was stirred at RT overnight. The solid was removed by filtration and the filtrate was purified by prep-HPLC to afford N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)piperazine-1-carboxamide (13.8 mg, 35%). LRMS (M+H$^+$) m/z calculated 498.3, found 498.3. $^1$H NMR (CDCl$_3$, 400 MHz) δ 7.81-7.84 (dd, 1 H), 7.22-7.23 (s, 1 H), 6.25-6.27 (d, 1 H), 4.24-4.26 (d, 1 H), 3.67-3.68 (m, 1 H), 3.31-3.34 (m, 4 H), 2.85-2.88 (m, 4 H), 2.44-2.48 (m, 1 H), 2.04-2.20 (m, 2 H), 1.10-1.88 (m, 20 H), 0.92 (s, 3 H), 0.70 (s, 3H).

Example 11

Preparation of N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)piperazine-1-carboxamide

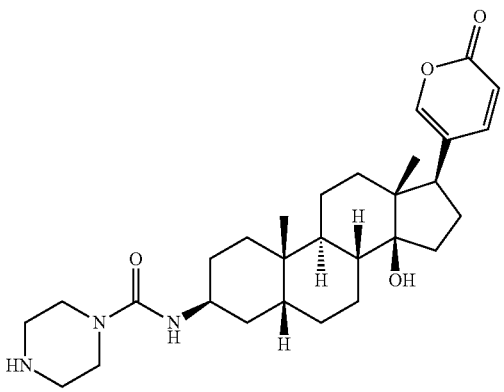

N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)piperazine-1-carboxamide N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)piperazine-1-carboxamidee (30.6 mg) was prepared as described for N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)piperazine-1-carboxamide. LRMS (M+H$^+$) m/z calculated 498.3, found 498.3. $^1$H NMR (CDCl$_3$, 400 MHz) δ 7.82-7.85 (dd, 1 H), 7.22-7.23 (s, 1 H), 6.25-6.27 (d, 1 H), 4.63-4.64 (d, 1 H), 4.13 (m, 1 H), 3.31-3.34 (m, 4 H), 2.86-2.88 (m, 4 H), 2.45-2.49 (m, 1 H), 1.08-2.22 (m, 22 H), 0.96 (s, 3 H), 0.70 (s, 3 H).

Example 12

Preparation of N-((5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)piperazine-1-carboxamide

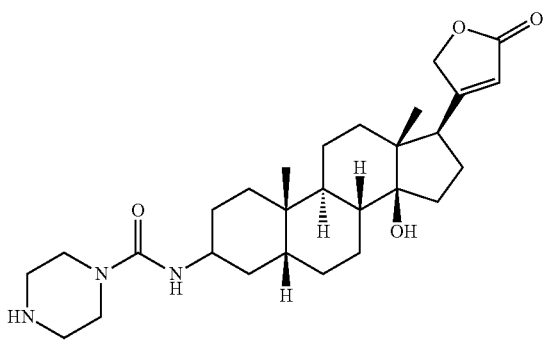

N-((5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)piperazine-1-carboxamide N-((5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)piperazine-1-carboxamide (16.6 mg) was prepared as described for N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)piperazine-1-carboxamide. LRMS (M+H$^+$) m/z calculated 486.3, found 486.4. $^1$H NMR (CD$_3$OD, 400 MHz) δ 5.93 (s, 1 H), 5.04-5.09 (m, 1 H), 4.96-4.97 (m, 1 H), 3.58-3.99 (m, 1 H), 3.33-3.41 (m, 4 H), 2.80-2.88 (m, 5 H), 2.19-2.27 (m, 2 H), 1.12-2.10 (m, 20 H), 0.99-1.01 (m, 3 H), 0.91 (s, 3 H).

Example 13

Preparation of N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)pyrrolidine-1-carboxamide

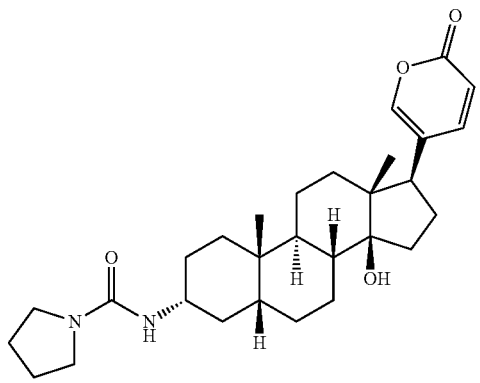

N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)pyrrolidine-1-carboxamide N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)pyrrolidine-1-carboxamide (10.6 mg) was prepared as described for N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)piperazine-1-carboxamide. LRMS (M+H$^+$) m/z calculated 483.3.3, found 483.3. $^1$H NMR (CDCl$_3$, 400 MHz) δ 7.82-7.85 (dd, 1 H), 7.22-7.23 (s, 1 H), 6.25-6.27 (d, 1 H), 3.99-4.01 (m, 1 H), 3.68 (m, 1 H), 3.30-3.33 (m, 4 H), 2.44-2.48 (m, 1 H), 1.10-2.20 (m, 27 H), 0.96 (s, 3 H), 0.70 (s, 3 H).

Example 14

Preparation of N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)pyrrolidine-1-carboxamide

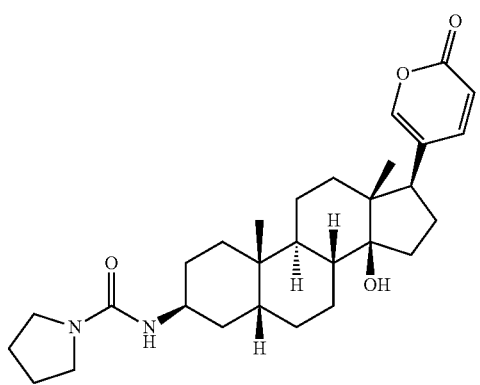

N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)pyrrolidine-1-carboxamide N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)pyrrolidine-1-carboxamide (3.5 mg) was prepared as described for N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)piperazine-1-carboxamide. LRMS (M+H⁺) m/z calculated 483.3, found 483.3. $^1$H NMR (CDCl$_3$, 400 MHz) δ 7.81-7.84 (dd, 1 H), 7.22-7.23 (s, 1 H), 6.25-6.27 (d, 1 H), 4.63-4.65 (d, 1 H), 4.13 (m, 1 H), 3.70-3.72 (m, 4 H), 3.32-3.34 (m, 4 H), 2.45-2.49 (m, 1 H), 1.07-2.22 (m, 22 H), 0.87 (s, 3 H), 0.70 (s, 3 H).

Example 15

Preparation of 1-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-(2-hydroxyethyl)urea

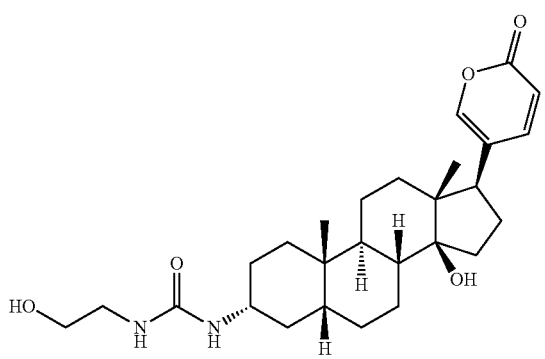

1-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-(2-hydroxyethyl)urea 1-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-(2-hydroxyethyl)urea (12.1 mg) was prepared as described for N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)piperazine-1-carboxamide. LRMS (M+H⁺) m/z calculated 473.3, found 473.3. $^1$H NMR (DMSO-d6, 300 MHz) δ 7.91-7.95 (dd, 1 H), 7.52 (s, 1 H), 6.29 (d, 1 H), 5.84 (d, 1 H), 5.65-5.96 (t, 1 H), 4.61-4.65 (t, 1 H), 4.16 (s, 1 H), 3.31-3.38 (q, 3 H), 3.01-3.06 (q, 2 H), 1.11-1.78 (m, 20 H), 0.86 (s, 3 H), 0.60 (s, 3H).

Example 16

Preparation of 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-(2-hydroxyethyl)urea

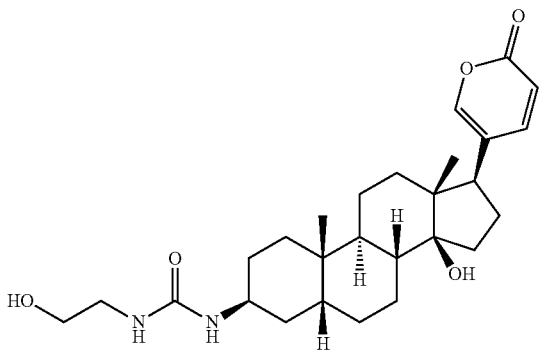

1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-(2-hydroxyethyl)urea 1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-(2-hydroxyethyl)urea (21.8 mg) was prepared as described for N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)piperazine-1-carboxamide. LRMS (M+H⁺) m/z calculated 473.3, found 473.2. $^1$H NMR (DMSO-d6, 400 MHz) δ 7.91-7.95 (dd, 1 H), 7.52 (d, 1 H), 6.28 (d, 1 H), 6.18 (d, 1 H), 5.82 (brs, 1 H), 4.09-4.17 (m, 1 H), 3.81-3.85 (m, 1 H), 3.35-3.38 (t, 2 H), 3.01-3.05 (m, 2 H), 2.43-2.51 (m, 2 H), 1.11-2.08 (m, 20 H), 0.89 (s, 3 H), 0.60 (s, 3H).

Example 17

Preparation of 1-(2-amino ethyl)-3-((3R,5R,8R,9S,10S,13R,14S,17R)-14-hydroxy-10,13-dimethyl-17-(2-oxo-2H-pyran-5-yl)hexa decahydro-1H-cyclopenta[a]phenanthren-3-yl)urea

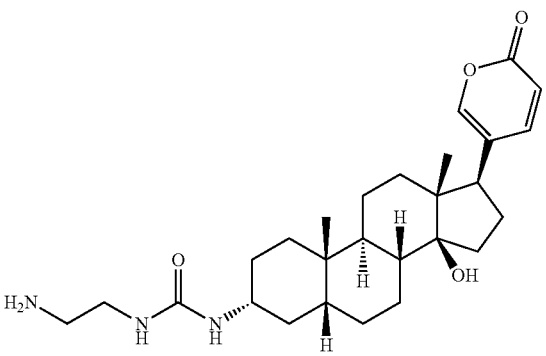

1-(2-aminoethyl)-3-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)urea 1-(2-Aminoethyl)-3-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)urea (14.8 mg) was prepared as described for N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)piperazine-1-carboxamide. LRMS (M+H$^+$) m/z calculated 472.3, found 472.3. $^1$H NMR (DMSO-d6, 300 MHz) δ 7.93 (d, 1 H), 7.53 (s, 1 H), 6.29 (d, 1 H), 5.68-5.78 (m, 2 H), 4.16 (s, 1 H), 2.91-2.98 (q, 2 H), 2.44-2.53 (m, 2 H), 1.96-2.07 (m, 2 H), 1.01-1.79 (m, 20 H), 0.86 (s, 3 H), 0.60 (s, 3H).

Example 18

Preparation of 1-(2-aminoethyl)-3-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)urea

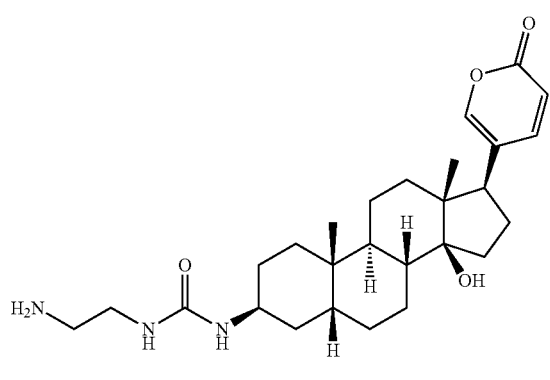

1-(2-aminoethyl)-3-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)urea 1-(2-Amino ethyl)-3-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)urea (10.9 mg) was prepared as described for N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)piperazine-1-carboxamide. LRMS (M+H$^+$) m/z calculated 472.3, found 472.1. $^1$H NMR (DMSO-d6, 300 MHz) δ 7.91-7.94 (dd, 1 H), 7.70 (brs, 1 H), 7.52 (s, 1 H), 6.27-6.33 (m, 2 H), 5.98-6.01 (t, 1 H), 4.14 (s, 1 H), 3.83-3.87 (m, 1H), 3.16-3.24 (q, 2 H), 2.80-2.84 (q, 2 H), 2.43-2.50 (m, 2 H), 1.05-2.08 (m, 22 H), 0.89 (s, 3 H), 0.60 (s, 3H).

Example 19

Preparation of 2-morpholinoethyl ((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)carbamate

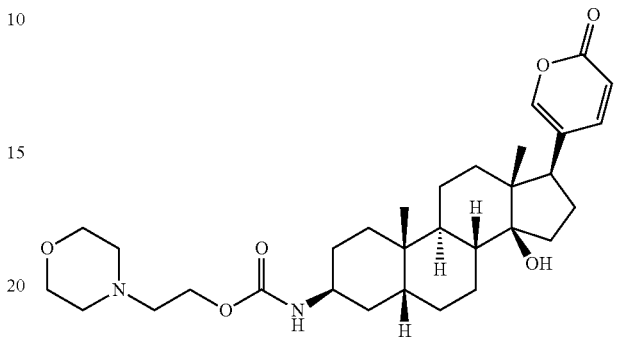

2-morpholinoethyl ((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)carbamate 2-Morpholinoethyl ((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)carbamate (25.8 mg) was prepared as described for N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)piperazine-1-carboxamide. LRMS (M+H$^+$) m/z calculated 543.3, found 543.4. $^1$H NMR (CD$_3$OD, 400 MHz) δ 7.89 (dd, 1 H), 7.33 (d, 1 H), 6.17-6.19 (d, 1 H), 4.07-4.08 (m, 2 H), 3.78 (m, 1 H), 3.59-3.61 (m, 4 H), 2.44-2.55 (m, 7H), 1.16-2.09 (m, 22 H), 0.88 (s, 3 H), 0.61 (s, 3H).

Example 20

Preparation of N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)morpholine-4-carboxamide

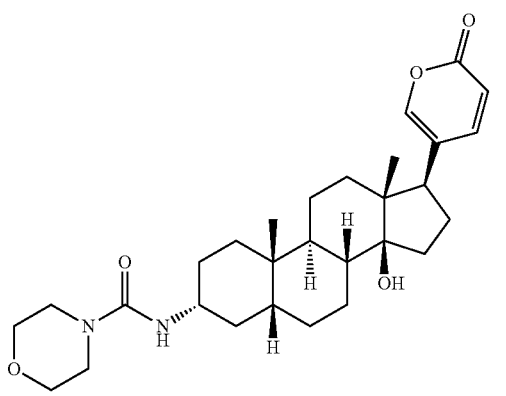

N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)morpholine-4-carboxamide

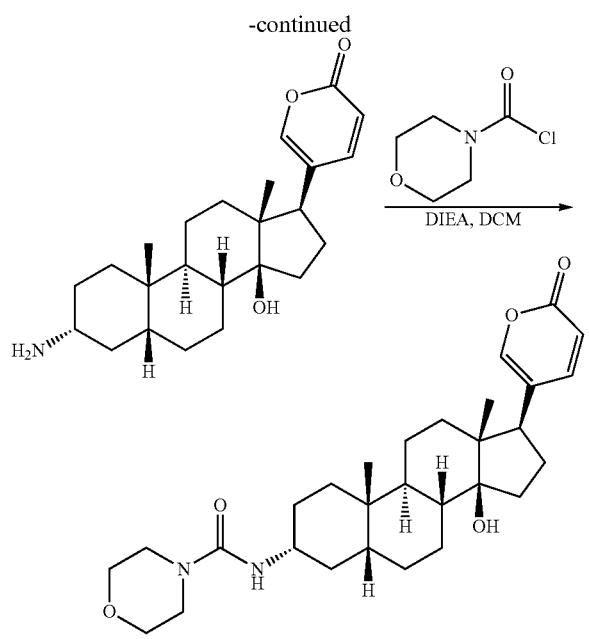

To a solution of 5-((3R,5R,8R,9S,10S,13R,14S,17R)-3-amino-14-hydroxy-10,13-dimethylhexadecahydro-1H-cyclopenta[a]phenanthren-17-yl)-2H-pyran-2-one (50 mg, 0.13 mmol, 1 eq.) in DCM (2 mL) was added DIEA (50 mg, 0.39 mmol, 3 eq.) followed by morpholine-4-carbonyl chloride (23 mg, 0.16 mmol, 1.2 eq.) and the resulting mixture was stirred at RT overnight. The reaction mixture was concentrated and purified via flash column chromatography to afford N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)morpholine-4-carboxamide (18.2 mg, 28% yield). LRMS (M+H$^+$) m/z calculated 499.3, found 499.3. $^1$H NMR (CDCl$_3$, 400 MHz) δ 7.83 (dd, 1 H), 7.22-7.23 (s, 1 H), 6.26 (d, 1 H), 4.25 (d, 1 H), 3.65-3.70 (m, 5 H), 3.32-3.34 (m, 4 H), 2.44-2.48 (m, 1 H), 2.02-2.22 (m, 2 H), 1.10-1.88 (m, 20 H), 0.87 (s, 3 H), 0.70 (s, 3 H).

Example 21

Preparation of N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)morpholine-4-carboxamide

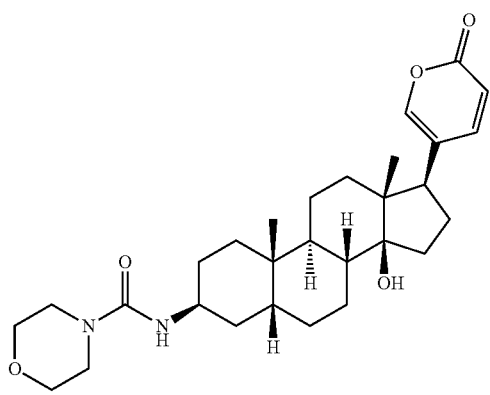

N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)morpholine-4-carboxamide N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)morpholine-4-carboxamide (18.8 mg) was prepared as described for N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)morpholine-4-carboxamide. LRMS (M+H$^+$) m/z calculated 499.3, found 499.3. $^1$H NMR (CDCl$_3$, 400 MHz) δ 7.81-7.84 (dd, 1 H), 7.22-7.23 (s, 1 H), 6.25-6.27 (d, 1 H), 4.63-4.65 (d, 1 H), 4.13 (m, 1 H), 3.70-3.72(m, 4 H), 3.32-3.34 (m, 4 H), 2.45-2.49 (m, 1 H), 1.07-2.22 (m, 22 H), 0.87 (s, 3 H), 0.70 (s, 3 H).

Example 22

Preparation of N-((5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)morpholine-4-carboxamide

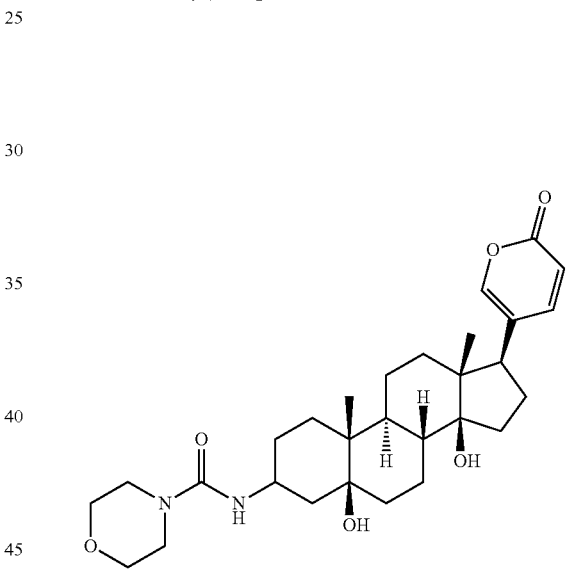

N-((5S,8R,9S,10R,13R,14S,17R)-5,14-hydroxy-10,13-dimethyl-17-(2-oxo-2H-pyran-5-yl)hexadecahydro-1H-cyclopenta[a]phenanthren-3-yl)morpholine-4-carboxamide N-((5 S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)morpholine-4-carboxamide (9.1 mg) was prepared as described for N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)morpholine-4-carboxamide. LRMS (M+H$^+$) m/z calculated 515.3, found 515.3. $^1$H NMR (CDCl$_3$, 400 MHz) δ 7.81 (dd, 1 H), 7.24 (d, 1 H), 6.27 (d, 1 H), 4.17 (s, 1 H), 3.66-3.69 (t, 4H), 3.31 (t, 4 H), 2.47-2.51 (m, 1 H), 2.17-2.25 (m, 2H), 1.99-2.07 (m, 2H), 1.20-1.94 (m, 18 H), 0.91 (s, 3 H), 0.71 (s, 3H).

Example 23

Preparation of methyl ((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)carbamate

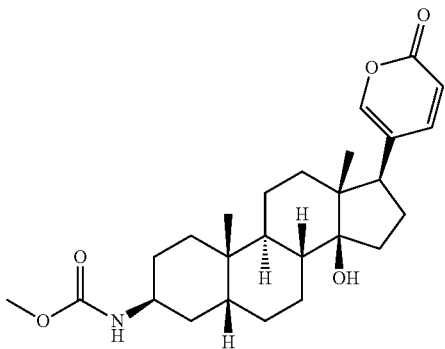

methyl ((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)carbamate Methyl ((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)carbamate (18.2 mg) was prepared as described for N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)morpholine-4-carboxamide. LRMS (M+H$^+$) m/z calculated 462.2, found 462.3. $^1$H NMR (CDCl$_3$, 400 MHz) δ 7.83 (dd, 1 H), 7.23 (d, 1 H), 6.26 (d, 1 H), 4.95 (d, 1 H), 3.94-3.97 (m, 1 H), 3.68 (s, 1 H), 2.24-2.49 (m, 1 H), 1.06-2.21 (m, 22 H), 0.94 (s, 3 H), 0.70 (s, 3H).

Example 24

Preparation of N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)methanesulfonamide

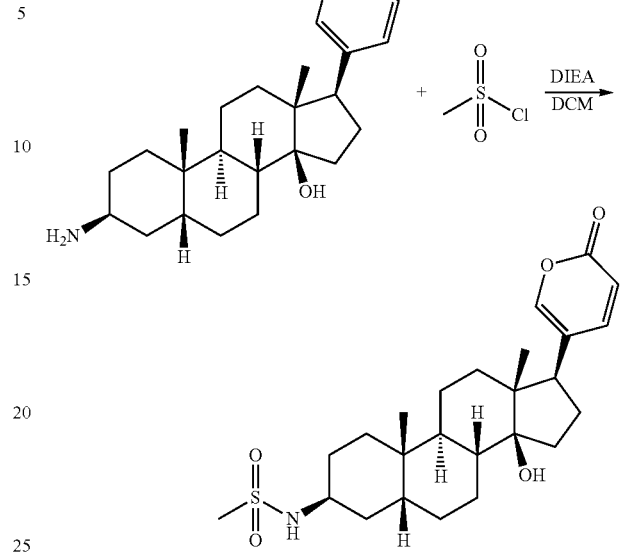

To a solution of 5-((3S,5R,8R,9S,10S,13R,14S,17R)-3-amino-14-hydroxy-10,13-dimethylhexadecahydro-1H-cyclopenta[a]phenanthren-17-yl)-2H-pyran-2-one (20 mg, 0.052 mmol, 1.0 eq.) in DCM (5 mL) was added DIEA (13.0 mg, 0.10 mmol, 2.0 eq.) at 0° C., followed by methanesulfonyl chloride (8.9 mg, 0.078 mmol, 1.5 eq.). After being stirred at RT for 1 h, the resulting mixture was evaporated and the residue was purified by flash chromatography (PE/EA=1:2, v/v) to afford N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)methanesulfonamide (13.0 mg, 54%). LRMS (M−H$^+$) m/z calculated 462.2, found 462.3. $^1$H NMR (CDCl$_3$, 400 MHz) δ 7.82 (dd, 1 H), 7.23 (d, 1 H), 6.27 (d, 1 H), 4.52 (d, 1 H), 3.79-3.85 (m, 1 H), 2.97 (s, 1 H), 2.44-2.49 (m, 1 H), 2.16-2.22 (m, 1 H), 1.87-2.06 (m, 3 H), 1.13-1.79 (m, 18 H), 0.96 (s, 3 H), 0.70 (s, 3H).

Example 25

Preparation of N-((5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N-methylmorpholine-4-carboxamide

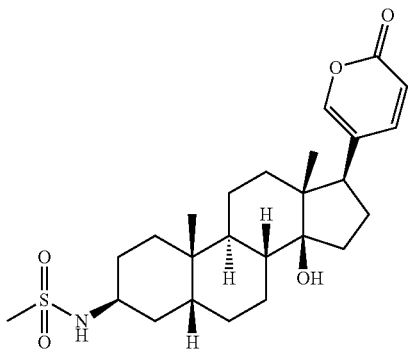

N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)methanesulfonamide

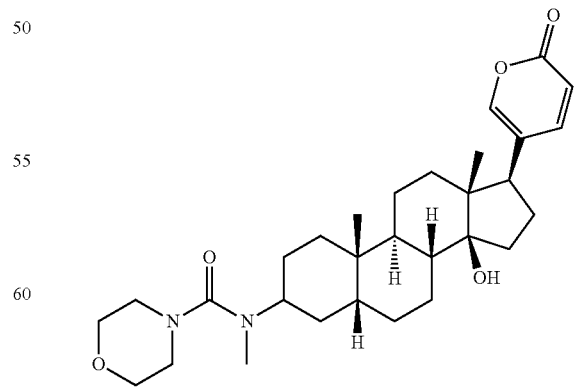

N-((5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N-methylmorpholine-4-carboxamide 113
-continued

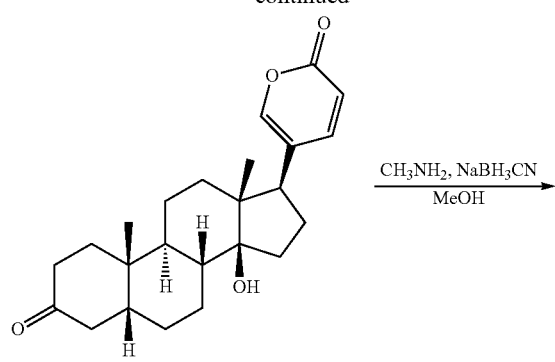

114
-continued

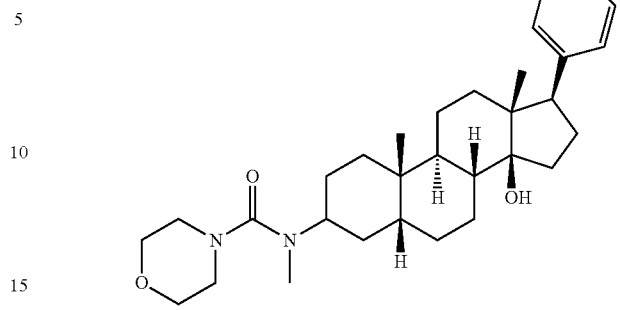

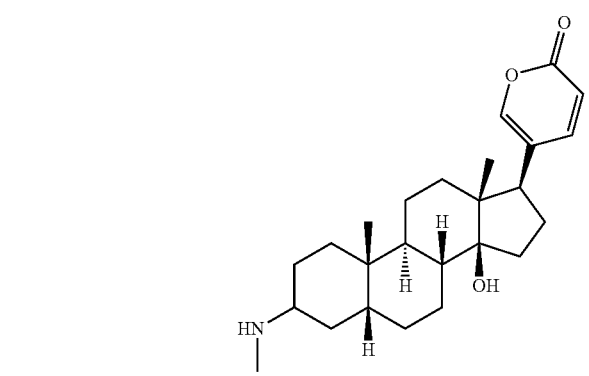

To a suspension of 5-((5R,8R,9S,10S,13R,14S,17R)-14-hydroxy-10,13-dimethyl-3-oxohexadecahydro-1H-cyclopenta[a]phenanthren-17-yl)-2H-pyran-2-one (1.0 g, 2.6 mmol, 1 eq.) in MeOH (50 mL) was added 30% MeNH2 solution in MeOH (968 mg, 31.2 mmol, 12 eq.), followed by NaBH$_3$CN (656 mg, 20.8 mmol 8 eq.). After being stifling at RT for 2 h, the mixture was basified to pH=9 by the addition of Na$_2$CO$_3$. The mixture was extracted with <50 mL). The combined organic layers were dried over anghydrous Na$_2$SO$_4$, and concentrated to afford crude 5-((5R,8R,9S,10S,13R,14S,17R)-14-hydroxy-10,13-dimethyl-3-(methylamino)hexadecahydro-1H-cyclopenta[a]phenanthren-17-yl)-2H-pyran-2-one (700 mg, 67%) which was used directly in the next step.

To a solution of 5-((5R,8R,9S,10S,13R,14S,17R)-14-hydroxy-10,13-dimethyl-3-(methylamino)hexadecahydro-1H-cyclopenta[a]phenanthren-17-yl)-2H-pyran-2-one (40 mg, 0.1 mmol, 1 eq.) in DCM (3 mL) was added DIEA (38.7 mg, 0.3 mmol, 3 eq.), followed by morpholine-4-carbonyl chloride (22.5 mg, 0.15 mmol, 1.5 eq.). The resulting mixture was stirred at RT overnight, then concentrated. The residue was purified via flash chromatography (PE/EA-1:2, v/v) to afford N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)morpholine-4-carboxamide (20.1 mg, 39%). LRMS (M+H$^+$) m/z calculated 513.3, found 513.3. $^1$H NMR (CDCl$_3$, 400 MHz) δ 7.84 (dd, 1 H), 7.23 (s, 1 H), 6.26 (d, 1 H), 3.66-3.70 (m, 5 H), 3.18-3.34 (m, 4 H), 2.76 (d, 3 H), 2.45-2.49 (m, 1 H), 2.18-2.22 (m, 1 H), 1.08-2.07 (m, 20 H), 0.93 (s, 3 H), 0.70 (s, 3 H).

Example 26

Preparation of methyl ((5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)(methyl)carbamate

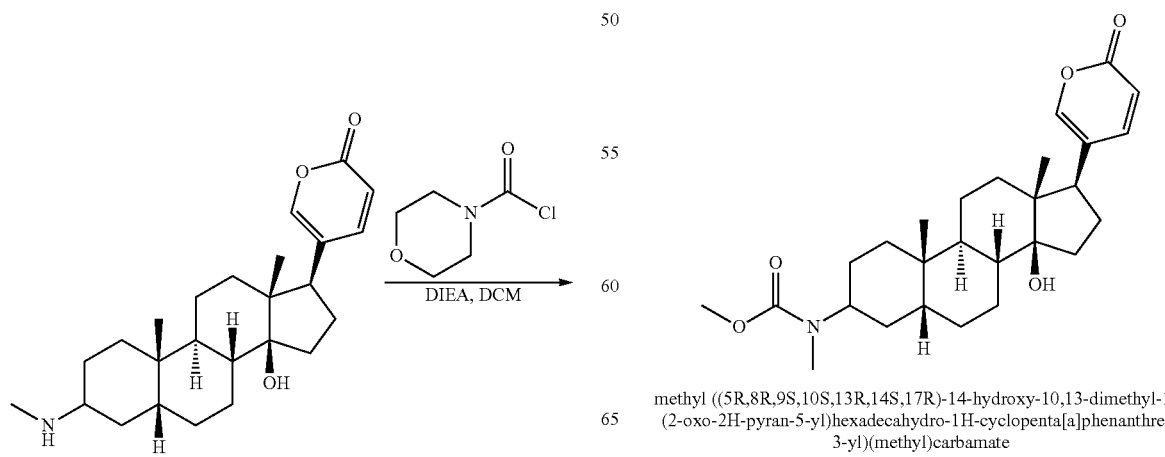

methyl ((5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)(methyl)carbamate

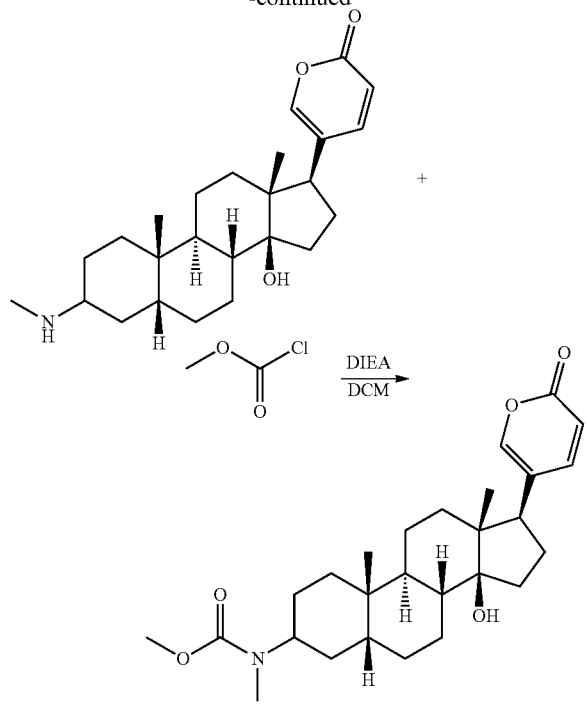

To a solution of 5-((5R,8R,9S,10S,13R,14S,17R)-14-hydroxy-10,13-dimethyl-3-(methylamino)hexadecahydro-1H-cyclopenta[a]phenanthren-17-yl)-2H-pyran-2-one (50 mg, 0.125 mmol, 1 eq.) and DIEA (48.3 mg, 0.375 mmol, 3 eq.) in DCM (100 mL) was added methyl carbonochloridate (17.6 mg, 0.18 mmol, 1.5 eq.). After being stirred at RT for 2 h, the mixture was washed with sat. $Na_2CO_3$ solution (20 mL) and extracted with DCM (3×20 mL). The combined orhanic layers were dried over anhydrous $Na_2SO_4$, and concentrated. The residue was purified by prep-HPLC to afford methyl ((5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)(methyl)carbamate (22.8 mg, 38.4%). LRMS (M+H$^+$) m/z calculated 458.3, found 458.3. $^1$H NMR (CDCl$_3$, 400 MHz) δ 7.86 (dd, 1 H), 7.24 (s, 1 H), 6.27 (d, 1 H), 3.95 (s, 1 H), 3.69-3.70 (m, 3 H), 2.81-2.95 (m, 5 H), 2.45-2.49 (m, 1 H), 1.05-2.23 (m, 21 H), 0.96 (s, 3 H), 0.71 (s, 3 H).

Example 27

Preparation of 2-amino-N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)acetamide

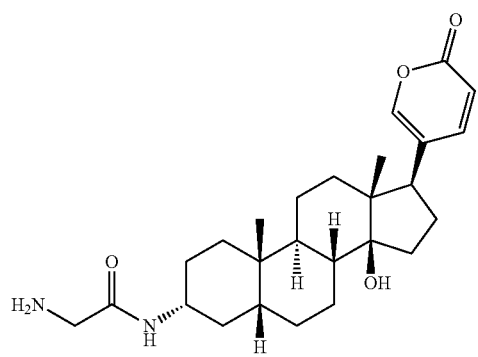

2-amino-N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)acetamide

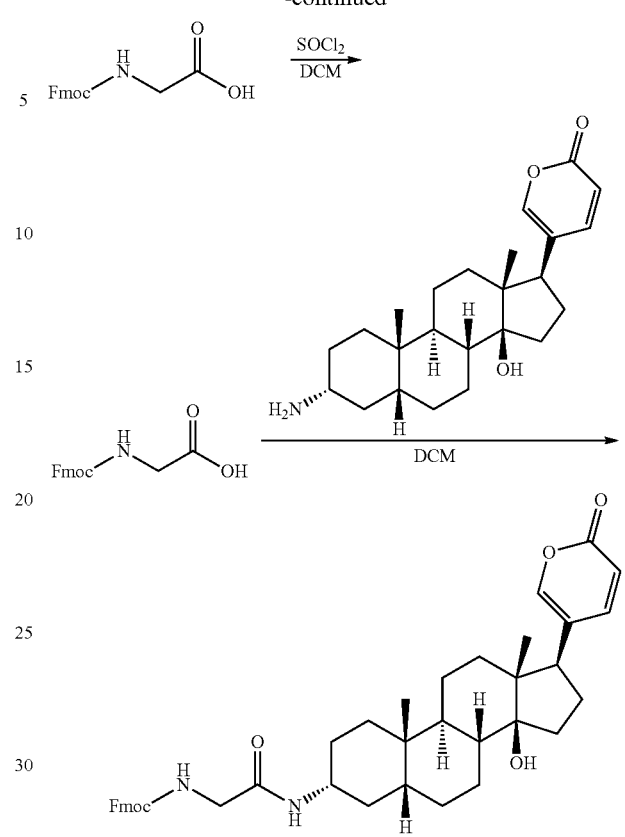

To a solution of 2-((((9H-fluoren-9-yl)methoxy)carbonyl)amino)acetic acid (11.6 mg, 0.039 mmol) in DCM (3 mL) was added SOCl$_2$ (46 mg, 0.39 mmol, 10 eq.). The resulting mixture was stirred under reflux for 3 h, then concentrated in vacuo. The residue was dissolved in DCM (3 mL) and was added to a mixture of 5-((3R,5R,8R,9S,10S,13R,14S,17R)-3-amino-14-hydroxy-10,13-dimethylhexadecahydro-1H-cyclopenta[a]phenanthren-17-yl)-2H-pyran-2-one (10 mg, 0.026 mmol, 0.66 eq.) in a mixture of DCM (3 mL) and saturated aqueous NaHCO$_3$ solution (3 mL). The resulting mixture was stirred at RT for 3 h and extracted with DCM (3×10 mL). The combined organic layers were dried over MgSO$_4$ and purified by prep-HPLC to afford (9H-fluoren-9-yl)methyl (2-(((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)amino)-2-oxoethyl)carbamate as a white solid (7.6 mg, 44%).

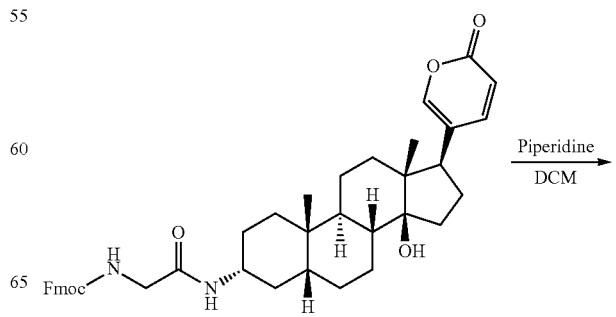

-continued

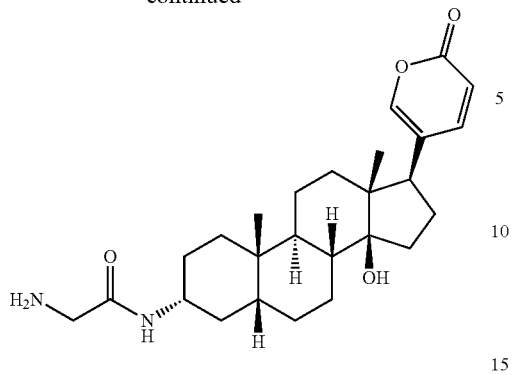

To a solution of (9H-fluoren-9-yl)methyl (2-(((3R,5R,8R, 9S,10S,13R,14S,17R)-14-hydroxy-10,13-dimethyl-17-(2-oxo-2H-pyran-5-yl)hexadecahydro-1H-cyclopenta[a]phenanthren-3-yl)amino)-2-oxoethyl)carbamate (45 mg, 0.068 mmol, 1 eq.) in DCM (3 mL) was added piperidine (5 drops) and the resulting mixture was stirred at RT overnight. The reaction mixture was concentrated and purified by prep-HPLC to afford 2-amino-N-((3R,5R,8R,9S,10S,13R, 14S,17R)-14-hydroxy-10,13-dimethyl-17-(2-oxo-2H-pyran-5-yl)hexadecahydro-1H-cyclopenta[a]phenanthren-3-yl)acetamide as a white solid (10.2 mg, 34%). LRMS (M+H$^+$) m/z calculated 443.3, found 443.2. $^1$H NMR (CD$_3$OD, 400 MHz) δ 7.99 (dd, 1 H), 7.43 (d, 1 H), 6.28 (d, 1 H), 3.67 (t, 1 H), 3.37 (s, 2 H), 2.54-2.57 (m, 1 H), 0.96-2.24 (m, 24 H), 0.91 (s, 3 H), 0.70 (s, 3 H).

Example 28

Preparation of 2-amino-N-((3S,5R,8R,9S,10S,13R, 14S,17R)-14-hydroxy-10,13-dimethyl-17-(2-oxo-2H-pyran-5-yl)hexadecahydro-1H-cyclopenta[a]phenanthren-3-yl)acetamide

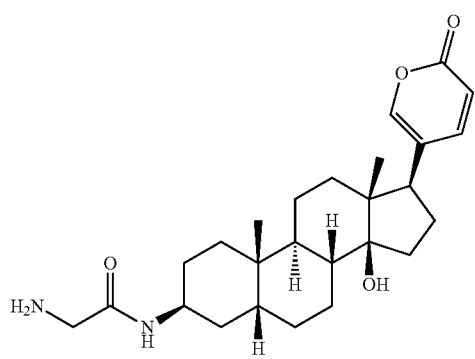

2-amino-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)acetamide 2-Amino-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)acetamide (20.6 mg) was prepared as described for 2-amino-N-((3R,5R,8R, 9S,10S,13R,14S,17R)-14-hydroxy-10,13-dimethyl-17-(2-oxo-2H-pyran-5-yl)hexadecahydro-1H-cyclopenta[a]phenanthren-3-yl)acetamide. LRMS (M+H$^+$) m/z calculated 443.3, found 443.3. $^1$H NMR (CD$_3$OD, 400 MHz) δ 7.99 (dd, 1 H), 7.43 (d, 1 H), 6.28 (d, 1 H), 4.16 (s, 1 H), 3.56 (s, 2 H), 2.54-2.58 (m, 1 H), 0.96-2.24 (m, 24 H), 0.90 (s, 3 H), 0.70 (s, 3 H).

Example 29

Preparation of (R)-2-amino-N-((3S,5R,8R,9S,10S, 13R,14S,17R)-14-hydroxy-10,13-dimethyl-17-(2-oxo-2H-pyran-5-yl)hexadecahydro-1H-cyclopenta[a]phenanthren-3-yl)-3-methylbutanamide

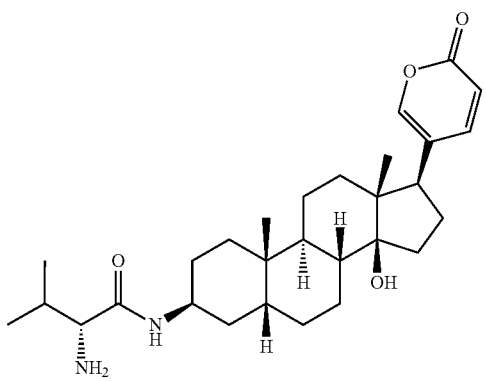

(R)-2-amino-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-methylbutanamide (R)-2-amino-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-3-methylbutanamide (11.5 mg) was prepared as described for 2-amino-N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)acetamide. LRMS (M+H$^+$) m/z calculated 485.3, found 485.4. $^1$H NMR (CD$_3$OD, 400 MHz) δ 7.94 (dd, 1 H), 7.38 (d, 1 H), 6.23 (d, 1 H), 4.06 (m, 1 H), 3.12 (d, 1 H), 2.51 (m, 1 H), 1.20-2.10 (m, 22H), 0.86-0.94 (m, 29 H), 0.66 (s, 3 H).

Example 30

Preparation of (2R)-2-amino-N-((5 S,8R,9S,10R, 13R,14S,17R)-5,14-dihydroxy-10,13-dimethyl-17-(2-oxo-2H-pyran-5-yl)hexadecahydro-1H-cyclopenta[a]phenanthren-3-yl)-3-methylbutanamide

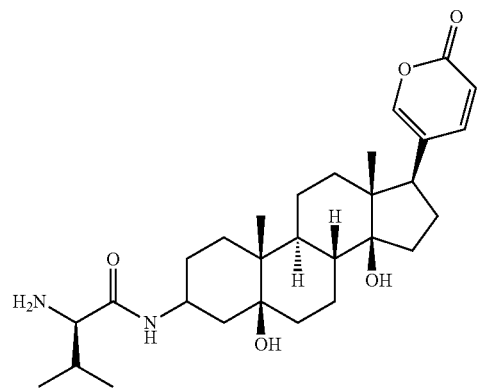

(2R)-2-amino-N-((5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)-3-methylbutanamide (2R)-2-amino-N-((5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)-3-methylbutanamide (9.3 mg) was prepared as described for 2-amino-N-((3R,5R,8R,9S,10S,13R,14S,17R)-14-hydroxy-10,13-dim ethyl-17-(2-oxo-2H-pyran-5-yl)hexadecahydro-1H-cyclopenta[a]phenanthren-3-yl)acetamide. LRMS (M+H$^+$) m/z calculated 501.3, found 501.4. $^1$H NMR (CDCl$_3$, 400 MHz) δ 8.24 (d, 1H), 7.82 (dd, 1 H), 7.24 (d, 1 H), 6.27 (d, 1 H), 4.28 (s, 1 H), 3.14 (brs, 1H), 2.31-2.51 (m, 1 H), 1.90-2.29 (m, 7 H), 1.20-1.87 (m, 18 H), 0.97 (d, 3H), 0.92 (s, 3 H), 0.89 (d, 3H), 0.71 (s, 3H).

Example 31

Preparation of (R)-2-amino-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)propanamide

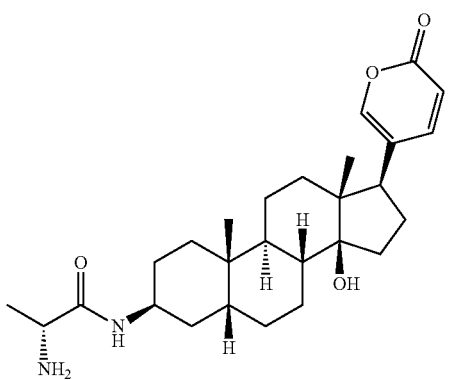

(R)-2-amino-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)propanamide (R)-2-amino-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)propanamide (12.9 mg) was prepared as described for 2-amino-N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)acetamide. LRMS (M+H$^+$) m/z calculated 457.3, found 457.4. $^1$H NMR (CD$_3$OD, 400 MHz) δ 7.89 (dd, 1 H), 7.34 (d, 1 H), 6.18 (d, 1 H), 3.98 (s, 1 H), 3.38 (q, 1 H), 2.41-2.51 (m, 1 H), 1.15-2.18 (m, 24H), 0.89 (s, 3 H), 0.61 (s, 3 H).

Example 32

Preparation of (S)—N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)pyrrolidine-2-carboxamide

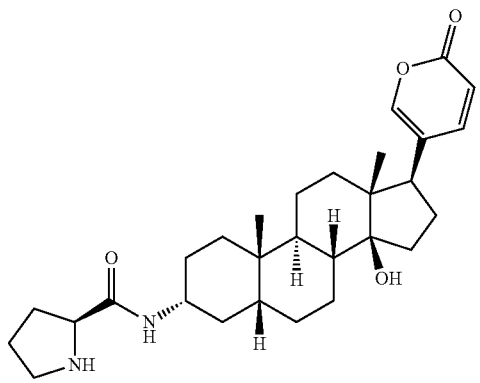

(S)-N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)pyrrolidine-2-carboxamide (S)—N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)pyrrolidine-2-carboxamide (16.4 mg) was prepared as described for 2-amino-N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)acetamide. LRMS (M+H$^+$) m/z calculated 483.3, found 483.3. $^1$H NMR (CD$_3$OD, 400 MHz) δ 7.99 (dd, 1 H), 7.43 (d, 1 H), 6.28 (d, 1 H), 4.55 (brs, 1 H), 3.96 (t, 1 H), 3.68-3.72 (m, 1 H), 3.14-3.31 (m, 2H), 2.53-2.58 (m, 1 H), 2.10-2.34 (m, 3 H), 1.06-1.98 (m, 24 H), 0.89 (s, 3 H), 0.61 (s, 3H).

Example 33

Preparation of (S)—N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)pyrrolidine-2-carboxamide

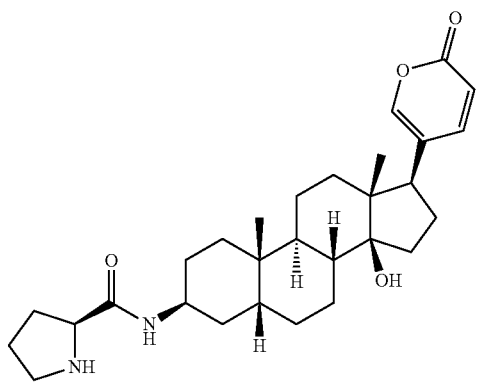

(S)-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)pyrrolidine-2-carboxamide (S)—N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)pyrrolidine-2-carboxamide (7.4 mg) was prepared as described for 2-amino-N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)acetamide. LRMS (M+H$^+$) m/z calculated 483.3, found 483.3. $^1$H NMR (CD$_3$OD, 400 MHz) δ 7.89 (dd, 1 H), 7.33 (d, 1 H), 6.18 (d, 1 H), 4.04-4.07 (m, 2 H), 3.15-3.26 (m, 2 H), 2.44-2.47 (m, 1 H), 2.26-2.32 (m, 1H), 1.10-2.12 (m, 27 H), 0.82 (s, 3 H), 0.62 (s, 3H).

Example 34

Preparation of (2R)—N-((5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)pyrrolidine-2-carboxamide

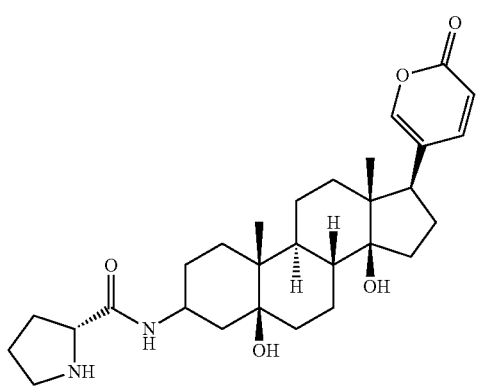

(2R)-N-((5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)pyrrolidine-2-carboxamide (2R)—N-((5S,8R,9S,10R,13R,14S,17R)-5,14-dihydroxy-10,13-dimethyl-17-(2-oxo-2H-pyran-5-yl)hexadecahydro-1H-cyclopenta[a]phenanthren-3-yl)pyrrolidine-2-carboxamide (7.2 mg) was prepared as described for 2-amino-N-((3R,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)acetamide. LRMS (M+H$^!$) m/z calculated 499.3, found 499.3. $^1$H NMR (CDCl$_3$, 400 MHz) δ 8.49 (d, 1H), 7.82 (dd, 1 H), 7.25 (d, 1 H), 6.27 (d, 1 H), 4.23-4.25 (m, 1 H), 3.81-3.85 (m, 1 H), 3.02-3.06 (m, 2 H), 2.01-2.51 (m, 9H), 1.31-1.98 (m, 20 H), 0.93 (s, 3 H), 0.71 (s, 3H).

Example 35

Preparation of (2R)-2-amino-N-((5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N,3-dimethylbutanamide

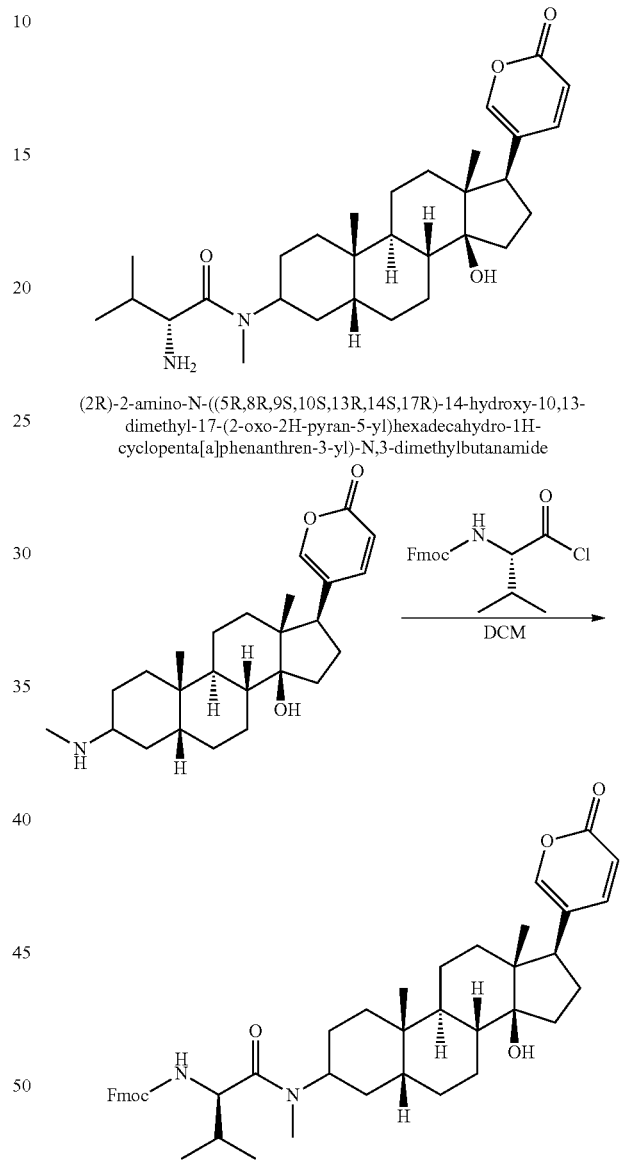

(2R)-2-amino-N-((5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N,3-dimethylbutanamide To a solution of 5-((5R,8R,9S,10S,13R,14S,17R)-14-hydroxy-10,13-dimethyl-3-(methylamino)hexadecahydro-1H-cyclopenta[a]phenanthren-17-yl)-2H-pyran-2-one (50 mg, 0.125 mmol, 1 eq.) in a mixture of sat. NaHCO3 (10 mL) solution and DCM (10 mL) was added (S)-(9H-fluoren-9-yl)methyl (1-chloro-3-methyl-1-oxobutan-2-yl)carbamate (64 mg, 0.18 mmol, 1.5 eq.) at 0° C. After being stirred at RT for 2 h, the mixture was washed with sat. Na$_2$CO$_3$ (10 mL) solution and extracted with DCM (3×20 mL). The combined organic layers were dried over anhydrous Na$_2$SO$_4$ and concentrated. The residue was purified via flash column chromatography (PE/EA=1:2, v/v) to afford (9H-fluoren-9-yl)methyl ((2R)-1-(((5R,8R,9S,10S,13R,14S,17R)-14-hydroxy-10,13-dimethyl-17-(2-oxo-2H-pyran-5-yl)hexadeca-hydro-1H-cyclopenta[a]phenanthren-3-yl)(methyl)amino)-3-methyl-1-oxobutan-2-yl)carbamate (78 mg, 86%).

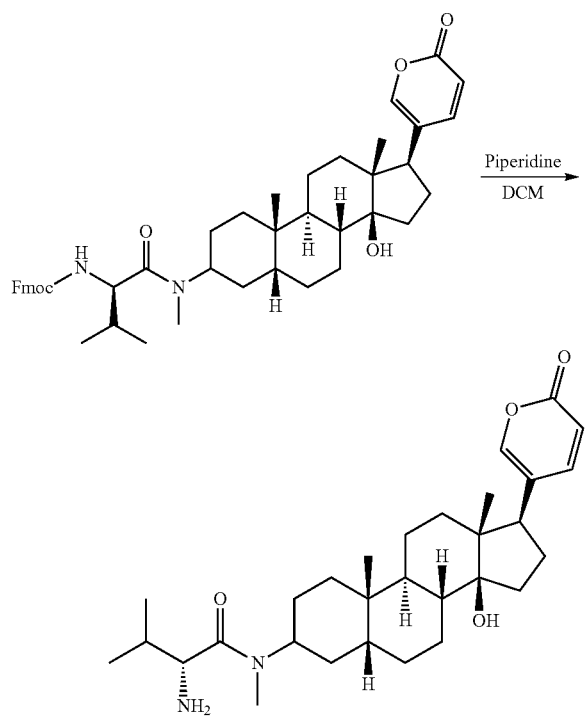

To a solution of (9H-fluoren-9-yl)methyl ((2R)-1-(((5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)(methyl)amino)-3-methyl-1-oxobutan-2-yl)carbamate (78 mg, 0.11 mmol, 1 eq.) in DCM (3 mL) was added piperidine (8 drops). After being stirred at r.t overnight, the reaction mixture was concentrated and purified by Prep-HPLC to afford (2R)-2-amino-N-((5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-N,3-dimethylbutanamide (10.8 mg, 20%). LRMS (M+H$^1$) m/z calculated 499.3, found 499.4. $^1$H NMR (CD$_3$OD, 400 MHz) δ7.89 (dd, 1 H), 7.33 (s, 1 H), 6.18 (d, 1 H), 5.39 (s, 1 H), 2.81-2.99 (m, 3 H), 2.07-2.08 (m, 1 H), 1.21-2.07 (m, 26H), 0.85-0.94 (m, 9 H), 0.61 (s, 3 H).

Example 36

Measurement of Equilibrium Solubility

The equilibrium solubility of compounds was measured in aqueous buffer. Excess amount of solid compound was added into buffer solution and the sample was briefly sonicated and then shaken at rt for 24 h. The sample was filtered and the concentration was analyzed by HPLC UV. A standard solution at 0.2 mg/mL was prepared in methanol or acetonitrile for each compound and used as an external standard for quantification. Data for representative compounds in NaOAc/AcOH buffer (100 mM, pH 5.0) are shown in Table 2. The scale utilized in Tables 2 is as follows: +++ greater than 1 mg/mL; ++ between 1 and 0.1 mg/mL; and + less than 0.1 mg/mL.

TABLE 2

| Solubility of several illustrative compounds | |
|---|---|
| Solubility | Compounds |
| +++ | C04, C10, C12, C18, C20, C22, C24, C26, C27, C28 |
| ++ | C19, C30 |
| + | C02, C32 |

Example 37

Inhibition of Cancer Cell Growth by Compounds Using MTT Assay

Inhibition of cell growth by compounds was measured using MTT assay (Mosmann, T., Journal of Immunological Methods, 1983, 65, 55-63). Tumor cell lines were purchased from ATCC (American Type Culture Collection, Manassas, Va.). All cell lines were maintained in RPMI 1640 (Hyclone) supplemented with 10% fetal bovine serum (FBS, Hyclone), glutamine (2 mM, Hyclone), and antibiotics (penicillin 100 U/mL and streptomycin 50 µg/mL) at 37° C. in a humidified atmosphere of 5% CO$_2$ in air. Taxol (as a positive control, Sigma) and compounds were dissolved in DMSO (Sigma), and the final concentration of DMSO in the medium was 1%. Tumor cells were plated in 96-well plates at densities of about 4000 cells/well of a 96-well plate and allowed to adhere/grow for 24 h. They were then treated with various concentrations of drug for 72 h. 3-(4,5-Dimethylthiazol-2-yl)-2,5-diphenyltetrazolium bromide (MTT, Sigma) was used to determine the number of viable cells at the time of compound addition and the number of cells remaining after 72 h compound exposure. The number of cells remaining after 72 h was compared to the number of viable cells at the time of compound addition by measuring the absorbance at 570 nm, allowing for the calculation of growth inhibition.

All concentrations of compounds were tested in triplicate and controls were averaged over 4 wells. IC$_{50}$ was calculated by plotting the concentration of compound vs the percentage of inhibition in treated wells using GraphPad Prism 5. Data for representative compounds are shown below. Table 3 shows IC$_{50}$ values of several compounds of the invention against A549 cells. The scale utilized in Table 3 is as follows: ++++ less than 20 nM; +++ between 20 nM and 100 nM; ++ between 100 nM and 1000 nM; and + greater than 1000 nM.

TABLE 3

| IC$_{50}$ of several illustrative compounds in A549 cells | |
|---|---|
| IC$_{50}$ | Compounds |
| ++++ | C02, C03, C04, C06, C10, C12, C14, C15, C16, C17, C20, C21, C25, C26, C27, C29, C31, C35 |
| +++ | C09, C11, C19, C22, C24, C30 |
| ++ | C01, C05, C07, C08, C13, C18, C23, C28, C32 |
| + | C34 |

Example 38

Inhibition of Tumor Growth in Xenograft Model

Cells were implanted in BALB/c female nude mice and grown as tumor xenografts. When tumors achieved 120-200 mm$^3$, mice were assigned into treatment and control groups using randomized block design based upon their tumor volumes. Each group contained 6 tumor-bearing mice. Tumors were measured twice weekly in two dimensions using a caliper, and the tumor volume was calculated from two-dimensional measurements using the equation $V=0.5 \times a \times b^2$ where a and b are the long and short diameters of the tumor, respectively. Relative tumor volume (RTV) was defined as $TV_t/TV_i$, the ratio of the volume on a given day ($TV_t$) and the volume at the start of treatment ($TV_i$). Relative tumor growth rate (T/C) was defined as $RTV_T/RTV_c$, the ratio of relative tumor volume of treatment group ($RTV_T$) and relative tumor volume of control group ($RTV_c$) on a given day. Inhibition of tumor growth in a A549 tumor xenograft model is shown below in Table 4 for a compound of Table 1.

TABLE 4

In vivo activity of an illustrative compound in A549 tumor model

| Compound | Dose (mg/kg) | Schedule | Route | Tumor Volume Pre-treatment (mm³) | Tumor Volume Post-treatment (mm³) | T/C |
|---|---|---|---|---|---|---|
| Vehicle | — | qd X 21 | i.v. | 279 | 2083 | — |
| Compound | 2 | qd X 21 | i.v. | 278 | 1238 | 60%** |

**p < 0.01

While some embodiments have been shown and described, various modifications and substitutions may be made thereto without departing from the spirit and scope of the invention. For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims.

What is claimed is:

1. A compound of Formula I:

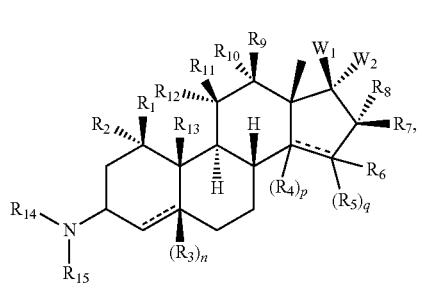

Formula I or pharmaceutically acceptable salt thereof, wherein:
$R_1$, $R_2$, $R_3$, $R_4$, $R_5$, $R_6$, $R_9$, $R_{10}$, $R_{11}$ and $R_{12}$ are independently selected from the group consisting of hydrogen, hydroxy, optionally substituted alkyl, optionally substituted cycloalkyl, optionally substituted alkenyl, optionally substituted alkynyl, optionally substituted alkoxy, optionally substituted aryloxy, optionally substituted heteroaryloxy, optionally substituted heterocycloalkyloxy, optionally substituted aminocarbonyloxy, optionally substituted acyloxy, optionally substituted alkoxycarbonyloxy, and optionally substituted amino; or $R_1$ and $R_2$, or $R_5$ and $R_6$, or $R_7$ and $R_8$, or $R_9$ and $R_{10}$, or $R_{11}$ and $R_{12}$ mutually independently, together in each case denote an oxo group (=O); or $R_4$ and $R_5$ may optionally be joined together with any intervening atoms to form an optionally substituted heterocycloalkyl ring;

$R_7$ is selected from the group consisting of hydrogen, hydroxy, optionally substituted alkoxy, optionally substituted aryloxy, optionally substituted heteroaryloxy, optionally substituted heterocycloalkyloxy, optionally substituted aminocarbonyloxy, optionally substituted acyloxy, optionally substituted alkoxycarbonyloxy, and optionally substituted amino;

$R_8$ is selected from the group consisting of hydrogen, optionally substituted alkyl, optionally substituted cycloalkyl, optionally substituted alkenyl, and optionally substituted alkynyl;

$R_{13}$ is selected from the group consisting of hydrogen, optionally substituted alkyl, and formyl;

$R_{14}$ is selected from the group consisting of optionally substituted alkyl, optionally substituted cycloalkyl, optionally substituted heterocycloalkyl, optionally substituted aryl, and optionally substituted heteroaryl;

$R_{15}$ is selected from the group consisting of —CONR$_{17}$R$_{18}$, —C(NR$_{19}$)NR$_{17}$R$_{18}$, —C(NCN)NR$_{17}$R$_{18}$, —SO$_2$R$_{16}$, and —SO$_2$NR$_{17}$R$_{18}$;

$R_{16}$ is selected from the group consisting of optionally substituted alkyl, optionally substituted cycloalkyl, optionally substituted heterocycloalkyl, optionally substituted aryl, and optionally substituted heteroaryl;

$R_{17}$ is selected from the group consisting of optionally alkyl, optionally substituted cycloalkyl, optionally substituted heterocycloalkyl, optionally substituted aryl and optionally substituated heteroaryl;

$R_{18}$ and $R_{19}$ are independently selected from the group consisting of hydrogen, optionally substituted alkyl, optionally substituted cycloalkyl, optionally substituted heterocycloalkyl, optionally substituted aryl, and optionally substituted heteroaryl;

$W_1$ is:

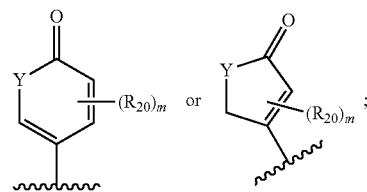

Y is selected from the group consisting of O and NR$_{21}$;

$R_{20}$ is selected from the group consisting of cyano, halo, hydroxy, azido, nitro, carboxy, sulfinyl, sulfanyl, sulfonyl, optionally substituted alkoxy, optionally substituted aryloxy, optionally substituted heteroaryloxy, optionally substituted heterocycloalkyloxy, optionally substituted alkoxycarbonyl, optionally substituted alkyl, optionally substituted alkenyl, optionally substituted aryl, optionally substituted heteroaryl, optionally substituted heterocycloalkyl, optionally substituted amino, optionally substituted acyl, optionally substituted aminocarbonyl, optionally substituted aminosulfonyl, optionally substituted carbaminodoyl, and optionally substituted alkynyl;

$R_{21}$ is selected from the group consisting of hydrogen, optionally substituted alkyl, optionally substituted cycloalkyl, optionally substituted heterocycloalkyl, optionally substituted aryl, and optionally substituted heteroaryl;

$W_2$ is selected from the group consisting of hydrogen, optionally substituted alkyl, optionally substituted cycloalkyl, optionally substituted alkenyl, and optionally substituted alkynyl;

m is selected from 0, 1, 2, and 3;

n, p, and q are independently selected from 0 and 1; and each ═ independently represents a single bond or a double bond.

2. The compound of claim 1, wherein $R_1$, $R_2$, $R_3$, $R_4$, $R_5$, $R_6$, $R_9$, $R_{10}$, $R_{11}$ and $R_{12}$ are independently selected from the group consisting of hydrogen, hydroxy, optionally substituted alkyl, optionally substituted alkoxy, optionally substituted aminocarbonyloxy, optionally substituted acyloxy, optionally substituted alkoxycarbonyloxy, and optionally substituted amino.

3. The compound of claim 2, wherein $R_1$, $R_2$, $R_3$, $R_4$, $R_5$, $R_6$, $R_9$, $R_{10}$, $R_{11}$ and $R_{12}$ are independently selected from the group consisting of hydrogen, hydroxy, and optionally substituted alkyl.

4. The compound of claim 1, wherein $R_4$ is hydroxy.

5. The compound of claim 1, wherein $R_4$ and $R_5$ are joined together with any intervening atoms to form an optionally substituted 3- to 8-membered heterocycloalkyl ring.

6. The compound of claim 1, wherein $R_7$ is selected from the group consisting of hydrogen, hydroxy, optionally substituted alkoxy, optionally substituted aminocarbonyloxy, optionally substituted acyloxy, optionally substituted alkoxycarbonyloxy, and optionally substituted amino.

7. The compound of claim 6, wherein $R_7$ is selected from the group consisting of hydrogen and —OCOCH$_3$.

8. The compound of claim 1, wherein $R_8$ and $W_2$ are independently selected from the group consisting of hydrogen and optionally substituted alkyl.

9. The compound of claim 1, wherein $R_{13}$ is selected from the group consisting of hydrogen, methyl, and hydroxymethyl.

10. The compound of claim 1, wherein Y is selected from the group consisting of O, NH and NCH$_3$.

11. The compound of claim 1, wherein $R_{20}$ is selected from the group consisting of cyano, halo, hydroxy, carboxy, sufonyl, optionally substituted alkoxy, optionally substituted alkoxycarbonyl, optionally substituted alkyl, optionally substituted amino, optionally substituted acyl, optionally substituted aminocarbonyl, and optionally substituted aminosulfonyl.

12. The compound of claim 1, wherein each ═ represents a single bond.

13. The compound of claim 1, wherein each ═ represents a double bond.

14. The compound of claim 1, wherein the compound of Formula I is selected from the group consisting of compounds of Formula Ia:

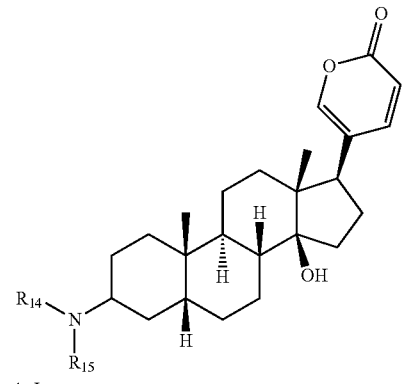

Formula Ia

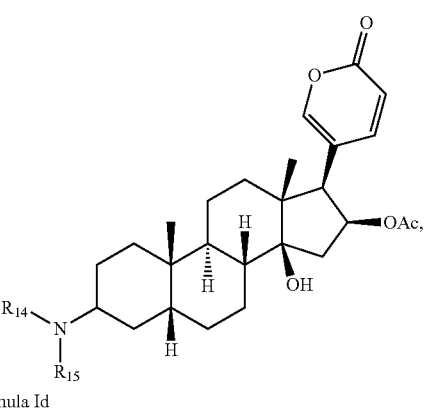

Formula Ib

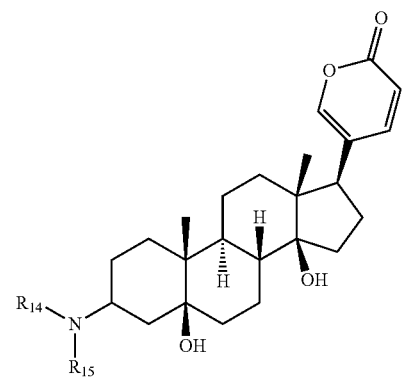

Formula Ic

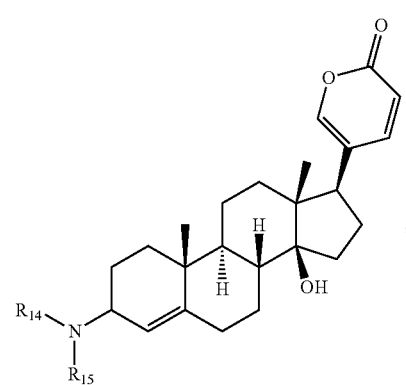

Formula Id

Formula If
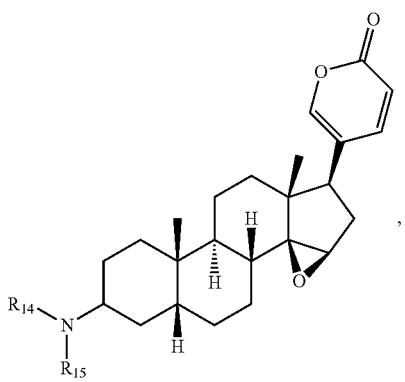
Formula Ig
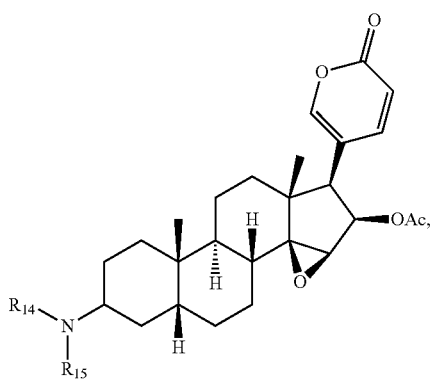
Formula Ih
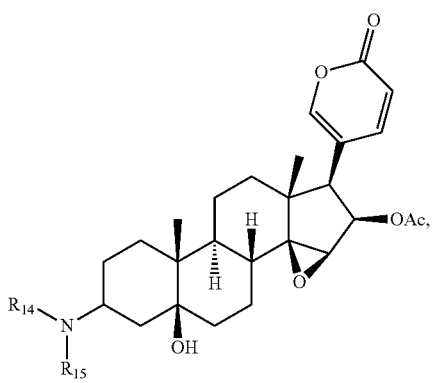
Formula Ii
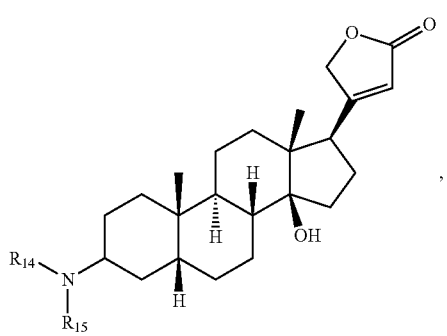
Formula Ij
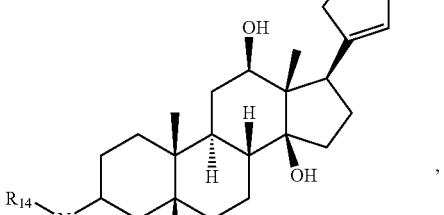
Formula Ik
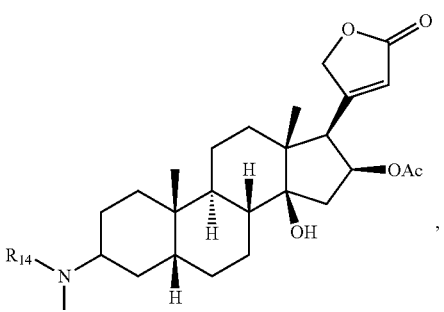
Formula Il
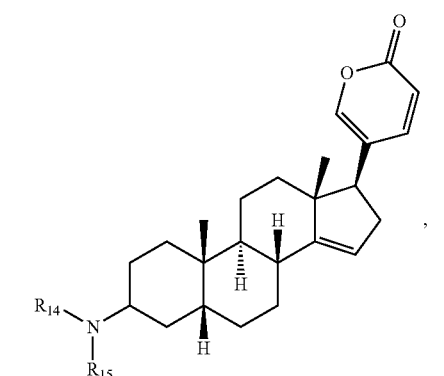
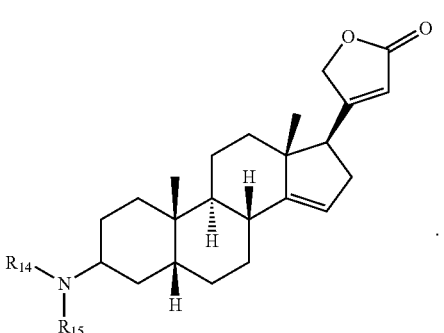
, and
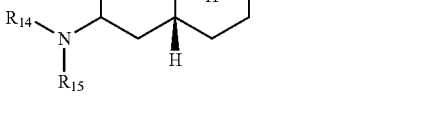
15. The compound of claim 1, wherein $R_{14}$ is selected from the group consisting of optionally substituted lower alkyl, optionally substituted cycloalkyl, optionally substituted heterocycloalkyl, optionally substituted aryl, and optionally substituted heteroaryl.

16. The compound of claim 15, wherein $R_{14}$ is selected from the group consisting of optionally substituted lower alkyl.

17. The compound of claim 1, wherein $R_{15}$ is selected from the group consisting of —$CONR_{17}R_{18}$ and —$SO_2NR_{17}R_{18}$.

18. The compound of claim 1, wherein $R_{14}$ is optionally substituted alkyl, optionally substituted cycloalkyl, or optionally substituted heterocycloalkyl.

19. The compound of claim 1, wherein $R_{16}$ is selected from the group consisting of optionally substituted alkyl, optionally substituted cycloalkyl, optionally substituted heterocycloalkyl, optionally substituted aryl, and optionally substituted heteroaryl; and $R_{19}$ is selected from the group consisting of hydrogen, optionally substituted alkyl, optionally substituted cycloalkyl, and optionally substituted heterocycloalkyl.

20. The compound of claim 19, wherein $R_{16}$ is selected from the group consisting of optionally substituted alkyl, optionally substituted cycloalkyl, and optionally substituted heterocycloalkyl: $R_{17}$ is selected from the group consisting of optionally substituted alkyl, optionally substituted cycloalkyl, and optionally substituted heterocycloalkyl; and $R_{18}$ is selected from the group consisting of hydrogen, optionally substituted alkyl, optionally substituted cycloalkyl, and optionally substituted heterocycloalkyl; and $R_{19}$ is selected from the group consisting of hydrogen and optionally substituted alkyl.

21. A pharmaceutical composition comprising a pharmaceutically acceptable carrier and the compound of claim 1.

22. A method of ameliorating symptoms or slowing progression of lung cancer is a subject, the method comprising administering to the subject in need thereof a therapeutically effective amount of the compound of claim 1.

23. A method of ameliorating symptoms or slowing progression of lung cancer in a subject, the method comprising administering to the subject in need thereof a therapeutically effective amount of a compound of Formula I:

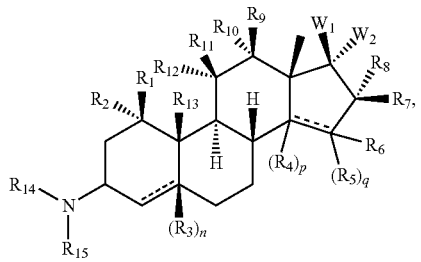

Formula I or pharmaceutically acceptable salt thereof, wherein:
$R_1$, $R_2$, $R_3$, $R_4$, $R_5$, $R_6$, $R_9$, $R_{10}$, $R_{11}$ and $R_{12}$ are independently selected from the group consisting of hydrogen, hydroxy, optionally substituted alkyl, optionally substituted cycloalkyl, optionally substituted alkenyl, optionally substituted alkynyl, optionally substituted alkoxy, optionally substituted aryloxy, optionally substituted heteroaryloxy, optionally substituted heterocycloalkyloxy, optionally substituted aminocarbonyloxy, optionally substituted acyloxy, optionally substituted alkoxycarbonyloxy, and optionally substituted amino; or $R_1$ and $R_2$, or $R_5$ and $R_6$, or $R_7$ and $R_8$, or $R_9$ and $R_{10}$, or $R_{11}$ and $R_{12}$ mutually independently, together in each case denote an oxo group (=O); or $R_4$ and $R_5$ may optionally be joined together with any intervening atoms to form an optionally substituted heterocycloalkyl ring;

$R_7$ is selected from the group consisting of hydrogen, hydroxy, optionally substituted alkoxy, optionally substituted aryloxy, optionally substituted heteroaryloxy, optionally substituted heterocycloalkyloxy, optionally substituted aminocarbonyloxy, optionally substituted acyloxy, optionally substituted alkoxycarbonyloxy, and optionally substituted amino;

$R_8$ is selected from the group consisting of hydrogen, optionally substituted alkyl, optionally substituted cycloalkyl, optionally substituted alkenyl, and optionally substituted alkynyl;

$R_{13}$ is selected from the group consisting of hydrogen, optionally substituted alkyl, and formyl;

$R_{14}$ is selected from the group consisting of hydrogen, optionally substituted alkyl, optionally substituted cycloalkyl, optionally substituted heterocycloalkyl, optionally substituted aryl, and optionally substituted heteroaryl;

$R_{15}$ is —$COR_{16}$, wherein $R_{16}$ is an alkyl substituted with one or more substituents independently selected from the group consisting of optionally substituted $C_1$-$C_6$ alkyl, optionally substituted cycloalkyl, optionally substituted heterocycloalkyl, optionally substituted alkenyl, optionally substituted alkynyl, optionally substituted aryl, optionally substituted heteroaryl, optionally substituted amino, halo, cyano, azido, nitro, oxo, optionally substituted acyl, optionally substituted alkoxycarbonyl, aminocarbonyl, sulfanyl, sulfinyl, and sulfonyl;

$W_1$ is:

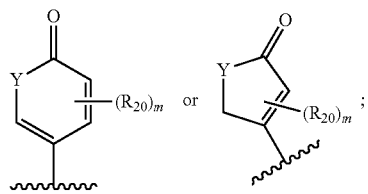

Y is selected from the group consisting of O and $NR_{21}$;
$R_{20}$ is selected from the group consisting of cyano, halo, hydroxy, azido, nitro, carboxy, sulfinyl, sulfanyl, sulfonyl, optionally substituted alkoxy, optionally substituted aryloxy, optionally substituted heteroaryloxy, optionally substituted heterocycloalkyloxy, optionally substituted alkoxycarbonyl, optionally substituted alkyl, optionally substituted alkenyl, optionally substituted aryl, optionally substituted heteroaryl, optionally substituted heterocycloalkyl, optionally substituted amino, optionally substituted acyl, optionally substituted aminocarbonyl, optionally substituted aminosulfonyl, optionally substituted carbaminodoyl, and optionally substituted alkynyl;

$R_{21}$ is selected from the group consisting of hydrogen, optionally substituted alkyl, optionally substituted cycloalkyl, optionally substituted heterocycloalkyl, optionally substituted aryl, and optionally substituted heteroaryl;

$W_2$ is selected from the group consisting of hydrogen, optionally substituted alkyl, optionally substituted cycloalkyl, optionally substituted alkenyl, and optionally substituted alkynyl;

m is selected from 0, 1, 2, and 3;

n, p, and q are independently selected from 0 and 1; and each ═ independently represents a single bond or a double bond.

24. The method of claim 23, wherein $R_1$, $R_2$, $R_3$, $R_4$, $R_5$, $R_6$, $R_9$, $R_{10}$, $R_{11}$ and $R_{12}$ are independently selected from the group consisting of hydrogen, hydroxy, optionally substituted alkyl, optionally substituted alkoxy, optionally substituted aminocarbonyloxy, optionally substituted acyloxy, optionally substituted alkoxycarbonyloxy, and optionally substituted amino.

25. The method of claim 24, wherein $R_1$, $R_2$, $R_3$, $R_4$, $R_5$, $R_6$, $R_9$, $R_{10}$, $R_{11}$ and $R_{12}$ are independently selected from the group consisting of hydrogen, hydroxy, and optionally substituted alkyl.

26. The method of claim 23, wherein $R_4$ is hydroxy.

27. The method of claim 23, wherein $R_4$ and $R_5$ are joined together with any intervening atoms to form an optionally substituted 3- to 8-membered heterocycloalkyl ring.

28. The method of claim 23, wherein $R_7$ is selected from the group consisting of hydrogen, hydroxy, optionally substituted alkoxy, optionally substituted aminocarbonyloxy, optionally substituted acyloxy, optionally substituted alkoxycarbonyloxy, and optionally substituted amino.

29. The method of claim 28, wherein $R_7$ is selected from the group consisting of hydrogen and —OCOCH$_3$.

30. The method of claim 23, wherein $R_8$ and $W_2$ are independently selected from the group consisting of hydrogen and optionally substituted alkyl.

31. The method of claim 23, wherein $R_{13}$ is selected from the group consisting of hydrogen, methyl, and hydroxymethyl.

32. The method of claim 23, wherein Y is selected from the group consisting of O, NH and NCH$_3$.

33. The method of claim 23, wherein $R_{20}$ is selected from the group consisting of cyano, halo, hydroxy, carboxy, sulfonyl, optionally substituted alkoxy, optionally substituted alkoxycarbonyl, optionally substituted alkyl, optionally substituted amino, optionally substituted acyl, optionally substituted aminocarbonyl, and optionally substituted aminosulfonyl.

34. The method of claim 23, wherein each ═ represents a single bond.

35. The method of claim 23, wherein each ═ represents a double bond.

36. The method of claim 23, wherein the compound of Formula I is selected from the group consisting of compounds of Formula Ia:

Formula Ia

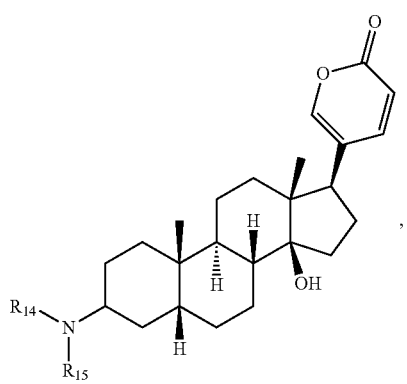

Formula Ib:

Formula Ib

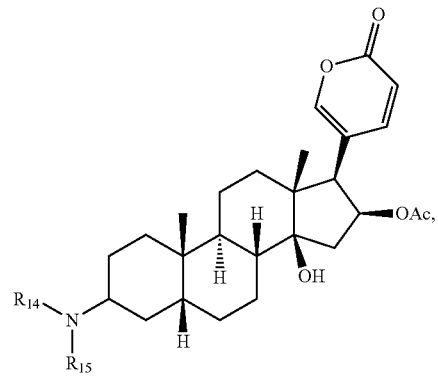

Formula Ic:

Formula Ic

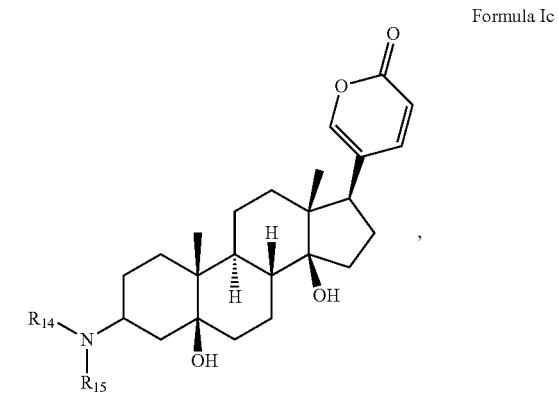

Formula Id:

Formula Id

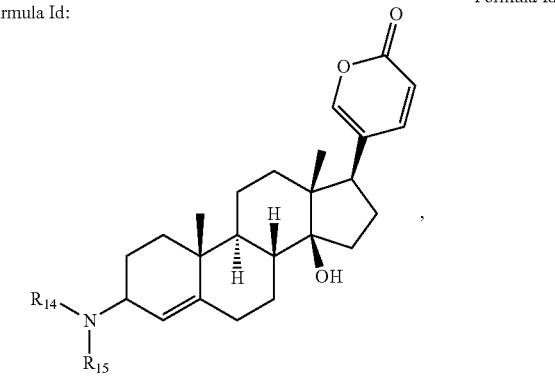

Formula Ie:

Formula Ie

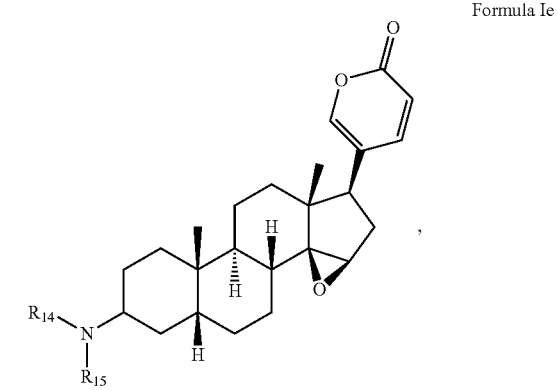

-continued

Formula If:

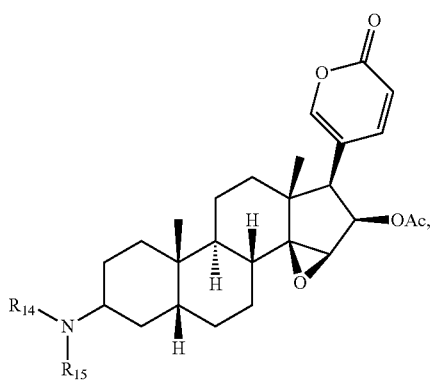

Formula If

Formula Ig:

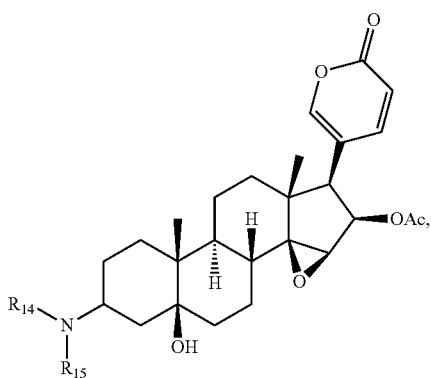

Formula Ig

Formula Ih:

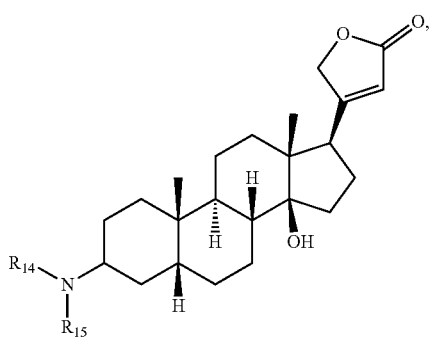

Formula Ih

Formula Ii:

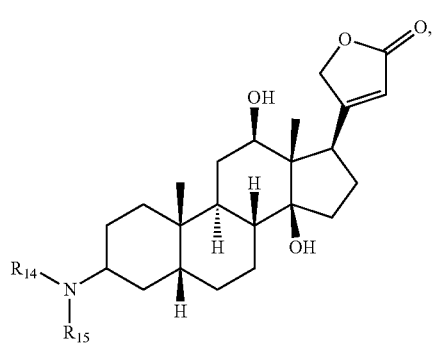

Formula Ii

-continued

Formula Ij:

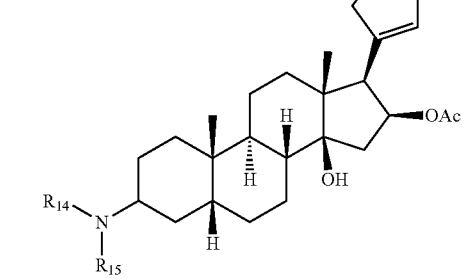

Formula Ij

Formula Ik:

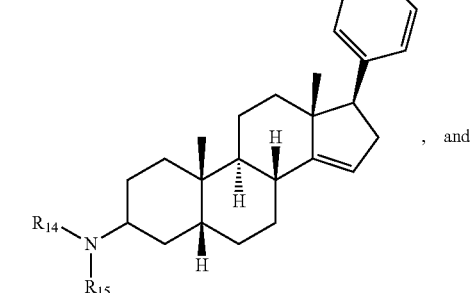

Formula Ik

, and

Formula Il:

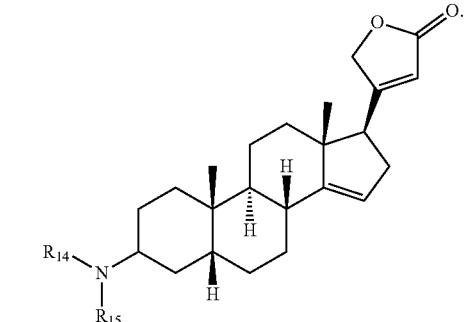

Formula Il

37. The method of claim 23, wherein $R_{14}$ is selected from the group consisting of hydrogen, optionally substituted lower alkyl, optionally substituted cycloalkyl, optionally substituted heterocycloalkyl, optionally substituted aryl, and optionally substituted heteroaryl.

38. The method of claim 37, wherein $R_{14}$ is selected from the group consisting of hydrogen and optionally substituted lower alkyl.

39. The method of claim 23, wherein $R_{14}$ is not hydrogen.

40. The method of claim 23, wherein $R_{14}$ is optionally substituted alkyl, optionally substituted cycloalkyl, or optionally substituted heterocycloalkyl.

41. The method of claim 23, wherein $R_{16}$ is an alkyl substituted with one or more substituents independently selected from the group consisting of optionally substituted $C_1$-$C_6$ alkyl, optionally substituted cycloalkyl and optionally substituted amino.

42. The method of claim 23, wherein the compound is selected from the group consisting of:

2-amino-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)acetamide, N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-2-(pyrrolidin-1-yl)acetamide, N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)-2-morpholinoacetamide, (R)-2-amino-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)propanamide, (S)-2-amino-N-((3S,5R,8R,9S,10S, 13R, 14S, 17R)-14hydroxy-10, 13-dimethyl-17-(2-oxo-2H-pyran-5-yl)hexadecahydro-1H-cyclopenta[a]phenanthren3-yl)propanamide, (R)-2-amino-N-((3S,5R,8R,9S,10S,13R,14S,17R)-14-hydroxy-10,13-dimethyl-17-(2-oxo-2H-pyran-5-yl)hexadecahydro-1H-cycopenta[a]phenanthren-3-yl)-3-methylbutanamide, (S)-2-amino-N-((3S,5R,8R,9S,10S,13R,14S,17R)-14-hydroxy-10,13-dimethyl-17-(2-oxo-2H-pyran-5-yl)hexadecahydro-1H-cyclopenta[a       ]phenanthren-3-yl)-3-methylbutanamide, (R)-2-amino-N1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)succinamide, (S)-2-amino-N1-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)succinamide, 2-amino-N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)acetamide, (R)-2-amino-N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)propanamide, (S)-2-amino-N-((3S,5R,8R,9S,10S,13R,14S,17R)-14-hydroxy-10,13-dimethyl-17-(5-oxo-2,5-dihydrofuran-3-yl) hexadecahydro-1H-cyclopenta[a]phenanthren-3-yl)propanamide, (R)-2-amino-N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-3-methylbutanamide, (S)-2-amino-N-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)-3-methylbutanamide, (R)-2-amino-N1-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)succinamide, (S)-2-amino-N1-((3S,5R,8R,9S,10S,13R,14S,17R)-14-hydroxy-10,13-dimethyl-17-(5-oxo-2,5-dihydrofuran-3-yl)hexadecahydro-1H-cyclopenta[a]phenanthren-3-yl)succinamide, (2R)-2-amino-N-((3S,5R,8R,9S,10S,13S,17S)-10,13-dimethyl-17-(5-oxo-2,5-dihydrofuran-3-yl)hexadecahydro-1H-cyclopenta[a]phenanthren-3-yl)propanamide, or a pharmaceutically acceptable salt thereof.

\* \* \* \* \*

UNITED STATES PATENT AND TRADEMARK OFFICE
CERTIFICATE OF CORRECTION

PATENT NO.         : 10,487,108 B2
APPLICATION NO.    : 15/586710
DATED              : November 26, 2019
INVENTOR(S)        : Xiangping Qian Page 1 of 7

It is certified that error appears in the above-identified patent and that said Letters Patent is hereby corrected as shown below:

In the Claims

• Claim 1: Column 126, Lines 32-33:
"$R_{17}$ is selected from the group consisting of optionally alkyl"
Should read:
-- $R_{17}$ is selected from the group consisting of optionally substituted alkyl --.

• Claim 4: Column 127, Line 65 - Column 130, Line 60:
"The compound of claim 1, wherein the compound of Formula I is selected from the group consisting of compounds of Formula Ia:
Formula Ib

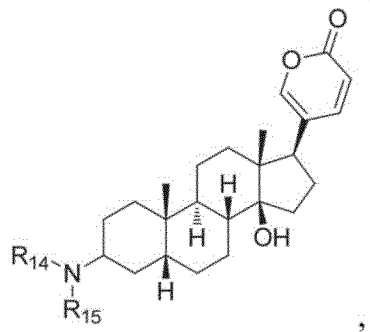

Formula Ia

Signed and Sealed this
Twenty-third Day of June, 2020

Andrei Iancu
*Director of the United States Patent and Trademark Office*

Formula Ic
Formula Ib
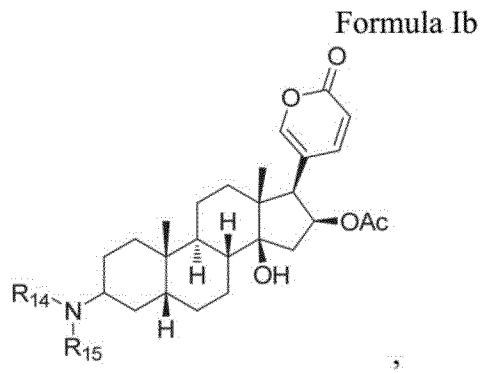
,
Formula Id
Formula Ic
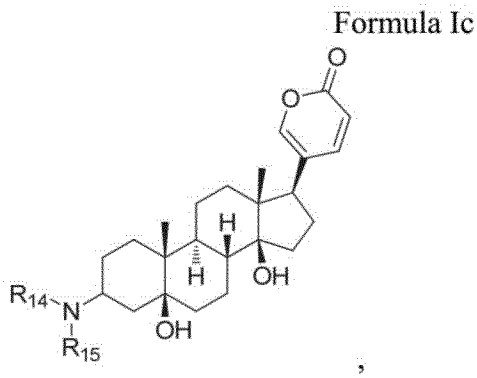
,
Formula Ie
Formula Id
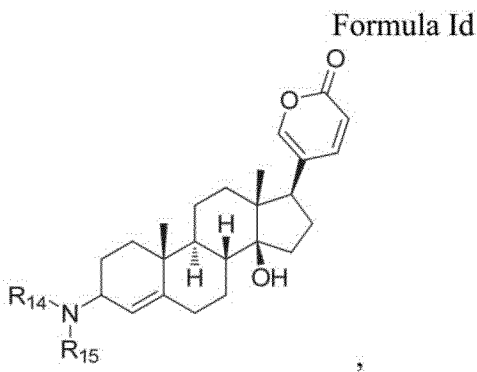
,
Formula If
Formula Ie
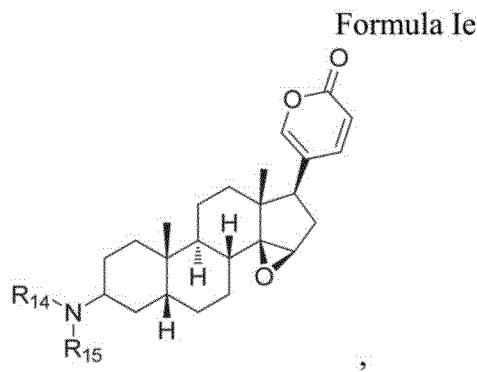
, Formula If
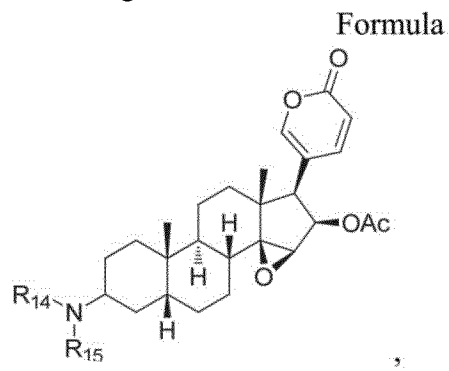
Formula Ig
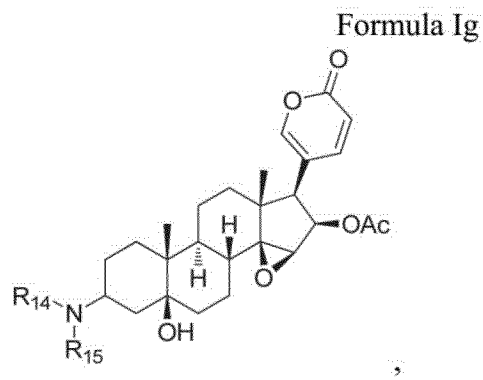
Formula Ih
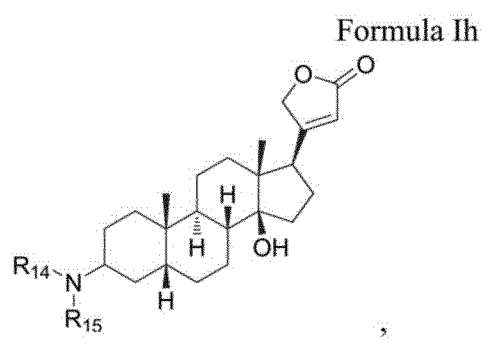
Formula Ii
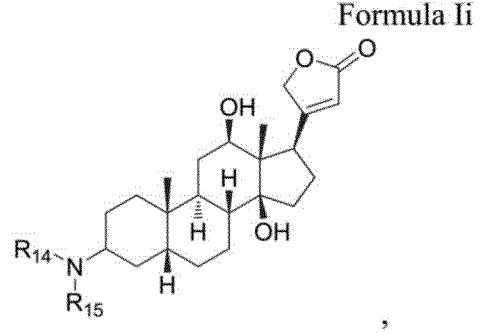

Formula Ik
Formula Ij
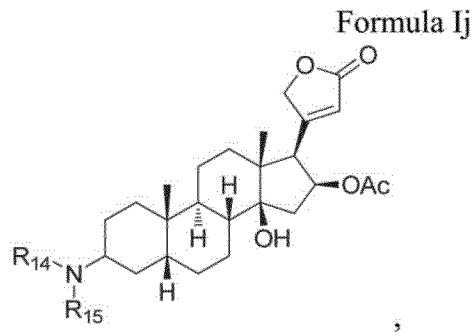
,
Formula Il
Formula Ik
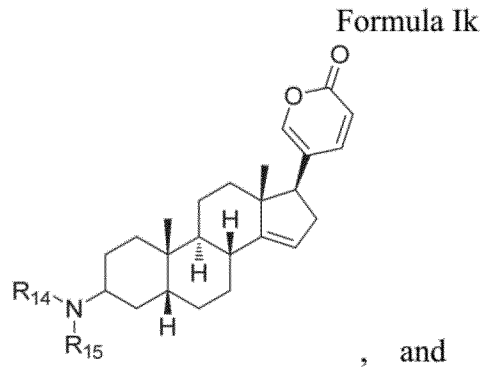
, and
Formula Il
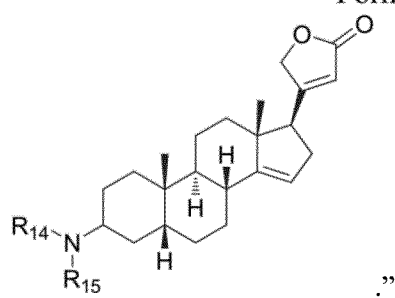
."
Should read:
-- The compound of claim 1, wherein the compound of Formula I is selected from the group consisting of compounds of Formula Ia:
Formula Ia
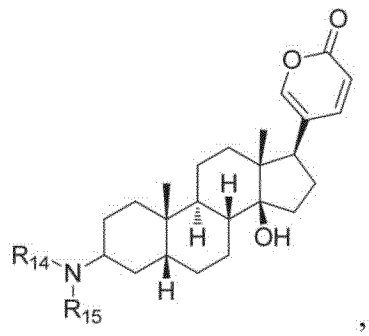
, Formula Ib:
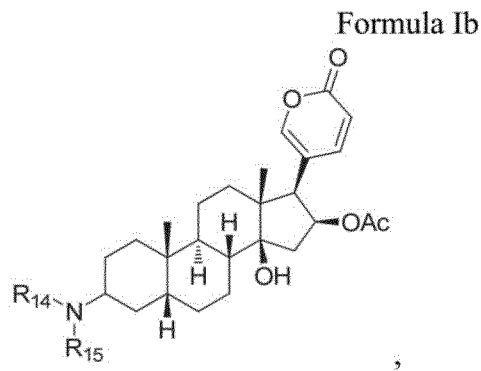
,
Formula Ic:
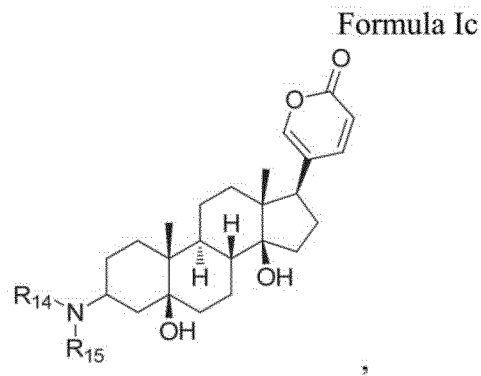
,
Formula Id:
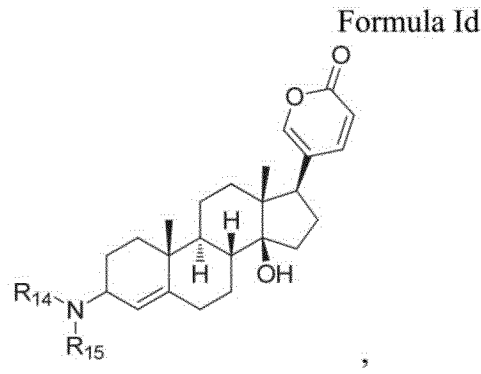
,
Formula Ie:
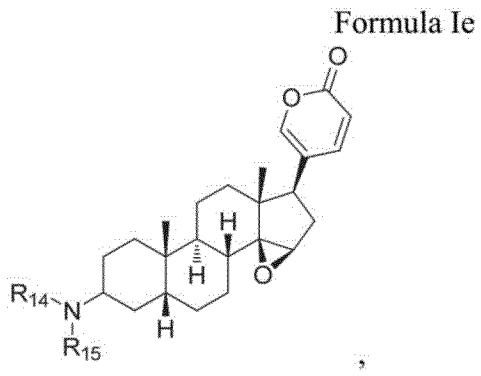
, Formula If:
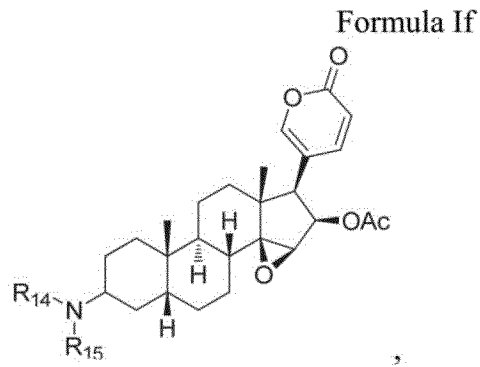
Formula Ig:
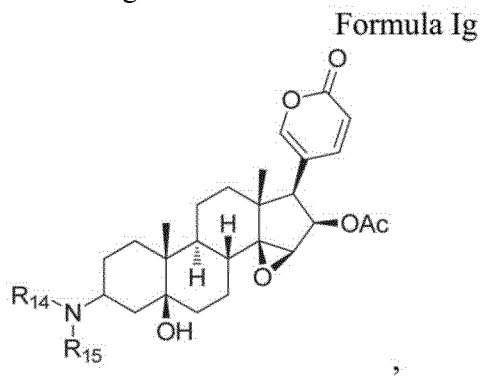
Formula Ih:
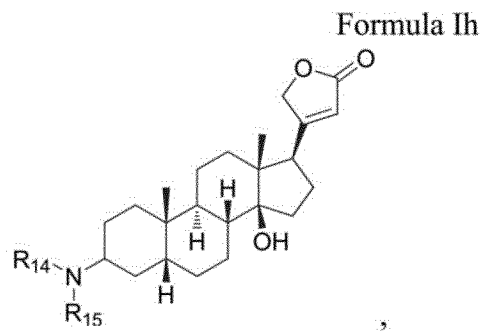
Formula Ii:
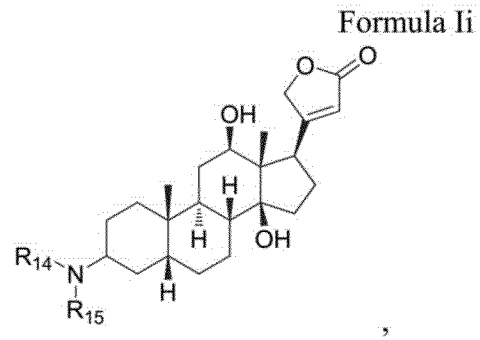

Formula Ij:
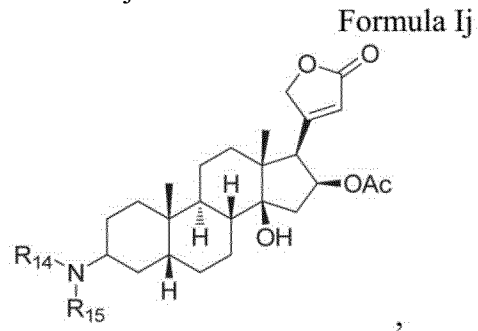
Formula Ik:
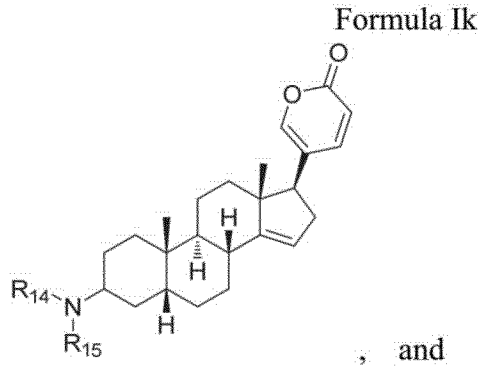
, and
Formula Il:
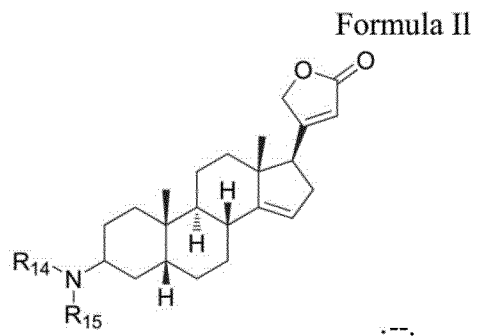
.--.
• Claim 42: Column 137, Lines 16-19:
"(S)-2-amino-N-((3S,5R,8R,9S,10S,13R,14S,17R)-14hydroxy-10,13-dimethyl-17-(2-oxo-2H-pyran-5-yl)hexadecahydro-1H-cyclopenta[a]phenanthren-3-yl)propenamide"
Should read:
-- (S)-2-amino-N-((3S,5R,8R,9S,10S,13R,14S,17R)-14-hydroxy-10,13-dimethyl-17-(2-oxo-2H-pyran-5-yl)hexadecahydro-1H-cyclopenta[a]phenanthren-3-yl)propenamide --.